(12) United States Patent
Tsuboi et al.

(10) Patent No.: US 10,299,868 B2
(45) Date of Patent: May 28, 2019

(54) ROBOT ARM APPARATUS, ROBOT ARM CONTROL METHOD, AND PROGRAM

(71) Applicant: SONY CORPORATION, Tokyo (JP)

(72) Inventors: Toshimitsu Tsuboi, Tokyo (JP); Takara Kasai, Tokyo (JP); Yasuhisa Kamikawa, Tokyo (JP); Yohei Kuroda, Tokyo (JP); Wataru Kokubo, Tokyo (JP); Tetsuharu Fukushima, Tokyo (JP); Yasuhiro Matsuda, Tokyo (JP); Atsushi Miyamoto, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/120,616

(22) PCT Filed: Feb. 13, 2015

(86) PCT No.: PCT/JP2015/054018
§ 371 (c)(1),
(2) Date: Aug. 22, 2016

(87) PCT Pub. No.: WO2015/137038
PCT Pub. Date: Sep. 17, 2015

(65) Prior Publication Data
US 2017/0007336 A1    Jan. 12, 2017

(30) Foreign Application Priority Data

Mar. 14, 2014 (JP) ................................ 2014-052068

(51) Int. Cl.
*A61B 34/00* (2016.01)
*A61B 34/30* (2016.01)
(Continued)

(52) U.S. Cl.
CPC ................. *A61B 34/30* (2016.02); *B25J 9/06* (2013.01); *B25J 9/1633* (2013.01); *B25J 9/1674* (2013.01);
(Continued)

(58) Field of Classification Search
USPC .............................. 700/245–264; 606/1, 130
See application file for complete search history.

(56) References Cited

U.S. PATENT DOCUMENTS 5,276,390 A * 1/1994 Fisher .................... B25J 9/1633
318/561
5,430,643 A * 7/1995 Seraji .................... B25J 9/1643
318/568.11
(Continued)

FOREIGN PATENT DOCUMENTS

CN          102126219 A      7/2011
DE   10 2006 007 858 A1     8/2007
(Continued)

OTHER PUBLICATIONS

Extended European Search Report dated Oct. 6, 2017 in Patent Application No. 15762101.2.
(Continued)

*Primary Examiner* — Jonathan L Sample
(74) *Attorney, Agent, or Firm* — Oblon, McClelland, Maier & Neustadt, L.L.P.

(57) ABSTRACT

A medical support arm apparatus including: an arm unit including a plurality of links joined to each other by one or a plurality of a joint unit; and a driving control unit that drives the arm unit by controlling driving of the joint unit. If a malfunction is detected in at least one of the joint unit, the driving control unit controls the driving of the joint unit
(Continued)

in a state in which a certain restriction is imposed on motion of the arm unit, and drives the arm unit to avoid the malfunction.

18 Claims, 21 Drawing Sheets

(51) Int. Cl.
  *B25J 9/16* (2006.01)
  *B25J 9/06* (2006.01)
  *A61B 90/00* (2016.01)
(52) U.S. Cl.
  CPC ....... *A61B 90/361* (2016.02); *A61B 2034/301* (2016.02); *G05B 2219/40344* (2013.01); *G05B 2219/41114* (2013.01); *Y10S 901/09* (2013.01)

(56) References Cited

U.S. PATENT DOCUMENTS

| | | | | |
|---|---|---|---|---|
| 5,737,500 | A * | 4/1998 | Seraji | B25J 9/1643 318/568.11 |
| 6,127,792 | A * | 10/2000 | Kamiya | B25J 9/1656 318/432 |
| 6,212,443 | B1 * | 4/2001 | Nagata | G05B 19/423 318/568.13 |
| 6,216,056 | B1 * | 4/2001 | Ito | B25J 9/16 700/157 |
| 6,364,888 | B1 * | 4/2002 | Niemeyer | H04N 13/327 606/130 |
| 6,408,224 | B1 * | 6/2002 | Okamoto | B25J 9/1661 29/721 |
| 6,424,885 | B1 * | 7/2002 | Niemeyer | A61B 34/70 600/109 |
| 6,493,608 | B1 * | 12/2002 | Niemeyer | B25J 9/1689 700/302 |
| 8,749,190 | B2 * | 6/2014 | Nowlin | B25J 9/1682 318/568.21 |
| 9,820,822 | B2 * | 11/2017 | Cohen | A61B 90/50 |
| 2003/0135303 | A1 * | 7/2003 | Arai | B25J 9/1679 700/245 |
| 2005/0166413 | A1 * | 8/2005 | Crampton | B25J 13/088 33/503 |
| 2007/0013336 | A1 * | 1/2007 | Nowlin | B25J 9/1682 318/568.21 |
| 2007/0120512 | A1 * | 5/2007 | Albu-Schäffer | B25J 9/1633 318/568.2 |
| 2007/0151389 | A1 * | 7/2007 | Prisco | B25J 9/1633 74/490.05 |
| 2007/0162164 | A1 * | 7/2007 | Dariush | B25J 9/1602 700/61 |
| 2008/0046122 | A1 * | 2/2008 | Manzo | A61B 1/00149 700/245 |
| 2009/0074252 | A1 * | 3/2009 | Dariush | G11C 11/5621 382/107 |
| 2009/0088774 | A1 * | 4/2009 | Swarup | A61B 34/37 606/130 |
| 2009/0105878 | A1 * | 4/2009 | Nagasaka | B25J 13/084 700/245 |
| 2009/0118863 | A1 * | 5/2009 | Dariush | B25J 9/1666 700/255 |
| 2009/0171505 | A1 * | 7/2009 | Okazaki | B25J 9/1676 700/258 |
| 2009/0272585 | A1 * | 11/2009 | Nagasaka | B25J 9/1633 180/8.6 |
| 2010/0168919 | A1 * | 7/2010 | Okamoto | B25J 9/06 700/275 |
| 2011/0082462 | A1 * | 4/2011 | Suarez | A61B 34/20 606/99 |
| 2011/0106306 | A1 * | 5/2011 | Kim | B25J 9/1664 700/246 |
| 2011/0160745 | A1 * | 6/2011 | Fielding | B25J 9/1689 606/130 |
| 2011/0218673 | A1 * | 9/2011 | Oga | B25J 9/1651 700/254 |
| 2011/0264108 | A1 * | 10/2011 | Nowlin | B25J 9/1682 606/130 |
| 2012/0289946 | A1 * | 11/2012 | Steger | A61B 17/29 606/1 |
| 2013/0053866 | A1 * | 2/2013 | Leung | B25J 9/1689 606/130 |
| 2013/0116706 | A1 * | 5/2013 | Lee | A61B 34/30 606/130 |
| 2014/0052155 | A1 * | 2/2014 | Hourtash | B25J 9/1643 606/130 |
| 2014/0296876 | A1 * | 10/2014 | Poquet | A61B 90/50 606/130 |
| 2014/0316575 | A1 * | 10/2014 | Takagi | B25J 9/1633 700/261 |
| 2017/0181806 | A1 * | 6/2017 | Itkowitz | A61B 34/30 |

FOREIGN PATENT DOCUMENTS

| | | |
|---|---|---|
| JP | 3-3786 A | 1/1991 |
| JP | 9-85656 A | 3/1997 |
| JP | 10-230489 A | 9/1998 |
| JP | 2000-343469 A | 12/2000 |
| JP | 2004-174644 A | 6/2004 |
| JP | 2009-95959 A | 5/2009 |
| JP | 2010-142909 A | 7/2010 |
| JP | 2010-142909 A5 | 7/2010 |
| JP | 2015-502767 | 1/2015 |
| WO | WO 2013/045645 A1 | 4/2013 |

OTHER PUBLICATIONS

International Search Report dated May 19, 2015 in PCT/JP2015/054018 (submitting English translation only, previously filed).

Combined Chinese Office Action and Search Report dated May 3, 2018 in corresponding Patent Application No. 201580012311.2 (with English Translation), 13 pages.

Nagasaka et al., "The Application of Generalized Inverse Dynamics to the Robot Equipped with Idealized Joint Units," Sony Corporation, Oct. 24, 2008, 8 pp.

Office Action dated Jan. 17, 2019 in corresponding Chinese Application 2015800123112 (with English Translation), citing document AO therein, 14 pages.

* cited by examiner

ROBOT ARM APPARATUS, ROBOT ARM CONTROL METHOD, AND PROGRAM

TECHNICAL FIELD

The present disclosure relates to a robot arm apparatus, a robot arm control method, and a program.

BACKGROUND ART

Recently, in the medical field, when performing various medical procedures (for example, examinations and surgeries), it is conceivable to attach various types of medical tools to the front edge of an arm unit, and by controlling the driving of the such a robot arm apparatus, observe a surgical site of a patient or perform various treatments on the surgical site of the patient. With such a robot arm apparatus, various medical procedures are performed by causing the medical tool attached to the front edge of the arm unit to touch the patient, or by inserting the medical tool into a body cavity of the patient. For this reason, driving control of the robot arm apparatus that takes safety into consideration is demanded so that the patient is not injured by the medical tool.

For example, Patent Literature 1 discloses technology for a robot apparatus in which an insertion guide trocar is inserted into a patient's body, a manipulator having a treatment tool is attached to the front edge is passed through the cannula of the trocar and inserted into the patient's body cavity, and various treatments are performed. The technology provides a pressure sensor on the outer circumferential wall of the trocar, and switches between a free state allowing the manipulator to move freely and a locked state that locks the manipulator in place, depending on a detection value from the pressure sensor.

CITATION LIST

Patent Literature

Patent Literature 1: JP 2003-79638A

SUMMARY OF INVENTION

Technical Problem

However, with the technology described in Patent Literature 1, in the case of switching to the locked state, for example, since the motion of the manipulator is locked in that state, continuing treatment as-is is difficult, and a temporary interruption in the treatment is necessary. On the other hand, for some medical procedures performed on a patient using a robot arm apparatus, such as surgeries involving the excision of an affected part, for example, interrupting the treatment may risk endangering the patient. In this way, depending on the content of the medical procedure, there is a risk that even though a malfunction may be detected, locking the motion of the manipulator may not necessarily be a safe process for the patient. Additionally, for the driving control of a robot arm apparatus when a malfunction is detected, it is necessary to consider not only the safety of the patient, but also the safety of the surgeon. For example, if a situation occurs in which the arm unit of the robot arm apparatus moves unexpectedly when a malfunction is detected, there is a risk of injuring the surgeon and the patient due to collision with the arm unit or the like.

In light of the above circumstances, controlling the driving of a robot arm apparatus more safely is demanded. Accordingly, the present disclosure proposes a new and improved robot arm apparatus, operation determination method, and program enabling further improvement in safety.

Solution to Problem

According to the present disclosure, there is provided a robot arm apparatus including: an arm unit made up of a plurality of links joined to each other by one or a plurality of a joint unit; and a driving control unit that drives the arm unit by controlling driving of the joint unit. If a malfunction is detected in at least one of the joint unit, the driving control unit controls the driving of the joint unit in a state in which a certain restriction is imposed on motion of the arm unit, and drives the arm unit to avoid the malfunction.

According to the present disclosure, there is provided a robot arm control method including: detecting, in an arm unit made up of a plurality of links joined to each other by one or a plurality of a joint unit, a malfunction in at least one of the joint unit; and controlling driving of the joint unit in a state in which a certain restriction is imposed on motion of the arm unit, and driving the arm unit to avoid the malfunction.

According to the present disclosure, there is provided a program causing a processor of a computer to realize: a function of detecting, in an arm unit made up of a plurality of links joined to each other by one or a plurality of a joint unit, a malfunction in at least one of the joint unit; and a function of controlling driving of the joint unit in a state in which a certain restriction is imposed on motion of the arm unit, and driving the arm unit to avoid the malfunction.

According to the present disclosure, when a malfunction is detected in any joint unit constituting the arm unit, a restriction is provided to avoid the malfunction, and then the driving of the joint unit is controlled, and the arm unit is driven. Consequently, even if a malfunction occurs in a joint unit, the arm unit is driven to avoid the malfunction, and a situation that would endanger the surgeon and the patient due to unexpected motion of the arm unit is avoided, for example.

Advantageous Effects of Invention

According to the present disclosure as described above, further improvement in safety becomes possible. Note that the above advantageous effects are not strictly limiting, and that any advantageous effect indicated in the present disclosure or another advantageous effect that may be reasoned from the present disclosure may also be exhibited in addition to, or instead of, the above advantageous effects.

DESCRIPTION OF EMBODIMENT(S)

Figure 1:
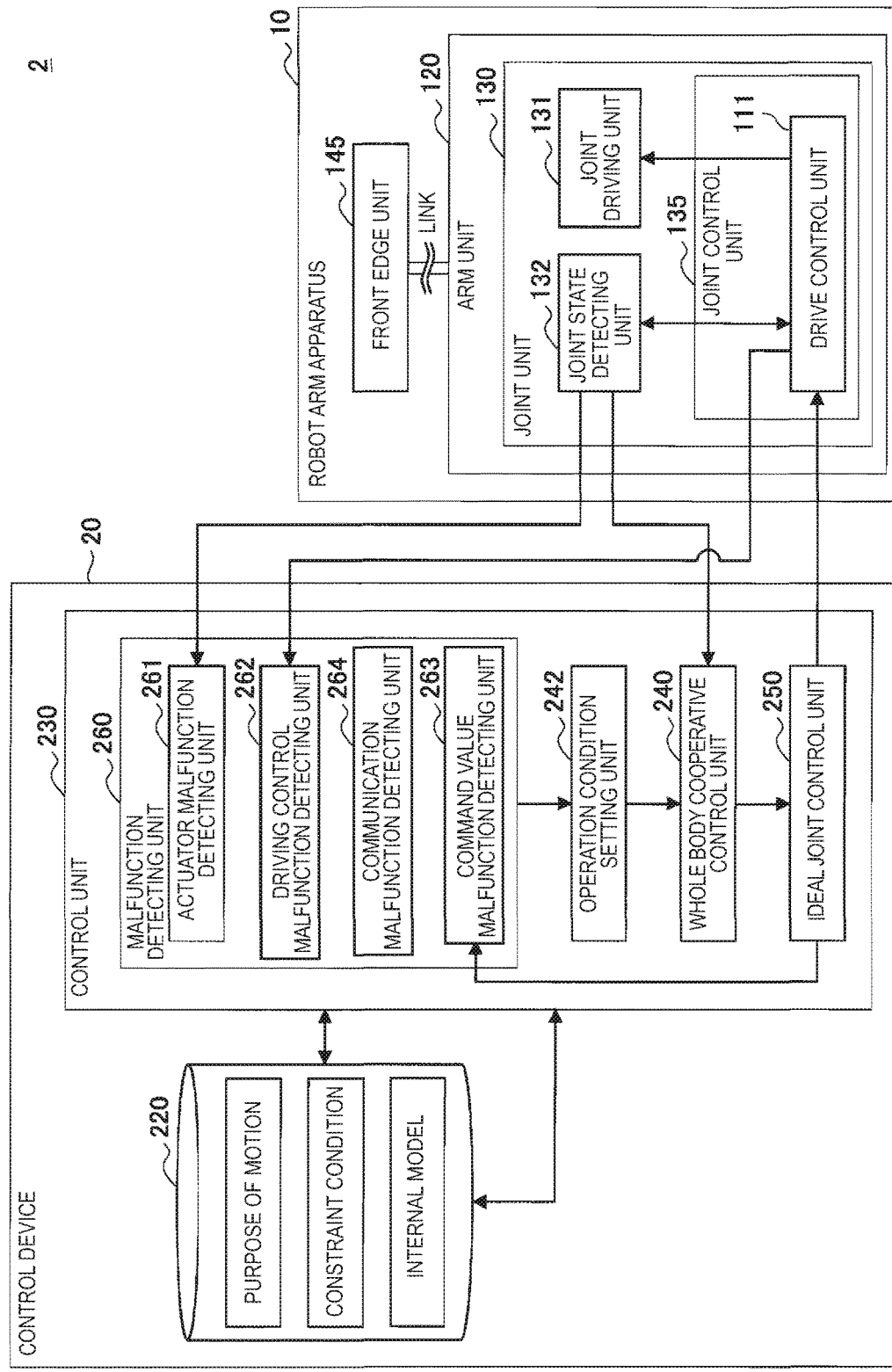
FIG. 1 is a function block diagram illustrating a schematic configuration of a robot arm control system according to an embodiment of the present disclosure.

Hereinafter, (a) preferred embodiment(s) of the present disclosure will be described in detail with reference to the appended drawings. In this specification and the drawings, elements that have substantially the same function and structure are denoted with the same reference signs, and repeated explanation is omitted.

The description will proceed in the following order.
1. Investigation into safety of robot arm apparatus
2. Functional configuration of robot arm control system
3. Hardware configuration of robot arm control system
4. Processing procedure of operation determination method
5. Details of each process
5-1. Malfunction detection process
5-2. Malfunction avoidance operation
5-3. Partial function suspension operation
5-4. Function suspension operation
6. Whole body cooperative control
6-1. Review of medical robot arm apparatus
6-2. Embodiment of present disclosure
6-2-1. External appearance of robot arm apparatus
6.2.2. Generalized inverse dynamics
6-2-2-1. Virtual force calculating process
6-2-2-2. Actual force calculating process
6-2-3. Ideal joint control
6-2-4. Configuration of robot arm control system
6-2-5. Specific example of purpose of motion
6-3. Processing procedure of robot arm control method
6-4. Summary of robot arm apparatus according to whole body cooperative control
7. Hardware configuration
8. Supplement In this specification, first, in <1. Investigation into safety of robot arm apparatus>, to further clarify the present disclosure, the features demanded of a robot arm apparatus from the perspective of safety will be investigated, and the background leading up to the inventors' conception of the present disclosure will be described. Next, in <2. Functional configuration of robot arm control system>, <3. Hardware configuration of robot arm control system>, <4. Processing procedure of operation determination method>, and <5. Details of each process>, the configuration of a control system of a robot arm apparatus and a control method of a robot arm apparatus according to a preferred embodiment conceived by the inventors from the perspective of safety discussed above will be described.

Herein, in the present embodiment, a control technique called whole body cooperative control may be applied as the control technique of the robot arm apparatus described from <2. Functional configuration of robot arm control system> to <5. Details of each process>. With whole body cooperative control according to the present embodiment, a control quantity for each joint unit is computed so that the arm unit realizes a certain purpose of motion, and by driving each joint unit cooperatively based on the control quantity, the driving of the arm unit is controlled. Additionally, when a control quantity for each joint unit is computed, a certain constraint condition that restricts the motion of the arm unit (for example, position, velocity, or force) may also be provided. In <6. Whole body cooperative control>, a configuration of a control system and a control method for realizing such whole body cooperative control will be described by taking a robot arm apparatus for medical use as an example. Note that in the present embodiment, using whole body cooperative control makes it possible to satisfy not only the safety discussed earlier, but also the various kinds of features demanded of a robot arm apparatus for medical use. Accordingly, in <6. Whole body cooperative control>, whole body cooperative control of a robot arm apparatus will be described not just from the perspective of safety discussed above, but from a broader perspective.

Note that in the following description, a robot arm apparatus primarily for medical use will be taken as an example of a preferred embodiment of the present disclosure. However, the present embodiment is not limited to such an example, and is also applicable to other fields, such as industrial use, for example.

<1. Investigation into Safety of Robot Arm Apparatus>

First, before describing a preferred embodiment of the present disclosure, the features demanded of a robot arm apparatus from the perspective of safety will be described by taking a robot arm apparatus for medical use as an example.

When a robot arm apparatus is used for a medical application, the anticipated usage method is one in which any of various medical tools, such as an imaging device or a treatment tool, is attached to the front edge of the arm unit, and a patient's surgical site is observed with the imaging device, or various treatments are performed on the surgical site with the treatment tool. In this case, it is necessary to ensure the safety of both the patient and the surgeon performing various medical procedures by operating the robot arm apparatus. Herein, safety for the surgeon conceivably refers to the surgeon him- or herself not being injured, such as being wounded or burned, due to the driving of the robot arm apparatus. On the other hand, safety for the patient may include not being injured, such as being wounded or burned, due to the driving of the robot arm apparatus, but may also include not increasing the burden on the patient, such as the medical procedure being interrupted or the duration of the medical procedure being increased due to function suspension of the robot arm apparatus or the like. Herein, function suspension means a state in which normal control is not being performed on the arm unit of the robot arm apparatus, and the arm unit is being driven differently from normal.

As a situation that may be dangerous, first, a case is conceivable in which the arm unit moves unexpectedly to the surgeon due to incorrect operation by the surgeon or some kind of fault in the hardware or the software, for example. For example, a situation is conceivable in which, when the surgeon operates the arm unit to bring a medical tool close to the patient, the medical tool approaches the patient with excessive velocity or force, and the patient is injured by the medical tool. Additionally, if the arm unit moves unexpectedly to the surgeon, there is also a possibility of the surgeon him- or herself being exposed to danger, such as colliding with the arm unit. From the perspective of safety for the surgeon and the patient, there is demand to determine such unexpected motion of the arm unit due to incorrect operation or due to some kind of fault as a malfunction, and control the driving of the arm unit so as to perform an operation that avoids the malfunction (malfunction avoidance operation).

In addition, as another situation that may be dangerous, a situation is conceivable in which part of the arm unit does not operate correctly due to a failure. For example, as described in Patent Literature 1 above, in a typical robot arm apparatus, when a malfunction is detected in any part of the arm unit, the position and the orientation of the arm unit are locked so as not to move from that state, and whole arm unit is put into a what is called a stationary state. However, if the robot arm apparatus enters the stationary state, the medical procedure must be interrupted, which may possibly increase the duration of the medical procedure. Consequently, when a failure occurs in the arm unit, for example, there is demand to identify the joint unit where the failure occurs, lock the motion of the failed joint unit, and control the driving of the arm unit so as to perform an operation that maintains the driving of the arm unit with all other joint units (partial function suspension operation).

In addition, when an emergency situation such as a power outage occurs, or when a serious failure occurs in the arm unit, a situation may occur in which the partial function suspension operation is inadequate, and the functions of the arm unit must be suspended completely. In this case, it is desirable to suspend the functions of the arm unit more safely, so that the suspended arm unit does not inflict harm to the surgeon and the patient, for example. In addition, from the perspective of decreasing the burden on the patient, it is preferable to provide a mechanism that suspends the functions of the arm unit while also enabling a smooth transition to a medical procedure performed manually by the surgeon, for example. For example, it is necessary to prevent the arm unit from moving unexpectedly at the same time as the function suspension, and prevent the suspended arm unit from interfering with subsequent work. In this way, there is demand for control of the driving of the arm unit so that the operation of suspending the functions of the arm unit (function suspension operation) is performed more safely.

In addition, it is desirable to make a selection among the malfunction avoidance operation, the partial function suspension operation, and the function suspension operation discussed above so that the direct continuance of the medical procedure is prioritized and the functions of the robot arm apparatus are maintained as much as possible. For example, when a malfunction is detected in the arm unit, if both the function suspension operation and the partial function suspension operation are selectable as a measure that may be taken in response to the malfunction, it is preferable to select the partial function suspension operation. Similarly, if both the partial function suspension operation and the malfunction avoidance operation are selectable in response to a detected malfunction, it is preferable to select the malfunction avoidance operation. Consequently, the driving of the robot arm apparatus is controlled so that the medical procedure is continued as much as possible. In order to select such an operation, when a malfunction is detected in the arm unit, there is demand to accurately detect the part where the malfunction is occurring and the type of malfunction, and appropriately determine which operation to switch to. In a robot arm apparatus for medical use, such an accurate malfunction detecting function is also demanded.

As described above, the following features are demanded of a robot arm apparatus from the perspective of safety. Namely, the demanded features are the ability to execute a malfunction avoidance operation, the ability to execute a partial function suspension operation, the ability to execute a function suspension operation safely, and the ability to accurately execute a malfunction detection process for determining which of these operations to switch to.

As a result of thorough investigation into technologies that satisfy these features, the inventors conceived the preferred embodiment of the present disclosure indicated below. Hereinafter, the preferred embodiment of the present disclosure will be described in detail.

<2. Functional Configuration of Robot Arm Control System>

A functional configuration of a robot arm control system according to an embodiment of the present disclosure will be described with reference to FIG. 1. FIG. 1 is a function block diagram illustrating a schematic configuration of a robot arm control system according to an embodiment of the present disclosure.

Referring to FIG. 1, the robot arm control system 2 according to the present embodiment is equipped with a robot arm apparatus 10 and a control device 20. In the present embodiment, various computations for driving the robot arm apparatus 10 by whole body cooperative control are performed by the control device 20, and the driving of an arm unit 120 of the robot arm apparatus 10 is controlled based on the computational results. Additionally, the arm unit 120 of the robot arm apparatus 10 is provided with a front edge unit 145 discussed later, and by controlling the driving of the arm unit 120, various medical procedures are performed on a patient by the front edge unit 145. Hereinafter, the configuration of the robot arm apparatus 10 and the control device 20 will be described in detail.

The robot arm apparatus 10 includes an arm unit, which is a multi-link structure made up of multiple links joined to each other by multiple joint units. By driving the arm unit within a movable range, the robot arm apparatus 10 controls the position and the orientation of a front edge unit 145 provided on the front edge of the arm unit.

Referring to FIG. 1, the robot arm apparatus 10 includes an arm unit 120. Also, the arm unit 120 includes a joint unit 130 and the front edge unit 145.

The arm unit 120 is a multi-link structure made up of multiple joint units 130 and multiple links, and the driving of the arm unit 120 is controlled as a result of the driving of each joint unit 130 being controlled. Note that since the function and configuration of the multiple joint units 130 included in the arm unit 120 are similar to each other, FIG. 1 illustrates the configuration of one joint unit 130 as a representative of these multiple joint units 130.

The joint unit 130 rotatably joins links to each other in the arm unit 120. The rotational driving of the joint unit 130 is controlled by control from the joint control unit 135 discussed later. The joint unit 130 includes a joint driving unit 131, a joint state detecting unit 132, and a joint control unit 135. Also, although omitted from illustration for the sake of simplicity, the joint unit 130 additionally may be equipped with a communication unit that transmits and receives various information to and from external equipment. The control device 20 similarly is provided with a communication unit (not illustrated), and the joint unit 130 is able to transmit and receive various information to and from the control device 20 as well as other joint units 130 through the communication unit.

The joint driving unit 131 is a driving mechanism such as a motor constituting an actuator of the joint unit 130. The driving of the joint driving unit 131 rotationally drives the joint unit 130. The driving of the joint driving unit 131 is controlled by the drive control unit 111 of the joint control unit 135 described later. For example, a motor constituting the joint driving unit 131 is driven by an amount of current corresponding to an instruction from the drive control unit 111.

The joint state detecting unit 132 detects the state of the joint unit 130. Herein, the state of the joint unit 130 may mean the drive state of the joint unit 130. For example, the state of the joint unit 130 includes information such as the rotational angle, the rotational angular velocity, the rotational angular acceleration, the generated torque, and the external torque of the joint unit 130. In addition, the state of the joint unit 130 additionally may include various information when the joint unit 130 drives, like information such as an amount of current supplied to the motor of an actuator and the ambient temperature of the motor, and information such as the communication state in the communication unit by which the joint unit 130 communicates with other joint units 130 and the control device 20. In the present embodiment, the joint state detecting unit 132 includes various sensors, such as an angular sensor (encoder), a torque sensor, a current sensor and/or a temperature sensor, for example, and is able to detect factors such as the rotational angle, the generated torque, the external torque, the amount of current, and the temperature of the joint unit 130.

The joint state detecting unit 132 transmits the detected state of the joint unit 130 to the control device 20. In the control device 20, a malfunction of the joint unit 130 is detected based on this information indicating the state of the joint unit 130. Also, in the control device 20, the state of the arm unit 120 (arm state) is acquired based on the information indicating the state of the joint unit 130, and a control value is computed for each joint unit 130 so that the arm unit 120 achieves a certain purpose of motion. For example, among the information indicating the state of the joint unit 130, information about factors such as the amount of current supplied to the motor of the actuator, the ambient temperature of the motor, the rotational angle of the input shaft (motor) and the output shaft, the generated torque, the external torque, and the communication state of the communication unit are primarily used for malfunction detection. As another example, among the information indicating the state of the joint unit 130, information that primarily expresses the motion of the joint unit 130, such as the rotational angle, the rotational angular velocity, the rotational angular acceleration, the generated torque, and the external torque of the joint unit 130 primarily may be used to compute the control quantity. Note that since the computation of the control quantity is described in further detail in <6. Whole body cooperative control> below, detailed description will be reduced or omitted at this point.

The joint control unit 135 is made up of any of various types of processors such as a central processing unit (CPU), for example, and controls the driving of the joint unit 130. As a result of the processor constituting the joint control unit 135 operating in accordance with a certain program, the respective functions of the joint control unit 135 are realized. In the present embodiment, the joint control unit 135 includes a drive control unit 111 as a function. Note that the joint control unit 135 additionally may include other functions for controlling the operation of the structural elements provided in the joint unit 130, such as a communication control unit that controls the operation of the communication unit provided in the joint unit 130, and causes the communication unit to transmit and receive certain information, for example.

The drive control unit 111 controls the driving of the arm unit 120 by controlling the driving of the joint unit 130. More specifically, the drive control unit 111, by controlling an amount of current supplied to the joint driving unit 131 of the joint unit 130, controls the rotational speed of a motor constituting the joint driving unit 131, and controls the rotational angle and the generated torque in the joint unit 130. Additionally, if the joint unit 130 is provided with a brake mechanism that prevents such rotation, for example, the drive control unit 111 may also cause the brake mechanism to engage, and suspend rotational driving of the joint unit 130. Herein, as discussed above, the driving control of the joint unit 130 by the drive control unit 111 may be conducted based on a computational result in the control device 20.

In addition, although described in (5-4. Function suspension operation) below, when the function suspension operation is executed, situations are conceivable in which the computational result in the control device 20 is not transmitted to the joint unit 130, such as if communication between the control device 20 and the joint unit 130 is cut off. As a result of communication with the control device 20 being cut off, whole body cooperative control can no longer be executed, and what is called force control is no longer conducted, but with the function suspension operation, it is necessary to execute control so that the motion of each joint unit 130 is locked, for example. Consequently, in the present embodiment, such driving may be controlled independently for each joint unit 130 by the drive control unit 111 using what is called position control. Consequently, even if communication with the control device 20 is cut off, drive control, such as locking the rotational angle of the joint unit 130 to a certain value, for example, is conducted in each joint unit 130, and the function suspension operation may be realized.

The front edge unit 145 is provided on the front edge of the arm unit 120, and the position and the orientation of the front edge unit 145 are controlled as part of the driving control of the arm unit 120. In the present embodiment, the front edge unit 145 is any of various types of medical tools, such as an imaging device or a treatment tool, for example. In the case in which the front edge unit 145 is an imaging device such as a camera, a microscope, or an endoscope, a conceivable usage method is to capture images of the surgical site of the patient while driving the arm unit 120 to adjust the position and the orientation of the imaging device. For example, an image of the surgical site of the patient captured by the imaging device may be displayed on the display screen of a display device, and the surgeon is able to observe the state of the surgical site and perform various treatments on the surgical site while referring to the display screen of the display device. Meanwhile, in the case in which the front edge unit 145 is a treatment tool such as a scalpel or forceps, a conceivable usage method is to drive the arm unit 120 to perform a certain treatment on the surgical site of the patient using the treatment tool. The front edge unit 145 is not limited to these examples, and any of various known medical tools may also be applied as the front edge unit 145.

Note that in FIG. 1, the state of the front edge unit 145 being provided on the tip of the final link through the multiple joint units 130 and multiple links is expressed by schematically illustrating a link between the joint unit 130 and the front edge unit 145. Also, although labeled the front edge unit 145 for the sake of convenience in the example illustrated in FIG. 1, in the present embodiment, the part where the front edge unit 145 is provided is not limited to the front edge of the arm unit 120. In the present embodiment, it is sufficient for the position and the orientation of the front edge unit 145 to be controlled as part of the driving of the arm unit 120, and for the front edge unit 145 to be configured so that various medical procedures may be performed on a patient. The part where the front edge unit 145 is attached to the arm unit 120 is arbitrary.

The above thus describes the function and configuration of the robot arm apparatus 10. Next, the function and configuration of the control apparatus 20 will be described. Referring to FIG. 1, the control apparatus 20 includes a storage unit 220 and a control unit 230.

The control unit 230 is made up of any of various types of processors such as a CPU, for example. The control unit 230 centrally controls the operation of the control device 20, while also performing various computations for controlling the driving of the arm unit 120 in the robot arm apparatus 10. As a result of the processor constituting the control unit 230 operating in accordance with a certain program, the respective functions of the control unit 230 are realized. In the present embodiment, the control unit 230 performs various computations for whole body cooperative control and ideal joint control in order to control the driving of the arm unit 120 of the robot arm apparatus 10. Also, the control unit 230 additionally includes a function of detecting a malfunction in the joint unit 130, based on the detected state of the joint unit 130.

The functional configuration of the control unit 230 will be described in detail. The control unit 230 includes a whole body cooperative control unit 240, an ideal joint control unit 250, a malfunction detecting unit 260, and an operation condition setting unit 242.

The malfunction detecting unit 260 detects a malfunction occurring in the joint unit 130, based on various information for detecting a malfunction of the joint unit 130. Herein, the information for detecting a malfunction of the joint unit 130 may include, for example, information about the state of the joint unit 130 detected by the joint state detecting unit 132, information about driving control of the joint unit 130 as discussed later, information about a command value transmitted to the joint unit 130, and information about the communication state of the joint unit 130. For example, the malfunction detecting unit 260 includes an actuator malfunction detecting unit 261, a driving control malfunction detecting unit 262, a command value malfunction detecting unit 263, and a communication malfunction detecting unit 264 as functions.

The actuator malfunction detecting unit 261 detects a malfunction in the actuator provided to drive the joint unit 130. For example, the actuator malfunction detecting unit 261 is able to detect a malfunction in the actuator based on information included in the information indicating the state of the joint unit 130, such as the amount of current supplied to the motor of the actuator, the ambient temperature of the motor, the rotational angle of the input shaft (motor) and the output shaft, the generated torque, and the external torque.

The driving control malfunction detecting unit 262 detects a malfunction of the joint unit 130 based on information about the driving control of the joint unit 130 transmitted from the drive control unit 111. For example, the driving control malfunction detecting unit 262 is able to detect a malfunction of the joint unit 130 when the joint unit 130 is driving even though the brake mechanism is being driven by the drive control unit 111, or conversely, when the joint unit 130 is not driving even though the brake mechanism is not being driven.

The command value malfunction detecting unit 263 detects a malfunction of the joint unit 130 based on a command value transmitted from the control device 20 to the joint unit 130. Herein, the command value is a value computed by the ideal joint control unit 250, and is a control quantity for ultimately controlling the driving of the joint unit 130 transmitted from the control device 20 to the drive control unit 111 of the joint unit 130. For example, the command value malfunction detecting unit 263 is able to detect a malfunction of the joint unit 130 when the command value transmitted to the drive control unit 111, and the driving of the joint unit 130 driven based on that command value, diverge from each other.

The communication malfunction detecting unit 264 detects a malfunction of the joint unit 130 based on the communication state between the joint unit 130 and the control device 20. For example, when the communication unit of the joint unit 130 and/or the communication unit of the control device 20 are not operating correctly, and communication between the communication units is cut off, there is a possibility that information needed to compute the control quantity (for example, information expressing the state of the joint unit 130) may not be transmitted from the joint unit 130 to the control device 20, or that information about the control quantity computed by the control device 20 may not be received by the joint unit 130. Consequently, the communication malfunction detecting unit 264 is able to detect a joint unit 130 for which the communication unit is not operating correctly and for which the control quantity computed by the control device 20 cannot be received as a joint unit 130 in which a malfunction is occurring.

Herein, the various information for detecting a malfunction of the joint unit 130 as discussed above (such as the information about the state of the joint unit 130 acquired by the joint state detecting unit 132, the information about the driving control of the joint unit 130, the information about the command value transmitted from the control device 20 to the joint unit 130, and/or the information about the communication state between the joint unit 130 and the control device 20) is information that may be acquired for each joint unit 130. Consequently, the malfunction detecting unit 260 is able to detect the presence or absence of a malfunction in each joint unit 130. Additionally, the malfunction detecting unit 260 concurrently may detect which structural member of the joint unit 130 is experiencing a malfunction as well as the type of malfunction, depending on which information serves as the basis for detecting the malfunction.

The malfunction detecting unit 260 transmits information about a detected malfunction to the operation condition setting unit 242. Note that the malfunction detection process conducted by the malfunction detecting unit 260 is described in further detail in (5-1. Malfunction detection process) below.

Note that in the example illustrated in FIG. 1, for the sake of convenience of explanation, the functions of the malfunction detecting unit 260 are illustrated separately as the actuator malfunction detecting unit 261, the driving control malfunction detecting unit 262, the command value malfunction detecting unit 263, and the communication malfunction detecting unit 264. However, in the present embodiment, the malfunction detecting unit 260 may detect a malfunction in the joint unit 130 by comprehensively considering information such as the information about the state of the joint unit 130 acquired by the joint state detecting unit 132, the information about the driving control of the joint unit 130, the information about the command value transmitted from the control device 20 to the joint unit 130, and/or the information about the communication state between the joint unit 130.

The operation condition setting unit 242 sets an operation condition for the computation of the control quantity conducted by the whole body cooperative control unit 240 and the ideal joint control unit 250. In the present embodiment, the operation condition setting unit 242 sets the operation condition according to the type of malfunction of the joint unit 130 detected by the malfunction detecting unit 260. Specifically, the operation condition setting unit 242 is able to determine the operation to be performed by the arm unit 120 according to the type of the detected malfunction of the joint unit 130, and set an operation condition corresponding to that operation. Herein, the operation to be performed by the arm unit 120 may be any of the malfunction avoidance operation, the partial function suspension operation, and the function suspension operation discussed earlier.

For example, a table associating the type of malfunction, the operation that may be executed when that malfunction occurs, and the operation condition for executing that operation is stored in the storage unit 220, and the operation condition setting unit 242 is able to determine the operation to be performed by the arm unit 120 and also set the operation condition according to that operation, based on the malfunction detection result from the malfunction detecting unit 260 and the table. In this table, types of malfunctions and operations may be associated so that even if a malfunction occurs, the driving control of the arm unit 120 is continued as much as possible. By determining the operation to be performed by the arm unit 120 based on such a table, the driving of the arm unit 120 is controlled so that a medical procedure using the robot arm apparatus 10 is continued as much as possible.

Note that if conditions such as the overall configuration of the arm unit 120 and the control model (internal model) used to compute the control quantity are different, it is conceivable that different operations may be executable even if the same malfunction occurs. Consequently, in the above table, types of malfunctions and operations may also be associated by also taking these conditions into account. The specific structure of the table may be set as appropriate by the designer of the robot arm apparatus 10 or the like.

Specifically, the operation condition set by the operation condition setting unit 242 may include a purpose of motion and a constraint condition. The purpose of motion is various information related to the motion of the arm unit 120, and is, for example, target values for factors such as the position and the orientation (coordinates), the velocity, the acceleration, and the force of the front edge unit 145 and the arm unit 120. Meanwhile, the constraint condition is various information that restricts (constrains) the motion of the arm unit 120, and may be, for example, the coordinates of a region into which none of the structural members of the arm unit 120 should move, values of a velocity and an acceleration at which the arm unit 120 should not move, a value of force that should not be generated, or the like. In addition, if multiple internal models are available depending on the operation to be performed by the arm unit 120, the operation condition setting unit 242 may also set, as the operation condition, an internal model corresponding to the operation determined according to the type of malfunction detected by the malfunction detecting unit 260. The operation condition setting unit 242 provides information about the set operation condition to the whole body cooperative control unit 240.

The whole body cooperative control unit 240 performs various computations related to whole body cooperative control using generalized inverse dynamics. Also, the ideal joint control unit 250 performs various computations related to ideal joint control that realizes an ideal response based on a theoretical model. By controlling the driving of the robot arm apparatus 10 based on these computational results, the robot arm apparatus 10 is driven by force control. In the present embodiment, the whole body cooperative control unit 240 and the ideal joint control unit 250 perform various computations based on the operation condition set by the operation condition setting unit 242, and as a result, a control value for each joint unit 130 is computed so that the arm unit 120 performs the operation determined according to the type of malfunction detected by the malfunction detecting unit 260. Note that processes conducted by the whole body cooperative control unit 240 and the ideal joint control unit 250 will be described in further detail in <6. Whole body cooperative control> later, and at this point only an overview will be described briefly.

The whole body cooperative control unit 240 computes the control quantity for driving the joint unit 130, based on the state of the joint unit 130 detected by the joint state detecting unit 132, and under the operation condition set by the operation condition setting unit 242. Specifically, the whole body cooperative control unit 240 is able to acquired the state of the arm unit 120 (arm state) based on the state of the joint unit 130 detected by the joint state detecting unit 132. The arm state expresses geometric parameters and mechanical parameters of the arm unit 120, and may be expressed as an internal model of the robot arm apparatus 10. Additionally, based on the arm state, the whole body cooperative control unit 240 is able to compute the control value for driving the arm unit 120 (for example, a driving parameter for each joint unit 130 (for example, the generated torque value of the joint unit 130)) so that the purpose of motion set by the operation condition setting unit 242 is achieved, while taking into account the constraint condition set by the operation condition setting unit 242.

The ideal joint control unit 250 makes a correction that takes the influence of disturbance into account to the control value computed by the whole body cooperative control unit 240, and thereby computes a command value ultimately used to drive the arm unit 120. For example, the command value may be a generated torque value of the joint unit 130 that takes the influence of disturbance into account. The ideal joint control unit 250 transmits information about the computed command value to the robot arm apparatus 10. As a result of the drive control unit 111 causing each joint unit 130 to be driven based on the command value, the arm unit 120 is driven in accordance with the constraint condition and the purpose of motion set by the operation condition setting unit 242, or in other words, so as to perform the operation determined according to the type of malfunction detected by the malfunction detecting unit 260.

The storage unit 220 stores various information processed by the control device 20. In the present embodiment, the storage unit 220 is able to store various information used in the computations related to whole body cooperative control and ideal joint control conducted by the control unit 230, as well as information about the results of the computations. For example, the storage unit 220 may also store the purpose of motion, the constraint condition, and the internal model used in the computations related to whole body cooperative control by the whole body cooperative control unit 240. As another example, the storage unit 220 may also store a table associating types of malfunctions that may be detected in the joint unit 130, operations that may be executed when a corresponding malfunction occurs, and operation conditions for executing a corresponding operation. The storage unit 220 may store all kinds of parameters related to various processes conducted by the control unit 230, and the control unit 230 is able to conduct various processes while transmitting and receiving information to and from the storage unit 220.

The above thus describes a configuration of the robot arm control system 2 according to the present embodiment with reference to FIG. 1. As described above, in the present embodiment, the occurrence of a malfunction is detected for each joint unit 130 by the malfunction detecting unit 260. Consequently, it is possible to detect accurately which part of the arm unit 120 experienced a malfunction. Also, in the present embodiment, the operation condition setting unit 242 determines an operation of the arm unit 120 according to the type of malfunction detected by the malfunction detecting unit 260 is determined by the operation condition setting unit 242, and sets an operation condition corresponding to the operation. Subsequently, the whole body cooperative control unit 240 and the ideal joint control unit 250 compute a control quantity for each joint unit 130 for driving the arm unit 120 based on the operation condition, and thus the driving of the arm unit 120 is controlled to perform the operation according to the type of malfunction. Consequently, the driving of the arm unit 120 is controlled according to the type of malfunction so that a medical procedure using the robot arm apparatus 10 is continued as much as possible. Thus, the safety of the patient and the surgeon may be improved.

Note that in the example illustrated in FIG. 1, the malfunction detecting unit 260 is provided in the control device 20, and the process of detecting a malfunction in the joint unit is conducted in the control device 20. However, the present embodiment is not limited to such an example. For example, the joint control unit 135 of each joint unit 130 may include functions similar to the malfunction detecting unit 260, and the detection of a malfunction in the joint unit 130 may be conducted by the joint unit 130 itself.

Additionally, the configuration of the robot arm control system 2 is not limited to the example illustrated in FIG. 1. For example, each process conducted in the joint control unit 135 and the control unit 230 illustrated in FIG. 1 may be conducted in either of the robot arm apparatus 10 and the control device 20, or be conducted by another information processing device (not illustrated) that is communicably connected to the robot arm apparatus 10 and the control device 20. In the present embodiment, it is sufficient to configure the robot arm control system 2 so that each of the functions illustrated in FIG. 1 may be executed, and the specific device configuration is arbitrary.

Each of the above described components of the robot arm control system 2 according to the embodiment may be configured using a versatile member or circuit, and may be configured by hardware specialized for the function of each component. Further, all the functions of the components may be performed by a CPU or the like. Thus, a configuration to be used may be appropriately changed according to a technology level when the present embodiment is carried out.

Further, it is possible to create a computer program for implementing the functions of the robot arm control system 2 according to the present embodiment and install the computer program in a personal computer or the like. Furthermore, it is possible to provide a computer readable recording medium storing the computer program as well. Examples of the recording medium include a magnetic disk, an optical disc, a magneto optical disc, and a flash memory. Further, for example, the computer program may be delivered via a network without using the recording medium.

<3. Hardware Configuration of Robot Arm Control System>

Figure 2:
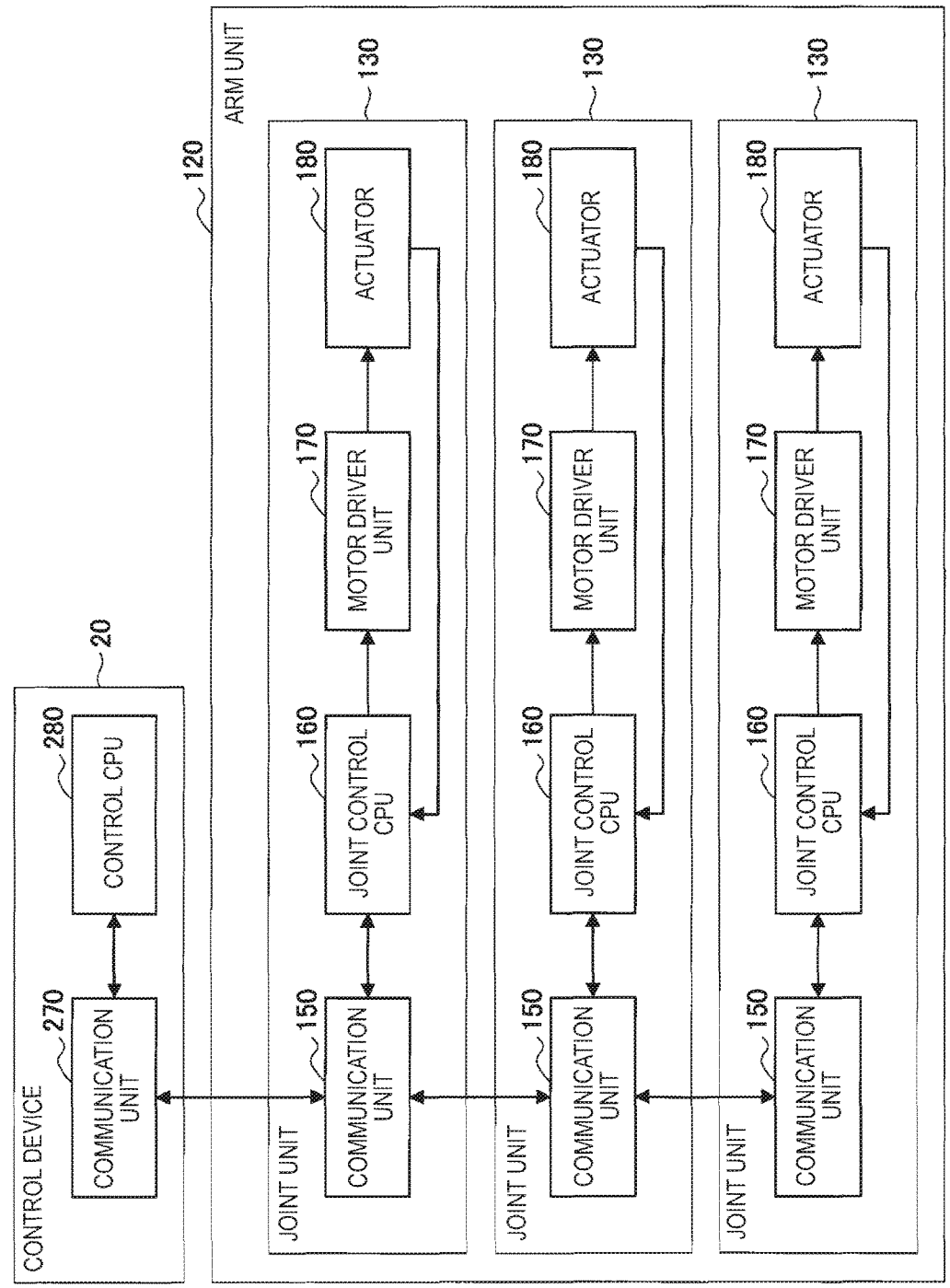
FIG. 2 is a block diagram illustrating a hardware configuration of a robot arm control system according to an embodiment.

Next, a hardware configuration of a robot arm control system according to the present embodiment will be described with reference to FIG. 2. FIG. 2 is a block diagram illustrating a hardware configuration of a robot arm control system according to the present embodiment. Note that the block diagram illustrated in FIG. 2 corresponds to the function block diagram illustrated in FIG. 1, and corresponds to an illustration of the hardware constituting each function block illustrated in FIG. 1. Also, in FIG. 2, for the sake of simplicity, the configuration related to malfunction detection according to the present embodiment primarily is illustrated from among the configuration illustrated in FIG. 1, whereas other parts of the configuration are omitted from illustration.

Additionally, referring to FIG. 2, a configuration corresponding to multiple joint units 130 of the arm unit 120 of the robot arm apparatus is illustrated. In actuality, links are joined to each other by each of the joint units 130 to thereby constitute a multi-link structure, but in FIG. 2, illustration of the links is omitted. Additionally, in FIG. 2, three joint units 130 are illustrated as an example, but the number of joint units 130 is not limited to such an example, and different numbers of joint units 130 may also exist depending on the configuration of the arm unit 120.

(Control Device)

Referring to FIG. 2, a communication unit 270 and a control CPU 280 are illustrated as the configuration included in the control device 20. The communication unit 270 is a communication interface that transmits and receives various information to and from each of the joint units 130 of the robot arm apparatus (more specifically, each of the communication units 150 of the joint units 130 discussed later). In the present embodiment, the communication unit 270 receives various information for detecting a malfunction of the joint units 130 transmitted from each of the joint units 130. Additionally, the communication unit 270 transmits to each of the joint units 130 information about the control quantity for each of the joint units 130 of the arm unit 120 computed by the control CPU 280.

The control CPU 280 corresponds to the control unit 230 illustrated in FIG. 1. In the control CPU 280, a malfunction of the joint units 130 is detected based on the various information for detecting a malfunction of the joint units 130 transmitted from each of the joint units 130. Additionally, the type of the detected malfunction is determined, and the operation of the arm unit 120 is determined according to the type of malfunction. Furthermore, an operation condition corresponding to the determined operation of the arm unit 120 is set, and based on this operation condition, the control quantity for each of the joint units 130 is computed so as to realize the operation of the arm unit 120.

(Joint Units)

Each of the joint units 130 includes a communication unit 150, a joint control CPU 160, a motor driver unit 170, and an actuator 180. The communication unit 150 is a communication interface that transmits and receives various information to and from the communication units 150 of the other joint units 130 and the communication unit 270 of the control device 20. In the present embodiment, various information for detecting a malfunction of the joint units 130 is transmitted from each of the joint units 130 to the control device 20 by the communication unit 150. Additionally, the communication unit 150 receives information about the control quantity for each of the joint units 130 of the arm unit 120 computed by the control CPU 280.

The joint control CPU 160 corresponds to the joint control unit 135 illustrated in FIG. 1. For example, a control quantity (for example, an amount of current) for driving the motor of the actuator 180 is relayed from the joint control CPU 160 to the motor driver unit 170 (this corresponds to the function of the drive control unit 111 illustrated in FIG. 1 discussed earlier, for example). Such configurations for controlling the driving of the actuator 180 by the joint control CPU 160 will be discussed in detail later with reference to FIGS. 3 to 5.

In addition, information about detected values (such as an amount of current, temperature, and rotational angle, for example) from respective sensors installed onboard the actuator 180, or in other words, information indicating the state of the joint unit 130, is transmitted from the actuator 180 to the joint control CPU 160. The information indicating the state of the joint unit 130 is transmitted to the control device 20 via the communication unit 150. Also, as discussed later with reference to FIGS. 3 to 5, in the joint control CPU 160, driving control of the actuator 180 may be conducted based on not only the control quantity transmitted from the control device 20, but also the detected values from the respective sensors of the actuator 180. Note that although FIG. 2 illustrates the information about the detected values from the respective sensors of the actuator 180 being transmitted from the communication unit 150 to the control device 20 via the joint control CPU 160, the information about the detected values may also be transmitted to the control device 20 via the communication unit 150. In addition, the configuration of the respective sensors installed onboard the actuator 180 will be discussed in detail later with reference to FIG. 6.

The motor driver unit 170 is a driver circuit (driver integrated circuit (IC)) that rotationally drives the motor of the actuator 180 by supplying current to the motor, and is able to control the rotational rate of the motor by adjusting the amount of current supplied to the motor. The motor driver unit 170 drives the motor of the actuator 180 according to a control quantity transmitted from the joint control CPU 160. Note that since something similar to a typical motor-driving driver IC may be used as the motor driver unit 170, a detailed description is omitted herein.

The actuator 180 causes the joint unit 130 to drive at a certain angle and speed by being driven in accordance with a certain control quantity by the joint control CPU 160. The actuator 180 may have the configuration illustrated in FIG. 13 discussed later, for example. For example, the actuator 180 includes a motor and a reduction gear. The rotational speed of the motor driven in accordance with a certain control quantity is reduced in speed by the reduction gear which has a certain speed reduction ratio, and as a result, a certain rotational driving force (torque) is generated. The generated torque is transmitted to subsequent members (such as the links and the front edge unit, for example), and these subsequent members drive.

Additionally, as discussed earlier, the actuator 180 includes onboard sensors that detect various physical quantities related to the driving of the actuator 180 itself. For example, the actuator 180 includes sensors such as a current sensor that detects the amount of current supplied to the motor, a temperature sensor that detects the temperature of the motor, an angle sensor that detects the rotational angle of the motor and the rotational angle of the output shaft of the reduction gear, and a torque sensor that detects the torque at the output shaft of the reduction gear. These sensors correspond to the joint state detecting unit 132 illustrated in FIG. 1, for example. The detected values from these sensors are provided to the joint control CPU 160 and the communication unit 150, and are used in the drive control of the actuator 180 and the detection of a malfunction of the joint unit 130.

(Driving of Actuator)

Figure 3:
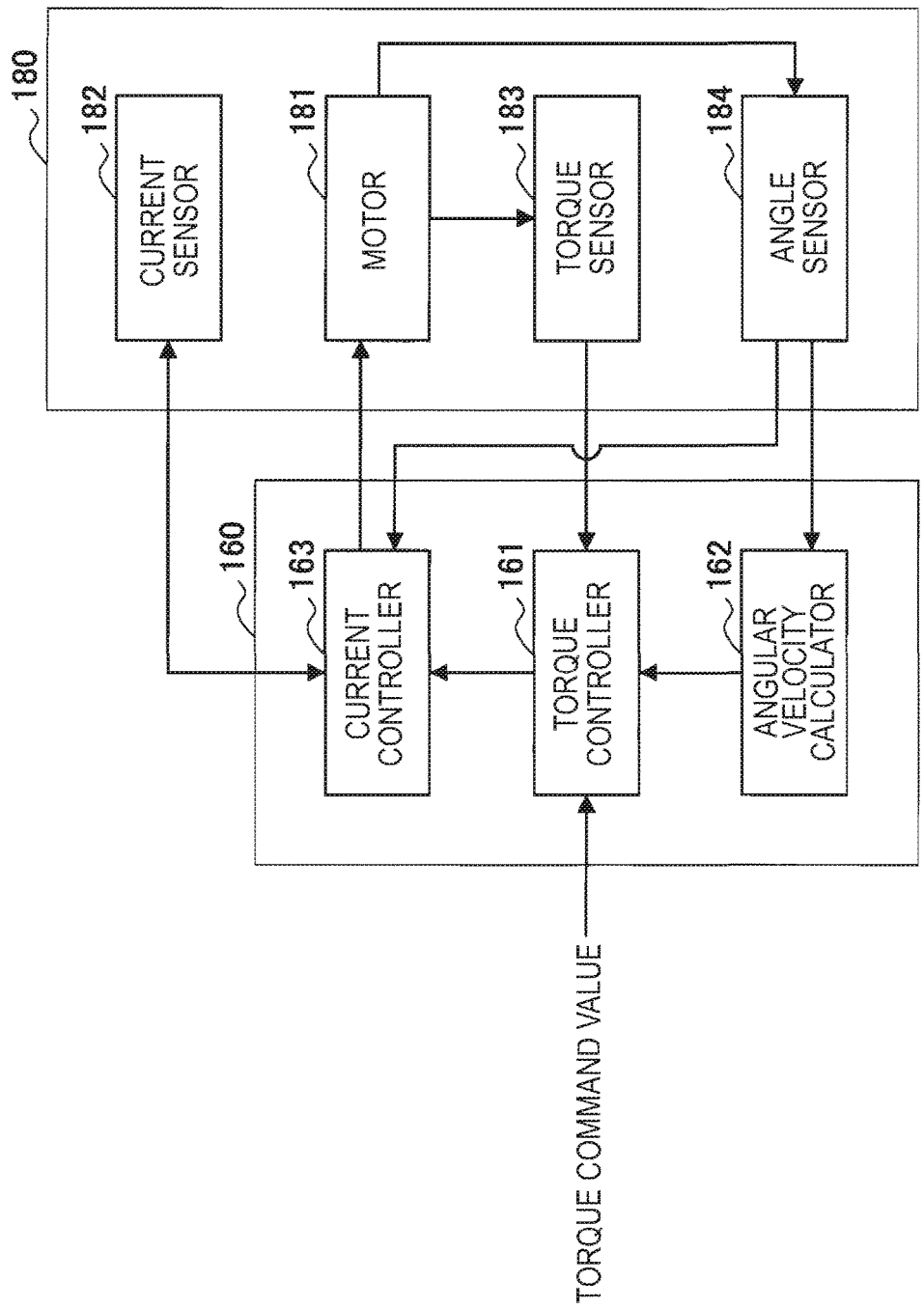
FIG. 3 is an explanatory diagram for explaining the driving of an actuator based on a torque command value.
Figure 4:
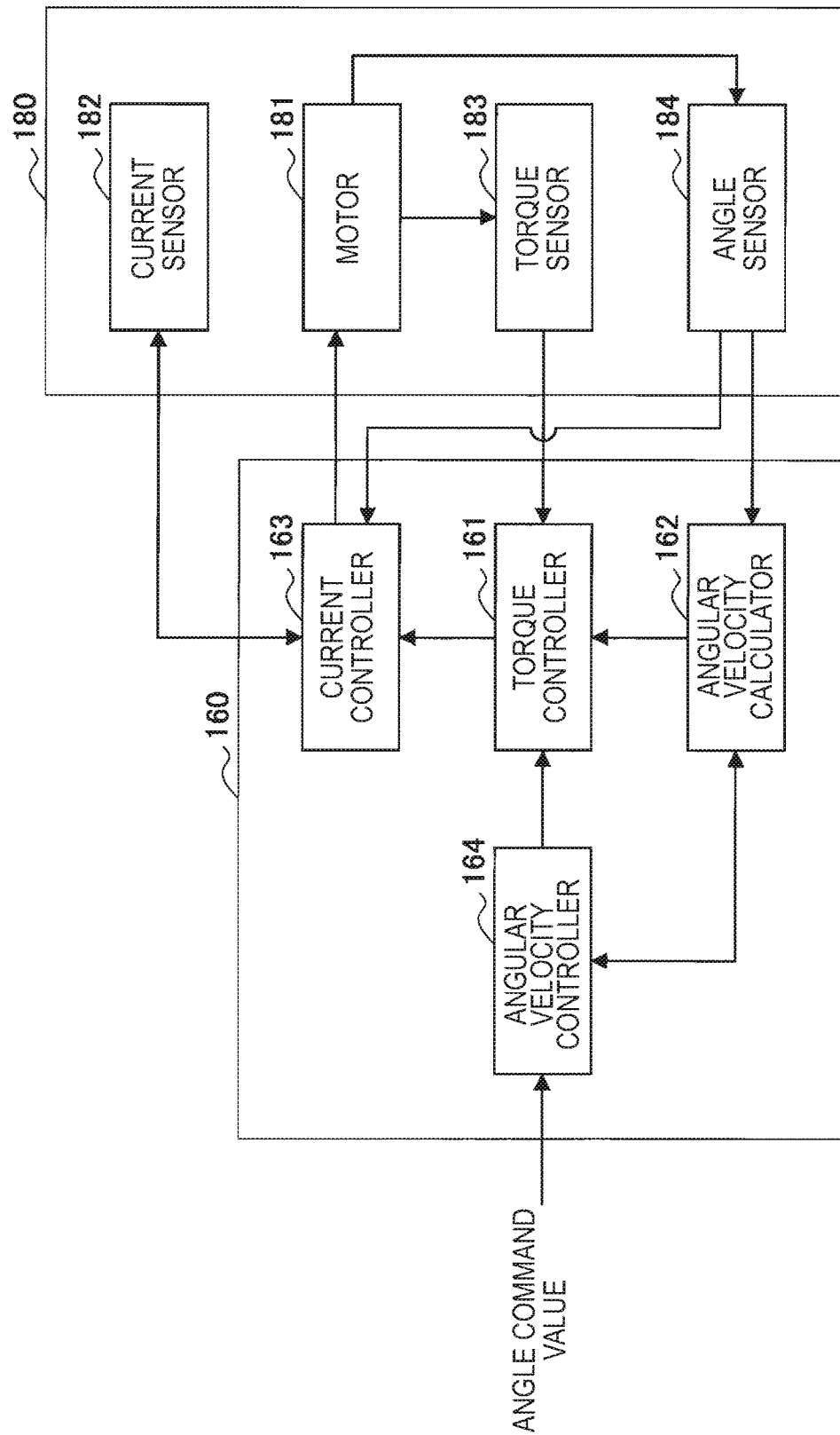
FIG. 4 is an explanatory diagram for explaining the driving of an actuator based on an angular velocity command value.
Figure 5:
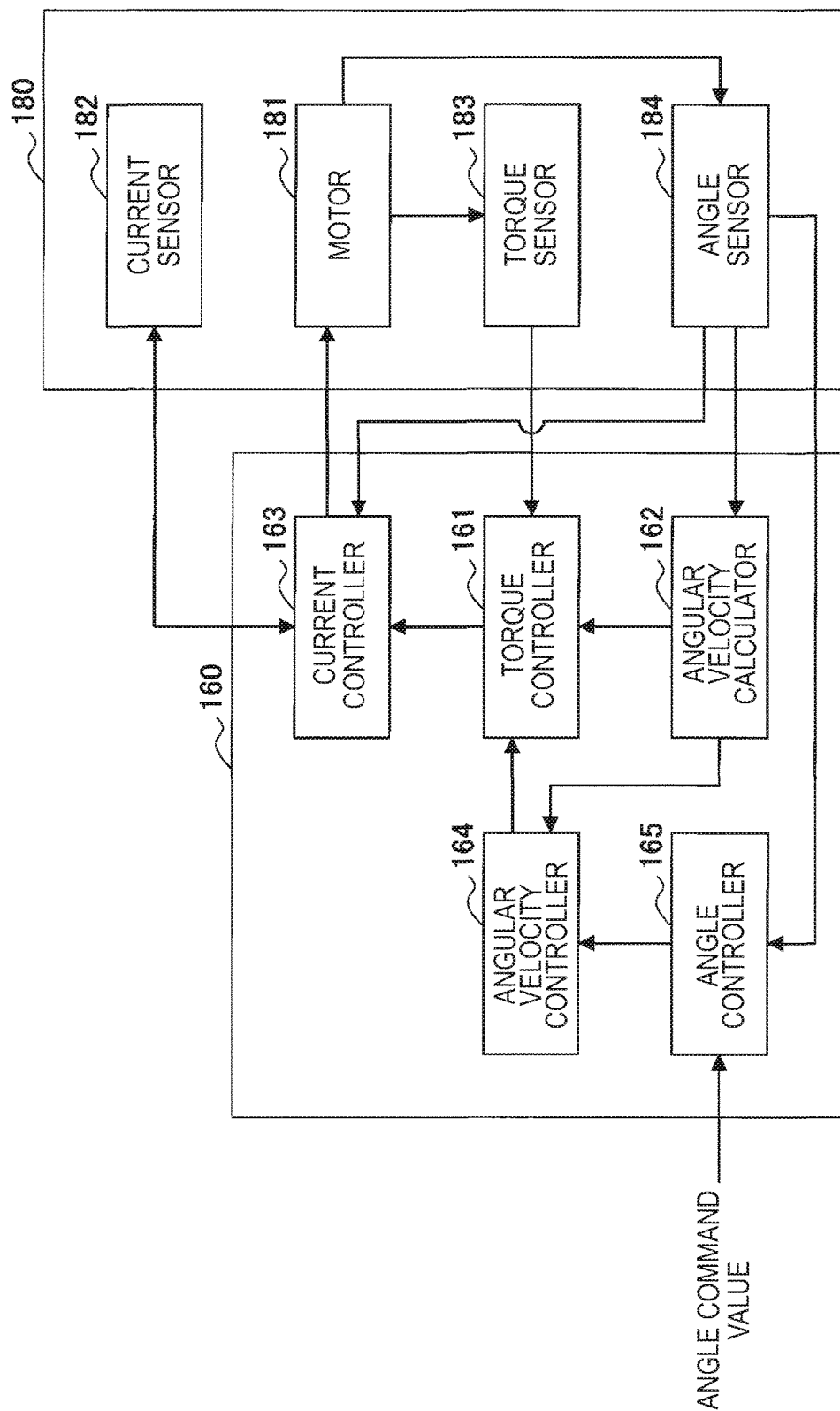
FIG. 5 is an explanatory diagram for explaining the driving of an actuator based on an angle command value.

At this point, configurations for controlling the driving of the actuator 180 by the joint control CPU 160 will be described in detail with reference to FIGS. 3 to 5. In FIGS. 3 to 5, configurations for driving the actuator 180 by the joint control CPU 160 discussed earlier (for example, configurations corresponding to the drive control unit 111 illustrated in FIG. 1) is illustrated in detail, while in addition, the exchange of information between the joint control CPU 160 and the actuator 180 when driving the actuator 180 is also illustrated.

The joint control CPU 160 causes each joint unit 130 to drive based on the control quantity computed by the control device 20 illustrated in FIG. 1. In the present embodiment, the control quantity may be any of a command value expressed as torque (torque command value), a command value expressed as angular velocity (angular velocity command value), and a command value expressed as an angle (angle command value). FIG. 3 is an explanatory diagram for explaining the driving of the actuator 180 based on a torque command value. Also, FIG. 4 is an explanatory diagram for explaining the driving of the actuator 180 based on an angular velocity command value. Also, FIG. 5 is an explanatory diagram for explaining the driving of the actuator 180 based on an angle command value.

First, the driving of the actuator 180 based on a torque command value will be described with reference to FIG. 3. As illustrated in FIG. 3, when a torque command value is given to the joint control CPU 160 as the control quantity, the torque command value is input into a torque controller 161 of the joint control CPU 160. At this point, the torque of the output shaft of a motor 181 of the actuator 180 is detected by a torque sensor 183, and the rotational angle of the output shaft of the motor 181 is detected by an angle sensor 184. Note that, although omitted from illustration in FIG. 3, in actuality, the torque sensor 183 and the angle sensor 184 detect the torque and the rotational angle of the output shaft through the reduction gear of the motor 181. The torque controller 161 may be provided with the torque detection value detected by the torque sensor 183.

In addition, the rotational angle detection value detected by the angle sensor 184 is provided to an angular velocity calculator 162 of the joint control CPU 160. The angular velocity calculator 162 computes the rotational angular velocity at the output shaft of the motor based on the rotational angle detection value, and provides the computed rotational angular velocity to the torque controller 161. The torque controller 161 is able to compute the rotational angular acceleration, or in other words the torque, based on the rotational angular velocity.

In this way, the torque controller 161 may be provided with a torque command value, as well as an actual torque measurement value based on a torque detection value detected by the torque sensor 183 and/or a rotational angle detection value detected by the angle sensor 184. Consequently, the torque controller 161 detects the torque control value based on the difference between the torque command value and the torque measurement value, and provides the torque control value to a current controller 163. The current controller 163 computes an amount of current (current control value) for realizing the torque control value, and drives the motor 181 with the current control value. Additionally, the current controller 163 may also be provided with the angle detection value detected by the angle sensor 184, and the current controller 163 may also compute a current control value for realizing the torque control value on the additional basis of the angle detection value. Note that, although omitted from illustration in FIG. 3, in actuality, a current corresponding to the current control value is generated by the motor driver unit 170 illustrated in FIG. 2, for example, and by supplying this current to the motor 181, the motor 181 may be driven.

According to the procedure described above, the driving of the actuator 180 based on a torque command value is realized. Note that the current value corresponding to the output of the current controller 163 (or the output of the motor driver unit 170) is continuously monitored by a current sensor 182 of the actuator 180, and if a current divergent from the intended current control value is detected, for example, the divergence is fed back to the current controller 163.

Next, the driving of the actuator 180 based on an angular velocity command value will be described with reference to FIG. 4. As illustrated in FIG. 4, when an angular velocity command value is given to the joint control CPU 160 as the control quantity, the angular velocity command value is input into an angular velocity controller 164 of the joint control CPU 160. Note that since the configuration illustrated in FIG. 4 corresponds to the configuration illustrated in FIG. 3 with the addition of the angular velocity controller 164, detailed description will be reduced or omitted for duplicate items.

In the configuration illustrated in FIG. 4, the rotational angular velocity at the output shaft of the motor is computed by the angular velocity calculator 162 based on the rotational angle detection value detected by the angle sensor 184, and the computed rotational angular velocity is provided to the angular velocity controller 164. Subsequently, the angular velocity controller 164 computes an angular velocity control value based on the difference between the angular velocity command value and the rotational angular velocity computed by the angular velocity calculator 162, and provides the angular velocity control value to the torque controller 161. The process thereafter may be similar to the configuration illustrated in FIG. 3. The torque controller 161 computes a torque control value based on the angular velocity control value and the actual torque measurement value based on the torque detection value detected by the torque sensor 183 and/or the rotational angle detection value detected by the angle sensor 184. Subsequently, a current control value is computed based on the torque control value and the motor 181 is driven by the current controller 163. According to the procedure described above, the driving of the actuator 180 based on an angular velocity command value is realized.

Next, the driving of the actuator 180 based on an angle command value will be described with reference to FIG. 5. As illustrated in FIG. 5, when an angle command value is given to the joint control CPU 160 as the control quantity, the angle command value is input into an angle controller 165 of the joint control CPU 160. Note that since the configuration illustrated in FIG. 5 corresponds to the configuration illustrated in FIG. 4 with the addition of the angle controller 165, detailed description will be reduced or omitted for duplicate items.

In the configuration illustrated in FIG. 5, the rotational angle detection value detected by the angle sensor 184 is provided to the angle controller 165. Subsequently, the angle controller 165 computes an angle control value based on the difference between the angle command value and the rotational angle detection value, and provides the angle control value to the angular velocity controller 164. The process thereafter may be similar to the configuration illustrated in FIG. 4. The angular velocity controller 164 is able to compute an angular velocity control value based on the difference between the angle control value provided by the angle controller 165, and the rotational angular velocity at the output shaft of the motor computed by the angular velocity calculator 162 based on the rotational angle detection value detected by the angle sensor 184. Subsequently, the torque controller 161 computes a torque control value based on the angular velocity control value and the actual torque measurement value based on the torque detection value detected by the torque sensor 183 and/or the rotational angle detection value detected by the angle sensor 184. Furthermore, a current control value is computed based on the torque control value and the motor 181 is driven by the current controller 163. According to the procedure described above, the driving of the actuator 180 based on an angle command value is realized.

The above thus describes configurations for controlling the driving of the actuator 180 by the joint control CPU 160 with reference to FIGS. 3 to 5. As described above, in the present embodiment, the control quantity for driving each joint unit 130 calculated by the control device 20 illustrated in FIG. 1 may be a torque command value, an angular velocity command value, or an angle command value. Regardless of which physical quantity is used to express the command value, by appropriately configuring the joint control CPU 160 as illustrated in FIGS. 3 to 5, for example, it becomes possible to drive the motor 181 in accordance with the command value.

(Configuration of Sensors in Actuator)

Figure 6:
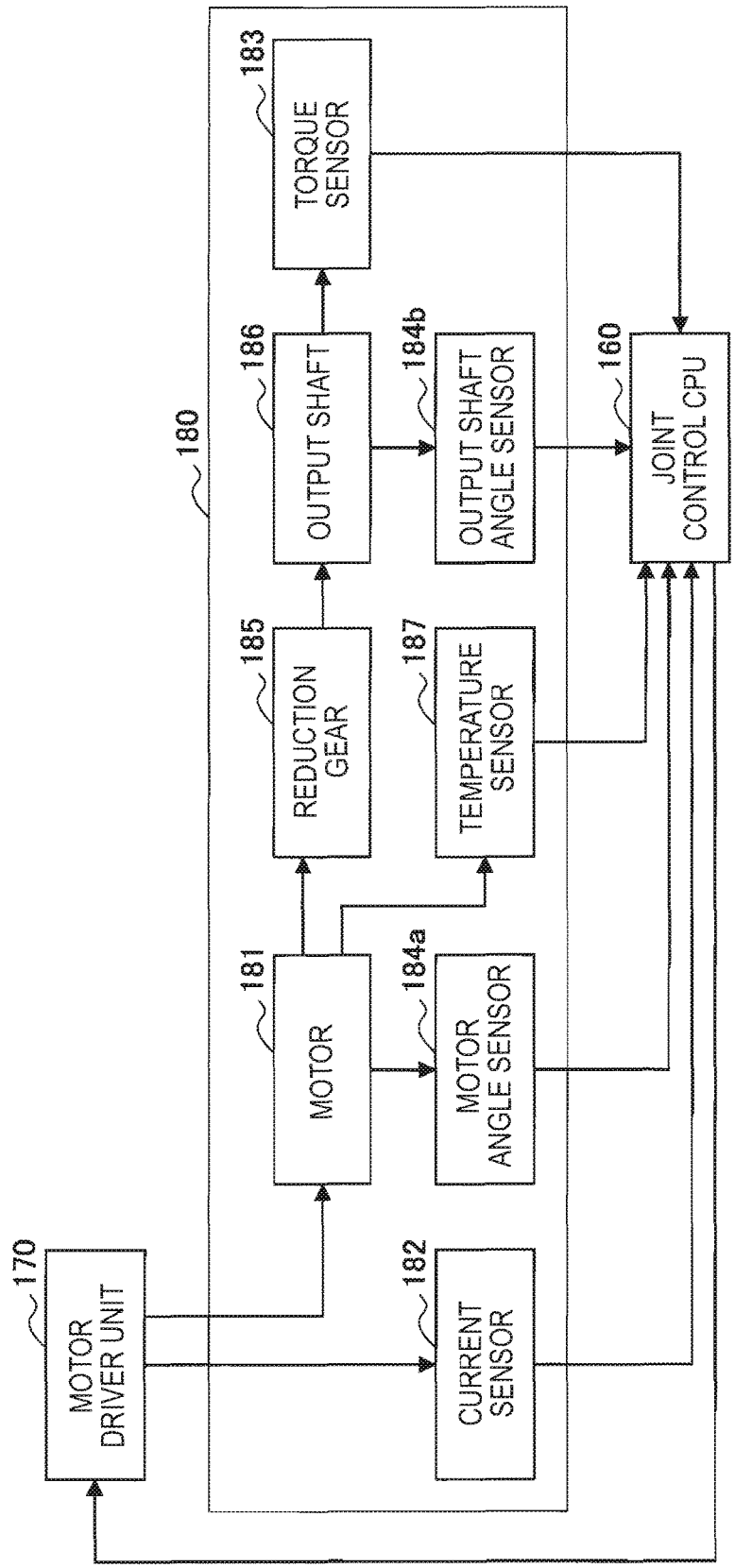
FIG. 6 is a block diagram illustrating an example configuration of sensors installed onboard an actuator.

As discussed above, in the present embodiment, various sensors are installed onboard the actuator 180. At this point, a configuration of the sensors installed onboard the actuator 180 will be described with reference to FIG. 6. FIG. 6 is a block diagram illustrating an example configuration of sensors installed onboard the actuator 180.

Referring to FIG. 6, the actuator 180 includes a motor 181, a reduction gear 185, a current sensor 182, a torque sensor 183, a motor angle sensor 184a, an output shaft angle sensor 184b, and a temperature sensor 187. Note that in FIG. 6, for the sake of explanation, the components of the actuator 180 are illustrated together with the motor driver unit 170 and the joint control CPU 160.

As discussed earlier, the motor 181 is driven under control from the joint control CPU 160 by being supplied with a certain current from the motor driver unit 170. In the actuator 180, the amount of current supplied to the motor 181 by the motor driver unit 170 is detected by the current sensor 182. In addition, the rotational angle of the motor 181 while driving is detected by the motor angle sensor 184a, and the temperature of the motor 181 while driving is detected by the temperature sensor 187.

The reduction gear 185 is joined to the rotating shaft of the motor 181, and as a result of the rotational speed of the motor 181 being reduced by a certain reduction ratio, a certain torque is generated. This torque is transmitted to subsequent members, thereby causing the joint unit 130 to drive. In the actuator 180, the torque sensor 183 and the output shaft angle sensor 184b are provided on an output shaft 186 that transmits torque from the reduction gear 185 to the subsequent members. The torque of the output shaft 186 (that is, the generated torque generated by the actuator 180) is detected by the torque sensor 183, and the rotational angle of the output shaft 186 is detected by the output shaft angle sensor 184b. Note that although FIGS. 3 to 5 illustrate one representative angle sensor 184, but in the present embodiment, as illustrated in FIG. 6, angle sensors that detect rotational speed (the motor angle sensor 184a and the output shaft angle sensor 184b) may also be provided on the motor 181 and the output shaft 186, respectively.

In the present embodiment, while the actuator 180 is driving, detection values from the current sensor 182, the temperature sensor 187, the torque sensor 183, the motor angle sensor 184a, and the output shaft angle sensor 184b are continually provided to the joint control CPU 160. As described with reference to FIGS. 3 to 5, the joint control CPU 160 is able to cause the actuator 180 to drive based on these detection values. Also, although omitted from illustration in FIG. 6, the detection values from these sensors may also be transmitted to the control device 20 via the communication unit 150. In the control device 20, a malfunction of the joint unit 130 is detected based on these detection values.

The above thus describes a configuration of the sensors installed onboard the actuator 180 with reference to FIG. 6. Note that in the present embodiment, the specific configurations of the current sensor 182, the temperature sensor 187, the torque sensor 183, the motor angle sensor 184a, and the output shaft angle sensor 184b are not limited to specific configurations, and any of various known sensors may be used as these sensors. For example, the current sensor 182 may be a sensor that detects current based on the voltage drop across a resistor, or a sensor that detects current based on changes in a magnetic field according to a Hall effect sensor. As another example, the temperature sensor 187 may be a sensor that utilizes a thermocouple, or a sensor that utilizes a resistance thermometer. As another example, the torque sensor 183 may be a sensor that uses any of various strain sensors. As another example, the motor angle sensor 184a and the output shaft angle sensor 184b may be any of various rotary encoders.

<4. Processing Procedure of Robot Arm Control Method>

Figure 7:
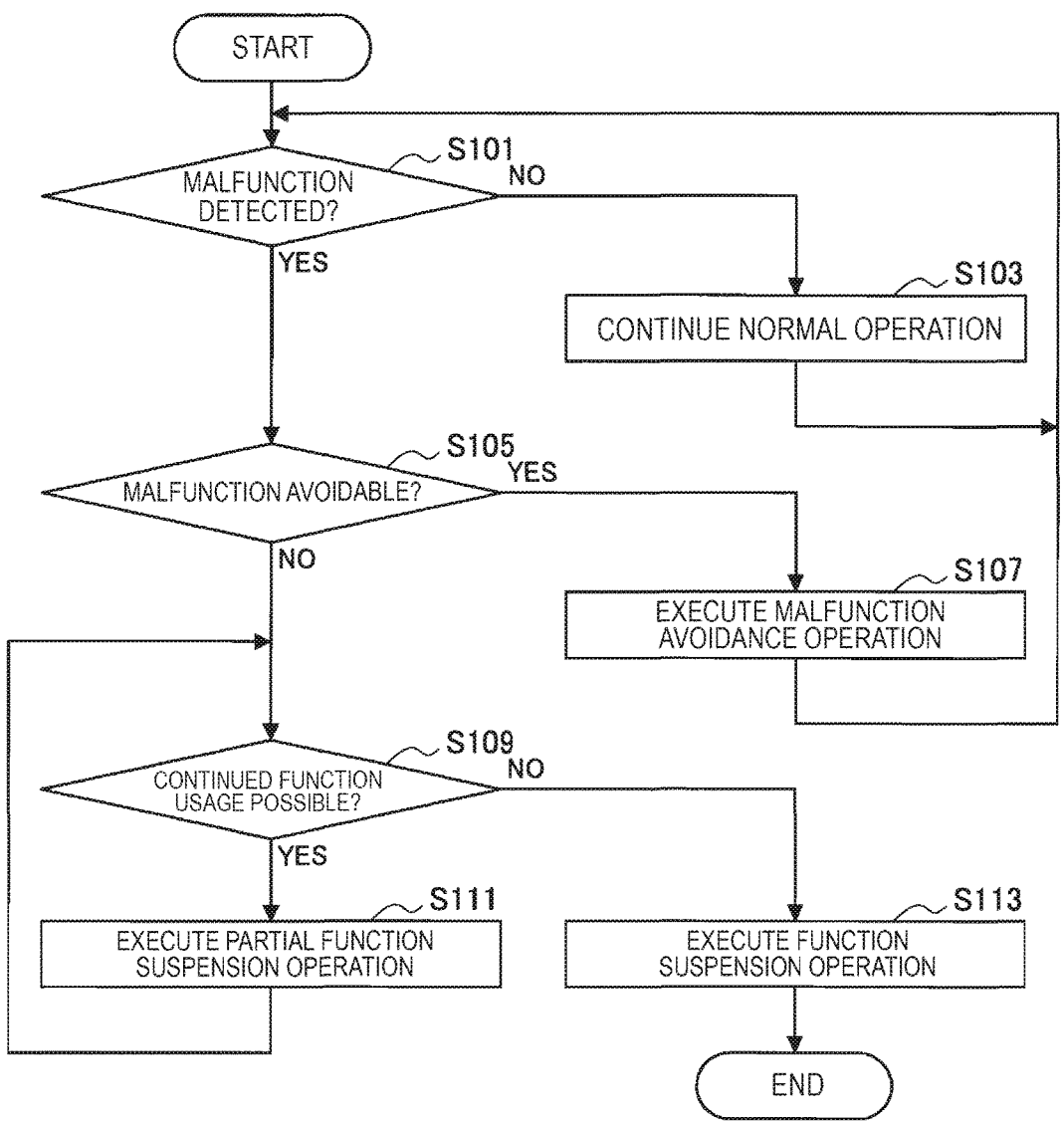
FIG. 7 is a flowchart illustrating an example of a processing procedure of a robot arm control method according to an embodiment.

Next, a processing procedure of a robot arm control method according to the present embodiment will be described with reference to FIG. 7. FIG. 7 is a flowchart illustrating an example of a processing procedure of a robot arm control method according to the present embodiment. Note that each process illustrated in FIG. 7 may be realize by the functional configuration of the robot arm control system 2 illustrated in FIG. 1, for example. In addition, the robot arm control method described herein relates to a series of processing steps when a malfunction is detected in the driving of the arm unit 120. A more detailed control method when controlling the driving of the arm unit 120, such as the computation of the control quantity, for example, will be discussed later with reference to FIG. 10.

Referring to FIG. 7, in the robot arm control method according to the present embodiment, first, it is determined whether or not a malfunction in the joint unit 130 was detected during the driving of the arm unit 120 (step S101). In the process illustrated in step S101, a malfunction detection process may be conducted on each joint unit 130 constituting the arm unit 120, and the detection of whether or not a malfunction is occurring in any joint unit 130 may also be performed. The process illustrated in step S101 may be a process in which a malfunction of the joint unit 130 is detected by the malfunction detecting unit 260 illustrated in FIG. 1, based on various information for detecting a malfunction of the joint unit 130, for example.

If a malfunction is not detected in step S101, normal operation is continued as-is in the arm unit 120 (step S103). Herein, normal operation refers to a state in which the driving of the arm unit 120 is controlled normally. For example, operations such as the power assist operation and the pivot operation described in (6-2. Specific example of purpose of motion) below may be conducted, and various medical procedures may be performed on the patient by the front edge unit 145.

In the power assist operation, the joint unit 130 drives so as to cancel out gravity acting on the arm unit 120, while in addition, a purpose of motion is set so that the joint unit 130 drives to support the movement of the arm unit 120 in the direction of a force additionally exerted from outside, and the driving of the joint unit 130 is controlled based on the purpose of motion. By performing such control, the surgeon is able to operate the arm unit 120 as though the arm unit 120 is weightless.

Additionally, in the pivot operation, a constraint condition is set so that, in a state in which the orientation of the front edge unit 145 is locked to a certain point in space, the front edge unit 145 moves over the surface of a cone whose apex is the certain point, and the driving of the joint unit 130 is controlled based on the constraint condition. For example, by providing an imaging device as the front edge unit 145 and performing such control, it becomes possible to observe the same point (for example, the surgical site) from different directions and different distances. Also, in the pivot operation, the distance between a certain point in space that serves as the center of the pivot operation (the pivot center point) and the front edge unit 145 may be kept constant. Consequently, the driving of the arm unit 120 is controlled so as to move over a hemisphere centered on the pivot center point in a state in which the front edge unit 145 (an imaging device, for example) is pointed at the pivot center point, thereby enabling easy observation of a certain point from any direction. Additionally, the power assist operation and the pivot operation may also be used in combination.

If a malfunction is detected in step S101, the flow proceeds to step S105. In step S105, according to the type of the detected malfunction, it is determined whether or not the malfunction is avoidable with a malfunction avoidance operation.

In step S105, if it is determined that the malfunction is avoidable, an malfunction avoidance operation is executed (step S107). In the malfunction avoidance operation, the driving of the joint unit 130 is controlled in a state in which a certain restriction is imposed on the motion of the arm unit 120, and the arm unit 120 is driven to avoid the malfunction. The certain restriction may be, for example, not generating torque of a certain value or greater in each joint unit 130, not rotating each joint unit 130 past a certain angle, or the like.

In step S105, if it is determined that the malfunction is not avoidable, the flow proceeds to step S109. In step S109, according to the type of the detected malfunction, it is determined whether or not the malfunction allows for continued usage of the functions of the arm unit 120.

In step S109, if it is determined that continued usage of the functions of the arm unit 120 is possible, a partial function suspension operation is executed (step S111). In the partial function suspension operation, the driving of the joint units 130 other than the joint unit 130 where the malfunction was detected is controlled, and the arm unit 120 is driven in a state of lowered degrees of freedom compared to the original degrees of freedom.

In step S109, if it is determined that continued usage of the functions of the arm unit 120 is not possible, the flow proceeds to step S113. In step S113, a function suspension operation is executed. In the function suspension operation, the functions of the arm unit 120 are suspended safely so that the arm unit 120 does not move unexpectedly and injure the surgeon or the patient. For example, in the function suspension operation, the motion of all joint units 130 constituting the arm unit 120 is locked.

The above thus describes a processing procedure of a robot arm control method according to the present embodiment with reference to FIG. 7. As described above, in the present embodiment, when a malfunction in the joint unit 130 is detected, an operation from among a malfunction avoidance operation, a partial function suspension operation, and a function suspension operation is selected to be executed according to the type of malfunction. If the malfunction avoidance operation is executed, the driving of the arm unit 120 is continued in a state in which the malfunction is avoided. Meanwhile, if the partial function suspension operation is executed, the driving of the arm unit 120 is continued in a state in which partial functions of the arm unit 120 are suspended. Consequently, even if a malfunction is detected, it is still possible to continue a medical procedure using the arm unit 120, and safety for the patient may be improved further. Also, in the case of detecting a malfunction for which continuing the driving control of the arm unit 120 by whole body cooperative control is difficult, the function suspension operation is executed, and the functions of the arm unit 120 are suspended safely so that the surgeon and the patient are not injured.

Note that the processes illustrated in steps S105 and S109 discussed above may be processes in which the operation condition setting unit 242 illustrated in FIG. 1, based on a malfunction of the joint unit 130 detected by the malfunction detecting unit 260, determines the type of the malfunction and the operation of the arm unit 120 according to the type of malfunction, for example. Also, the processes illustrated in steps S107 and S111 may be processes in which the operation condition setting unit 242 illustrated in FIG. 1 sets respective operation conditions for control quantities causing the arm unit 120 to perform a malfunction avoidance operation and a partial function suspension operation, and the drive control unit 111 controls the driving of each joint unit 130 based on the control quantities computed under the operation conditions by the whole body cooperative control unit 240 and the ideal joint control unit 250, for example. Also, the process illustrated in step S113 is a process in which the drive control unit 111 illustrated in FIG. 1 controls the driving for each joint unit 130 using position control, for example.

In addition, in FIG. 7, for the sake of explanation, the execution of an operation from among a malfunction avoidance operation, a partial function suspension operation, and a function suspension operation is illustrated as being selected in stages, as illustrated in steps S101, S105, and S109. However, the actual process may also not make determinations in stages in this way. For example, as described in <2. Functional configuration of robot arm control system> above, a table associating types of malfunctions with operations that may be executed when the corresponding malfunction occurs is created, and which operation to execute may be determined based on the table.

<5. Details of Each Process>

Next, from the processing procedure illustrated in FIG. 7, each of the malfunction detection process of step S101, the malfunction avoidance operation of step S107, the partial function suspension operation of step S111, and the function suspension operation of step S113 will be described in detail.

(5-1. Malfunction Detection Process)

First, the malfunction detection process according to the present embodiment will be described. As discussed earlier with reference to FIGS. 1 and 6, in the present embodiment, a malfunction of each joint unit 130 may be detected based on detection values from the various sensors provided in the actuator 180 (in other words, the state of the joint unit 130 detected by the joint state detecting unit 132). For example, the current sensor 182, the torque sensor 183, the motor angle sensor 184*a*, the output shaft angle sensor 184*b*, and the temperature sensor 187 are provided as these sensors.

Figure 8:
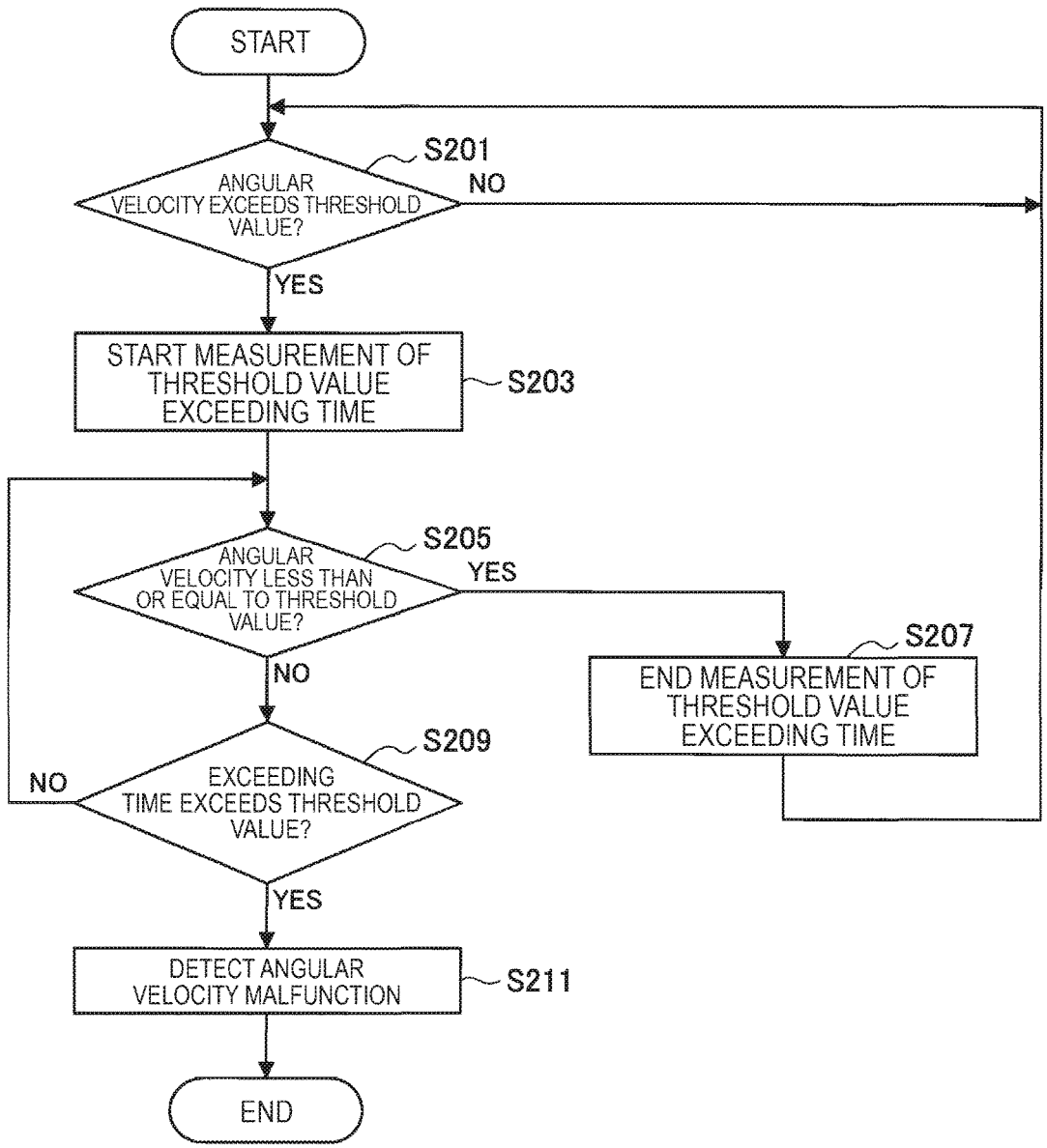
FIG. 8 is a flowchart illustrating an example of a processing procedure in a malfunction detection process based on angular velocity.

As an example of the malfunction detection process, FIG. 8 will be referenced to describe a processing procedure of a malfunction detection process based on the angular velocity of the motor 181 or the output shaft 186. FIG. 8 is a flowchart illustrating an example of a processing procedure in a malfunction detection process based on angular velocity. Note that the angular velocity of the motor 181 or the output shaft 186 may be computed by the angular velocity calculator 162 illustrated in FIGS. 3 to 6 based on a detection value of the rotational angle by the motor angle sensor 184*a* or the output shaft angle sensor 184*b*, for example. Also, each process illustrated in FIG. 8 may be executed by the malfunction detecting unit 260 illustrated in FIG. 1, for example.

Referring to FIG. 8, in the malfunction detection process according to the present embodiment, first, it is determined whether or not the detected angular velocity exceeds a certain threshold value (first threshold value) (step S201). For the first threshold value, a value that would not be detected as the angular velocity under normal conditions may be set appropriately based on information such as the internal model used for driving control of the arm unit 120. In addition, the detection of angular velocity may be conducted continually at certain timings. If it is determined that the detected angular velocity does not exceed the first threshold value, the detection of angular velocity at certain timings is continued unchanged. On the other hand, if it is determined that the detected angular velocity exceeds the first threshold value, the flow proceeds to step S203.

In step S203, measurement of the time that the detected angular velocity has exceeded the first threshold value (threshold value exceeding time) is started. The angular velocity is still detected continually during the measurement of the threshold value exceeding time, and it is determined continually whether or not the detected angular velocity is less than or equal to the first threshold value (step S205). In step S205, if it is determined that the detected angular velocity has become less than or equal to the first threshold value before the threshold value exceeding time exceeds a certain threshold value (second threshold value), it may be determined that the indication of an abnormal value greater than the first threshold value by the angular velocity is a temporary phenomenon. Consequently, the measurement of the threshold value exceeding time is ended (step S207), the flow returns to step S201, and the detection of angular velocity is continued.

On the other hand, in step S205, if it is determined that the detected angular velocity is not less than or equal to the first threshold value, it is determined whether or not the threshold value exceeding time exceeds the second threshold value (step S209). If it is determined that the threshold value exceeding time does not exceed the second threshold value, the flow returns to step S205, and the comparison of the detected angular velocity to the first threshold value as well as the comparison of the threshold value exceeding time to the second threshold value are repeated. In step S209, if it is determined that the threshold value exceeding time exceeds the second threshold value, this means that the time over which the angular velocity has indicated an abnormal value greater than the first threshold value has continued for a fixed time or more. Consequently, it is determined that the detection value of the angular velocity is abnormal (step S211), and it is determined that a malfunction is occurring in the joint unit 130.

The above thus describes, as an example of the malfunction detection process, a processing procedure of a malfunction detection process based on the angular velocity of the motor 181 or the output shaft 186 with reference to FIG. 8. Note that in FIG. 8, although a processing procedure for a process of detecting a malfunction based on the detection value of angular velocity is described as an example, it is possible to detect a malfunction according to a similar procedure for other detection values, such as the rotational angle, the angular acceleration, the torque, the current, and the temperature, for example. As described above, in the present embodiment, if it is determined that a time over which the detection value from each sensor exceeds a certain threshold value has continued for a fixed time or more, it may be determined that the joint unit 130 where the relevant detection value was detected has a malfunction.

In addition, in the present embodiment, a malfunction of the joint unit 130 may also be detected by a method other than the processing procedure described above. For example, the malfunction detecting unit 260 is able to detect a malfunction based on a method like the following.

For example, regarding angular acceleration, angular velocity, and torque, even if the time over which an abnormal value is detected does not exceed a fixed time, a malfunction may be detected at the instant that the detection value exceeds a certain threshold value. This is because in such a case, there is a risk that the arm unit 120 may be moving at an excessive speed, or excessive force may be imparted to the patient by the arm unit 120. In addition, strain gauges may be provided in the links of the arm unit 120, and a malfunction may be detected by also using detection values from the strain gauges, for example. This is because the detection value from such a strain gauge may serve as an indicator of pressing force imparted to an external object, such as the surgeon or the patient, due to contact with the arm unit 120. Note that if this type of malfunction is detected, a suitable malfunction avoidance operation may be conducted. In such a malfunction avoidance operation, a purpose of motion and/or a constraint condition are set as operation conditions so that the velocity or force becomes less than or equal to a certain value, for example, and the driving of the arm unit 120 is controlled so that excessive velocity and force are not produced.

As another example, a malfunction may also be detected by determining whether or not the driving control of the joint unit 130 is stable, based on the torque detection value from the torque sensor 183. Specifically, a fast Fourier transform (FFT) may be used to perform frequency analysis on the torque detection value, for example, and if an abnormal frequency component is detected from the result of the frequency analysis, a malfunction may be detected. This is because the case of detecting an abnormal frequency component from the torque detection value indicates that control is not stable and that there is a possibility of oscillation. If such a malfunction is detected, an operation condition may be set so that the computation of the control quantity is conducted with a lower gain, for example, and a malfunction avoidance operation by which the driving of the arm unit 120 is controlled in a more stable control system may be conducted. On the other hand, if control does not stabilize even after lowering the gain, a partial function suspension operation that drives the arm unit 120 with the joint units 130 other than the joint unit 130 where the malfunction was detected may be conducted.

As another example, a malfunction of the joint unit 130 may also be detected based on a detection value of the rotational angle of the motor 181 and/or the output shaft 186 by the motor angle sensor 184a and/or the output shaft angle sensor 184b. For example, the detection value from the motor angle sensor 184a and the detection value from the output shaft angle sensor 184b should exist in a proportional relationship through the reduction ratio of the reduction gear 185. Consequently, if the proportional relationship between the detection value from the motor angle sensor 184a and the detection value from the output shaft angle sensor 184b breaks down, there is a possibility of a failure in any of the motor 181, the reduction gear 185, the motor angle sensor 184a, and the output shaft angle sensor 184b. As another example, if the detection value from the motor angle sensor 184a does not change even though the current sensor 182 detects that a certain value of current is being supplied to the motor 181, there is a possibility of a failure in the motor 181 or the motor angle sensor 184a. Similarly, if the detection value from the output shaft angle sensor 184*b* does not change even though the current sensor 182 detects that a certain value of current is being supplied to the motor 181, there is a possibility of a failure in any of the motor 181, the reduction gear 185, and the output shaft angle sensor 184*b*. In this way, if a failure is detected in any of the motor 181, the reduction gear 185, the motor angle sensor 184*a*, and the output shaft angle sensor 184*b* as a malfunction of the joint unit 130, it is considered to be difficult to perform desire driving control on the joint unit 130. Consequently, if such a malfunction is detected, a partial function suspension operation that drives the arm unit 120 with the joint units 130 other than the joint unit 130 where the malfunction was detected may be conducted.

As another example, a malfunction of the joint unit 130 may also be detected based on a detection value of the current supplied to the motor 181 by the current sensor 182. For example, if excess current is detected by the current sensor 182, there is a risk of a failure (short) in the motor 181, or if excess current flows because control is unstable and the excess current is continually applied, there is a risk of the motor 181 failing. In addition, if a large divergence is produced between the amount of current given as the command value and the current detection value by the current sensor 182, a failure in the motor driver unit 170 may be suspected. If a malfunction based on such a current detection value is detected as the malfunction of the joint unit 130, it is difficult to drive the motor 181 correctly, and thus it is considered difficult to perform desired driving control on the joint unit 130. Consequently, if such a malfunction is detected, a partial function suspension operation that drives the arm unit 120 with the joint units 130 other than the joint unit 130 where the malfunction was detected may be conducted.

As another example, a malfunction of the joint unit 130 may also be detected based on a detection value of the temperature of the motor 181 by the temperature sensor 187. For example, if the ambient temperature of the motor 181 is significantly higher compared to the other structural elements around the motor driver unit 170 or the like, there is a possibility that the temperature sensor 187 or the motor 181 is failing. If a malfunction based on such a temperature detection value is detected as the malfunction of the joint unit 130, there is a possibility of the motor 181 performing an abnormal operation, and thus from a safety perspective, it is desirable to suspend the driving of the joint unit 130 where the malfunction was detected. Consequently, if such a malfunction is detected, a partial function suspension operation that drives the arm unit 120 with the joint units 130 other than the joint unit 130 where the malfunction was detected may be conducted.

As another example, a malfunction of the joint unit 130 may also be detected based on the communication state of the communication unit 150. For example, if communication by the communication unit 150 is suspended for some reason, the joint unit 130 becomes unable to receive information about the control quantity computed by the control device 20, and thus driving control based on whole body cooperative control can no longer be performed on the joint unit 130. Consequently, if such a malfunction is detected, a function suspension operation that suspends operation of the arm unit 120 may be conducted.

In addition, in the present embodiment, the joint unit 130 may also be provided with a brake mechanism that acts to suspend the driving of the motor 181. The brake mechanism may be a mechanism that controllably locks the rotational angle of the motor 181, a mechanism that mechanically suspends the driving of the motor 181, or a mechanism that cuts off the supply of current from the motor driver unit 170 to the motor 181 via an electric circuit. For example, if the detection value from any of the motor angle sensor 184*a* and the output shaft angle sensor 184*b* changes even though the brake mechanism is engaged, there is a possibility that the brake mechanism is failing, and a situation is occurring in which the brake is not applied. Conversely, if the brake mechanism is released, and the detection value from any of the motor angle sensor 184*a* and the output shaft angle sensor 184*b* does not change even though an external force is applied in an attempt to move the joint unit 130, there is a possibility that the brake mechanism is failing, and a situation is occurring in which the brake is applied unintentionally. If such a failure of the brake mechanism is detected as the malfunction of the joint unit 130, there is a risk that the arm unit 120 may move unexpectedly when driven, and the surgeon and the patient may be exposed to danger. Consequently, if such a malfunction related to the brake mechanism is detected, a function suspension operation that suspends operation of the arm unit 120 may be conducted.

The above thus illustrates examples of types of malfunctions that may be detected in the present embodiment. However, the malfunction detection process according to the present embodiment is not limited to the examples discussed above, and other malfunctions may also be detected based on various information for detecting a malfunction (such as information about detection values from the sensors of the actuator 180 (the state of the joint unit 130 detected by the joint state detecting unit 132), information about driving control of the joint unit 130, information about a command value transmitted to the joint unit 130, and information about the communication state of the joint unit 130, for example). In addition, although the above describes operations that the arm unit 120 may switch to when respective malfunctions are detected, the switch to these operations are merely exemplary, and the correspondence relationship between each malfunction and operation is not necessarily limited to the above-described. Which operation to switch to when each malfunction is detected may be set appropriately according to various conditions related to control, such as the overall configuration of the arm unit 120 and the internal model used for driving control of the arm unit 120.

The above thus describes the malfunction detection process according to the present embodiment. As described above, according to the present embodiment, a malfunction is detected for each joint unit 130 based on various information for detecting a malfunction. Consequently, it is possible to identify the joint unit 130 where a malfunction is occurring, and execute an operation using the joint units 130 other than the joint unit 130 where the malfunction was detected, such as a partial function suspension operation, for example. Also, in the present embodiment, which structural member of the joint unit 130 is failing may be detected according to what kind of information serves as the basis for detecting the malfunction. Consequently, it becomes possible to select the operation to be performed by the arm unit 120 according to the structural member where the failure is detected, for example. For example, if the structural member where the failure is detected is a required member for conducting driving control of the joint unit 130, or an important member for ensuring safety, it is preferable to switch to the function suspension operation. In this way, in the present embodiment, since it is possible to detect even which structural member is failing for each joint unit 130, it becomes possible to determine the type of malfunction in detail, and appropriately select the operation to be performed by the arm unit 120.

(5-2. Malfunction Avoidance Operation)

Next, the malfunction avoidance operation according to the present embodiment will be described. In the malfunction avoidance operation, the driving of the joint unit 130 is controlled in a state in which a certain restriction is imposed on the motion of the arm unit 120, and the arm unit 120 is driven to avoid the malfunction. The certain restriction may be a restriction by which the arm unit 120 drives so as to avoid a detected malfunction. For example, the certain restriction may be a numerical restriction on the torque in each joint unit 130 of the arm unit 120 (generated torque and external torque), or the rotational angle, the rotational angular velocity, and the rotational angular acceleration of each joint unit 130. Consequently, a collision of the arm unit 120 or the front edge unit 145 into the surgeon or the patient with excessive force or velocity is avoided.

Figure 9:
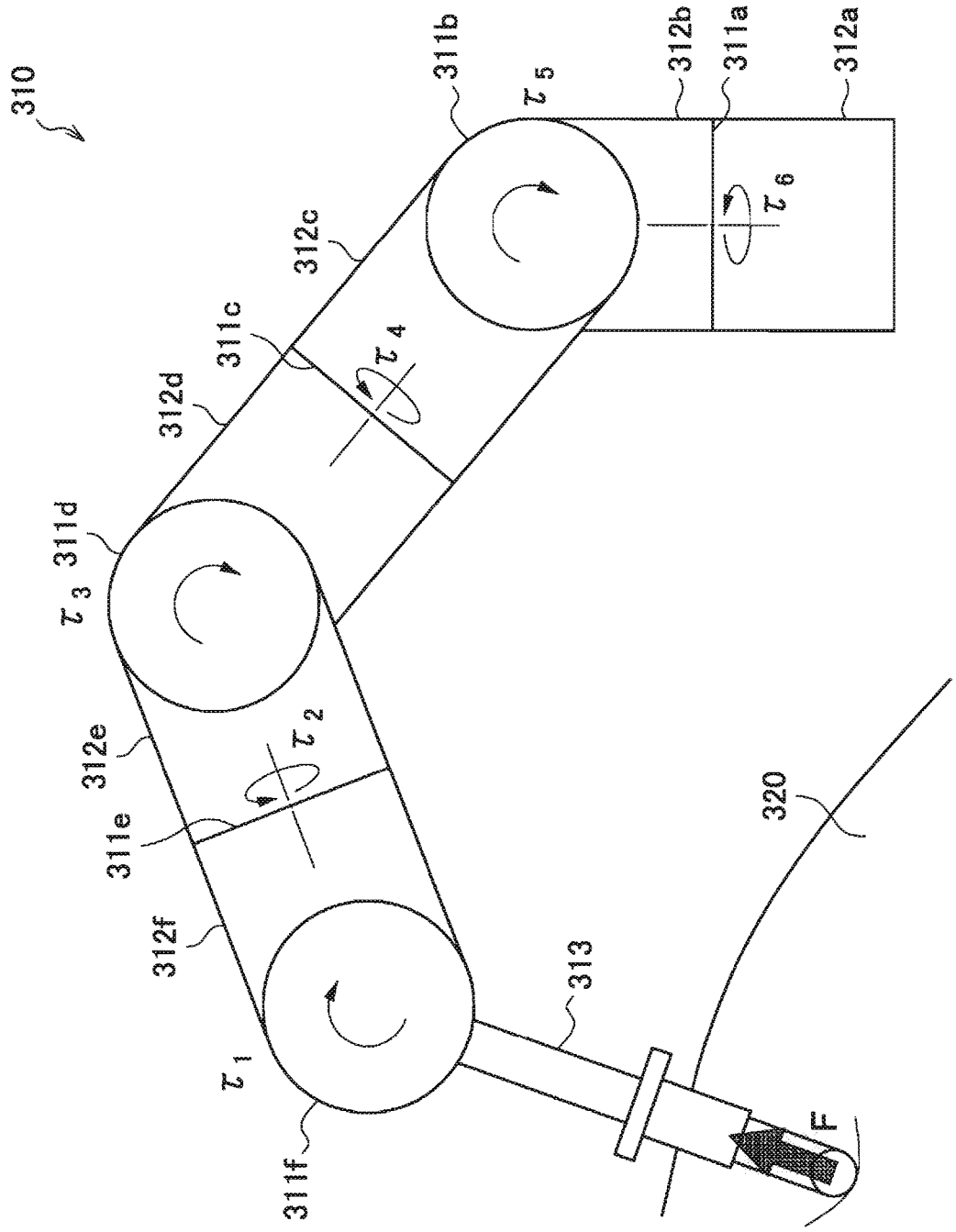
FIG. 9 is an explanatory diagram for explaining a malfunction avoidance operation based on torque in a joint unit.
Figure 10:
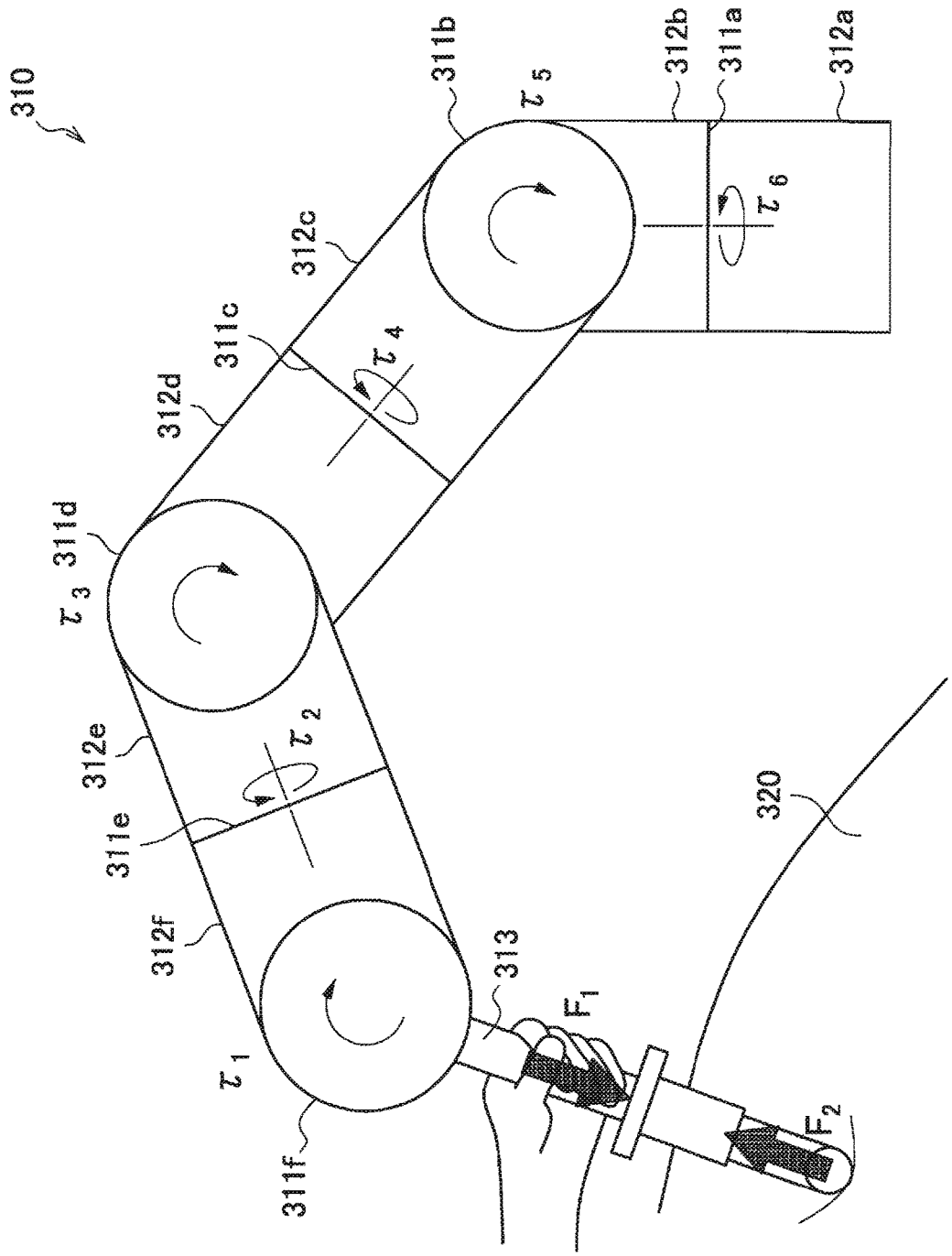
FIG. 10 is an explanatory diagram for explaining a malfunction avoidance operation based on torque in a joint unit.

As an example of the malfunction avoidance operation, FIGS. 9 and 10 will be referenced to describe a malfunction avoidance operation based on torque in the joint unit 130. FIGS. 9 and 10 are explanatory diagrams for explaining a malfunction avoidance operation based on torque in the joint unit 130.

FIG. 9 illustrates how a certain treatment is performed on a patient 320 by an arm unit 310 of a robot arm apparatus. Referring to FIG. 9, the arm unit 310 is made up of multiple links 312*a* to 312*f* joined to each other by multiple joint units 311*a* to 311*f*. The arm unit 310 may be driven by controlling the rotational driving of each of the joint units 311*a* to 311*f*. A front edge unit 313 is provided on the front edge of the arm unit 310, and various treatments are performed on the patient 320 by the front edge unit 313. In the example illustrated in FIG. 9, the front edge unit 313 is an endoscope which may be inserted into a body cavity of the patient 320 to observe the state of an affected part inside the body cavity or perform various treatments on the affected part.

At this point, as illustrated in FIG. 9, suppose that due to an incorrect operation by the surgeon, for example, the front edge unit 313 contacts the body of the patient 320 (such as an organ, for example). Because of this contact, a reaction force F from the body of the patient 320 is imposed on the front edge unit 313 (in other words, a pressing force F on the front edge unit 313 is produced), while in addition, due to the influence of the reaction F being imposed, torques $\tau_1$ to $\tau_6$ are imposed on the joint units 311*a* to 311*f*, respectively. Meanwhile, in the present embodiment, a torque sensor is provided in each of the joint units 311*a* to 311*f*, and the external torque imposed on each of the joint units 311*a* to 311*f* may be detected by the torque sensor.

In the present embodiment, a malfunction is detected when a torque equal to or greater than a certain threshold value is detected by the torque sensor, for example, and as the malfunction avoidance operation, the driving of each of the joint units 311*a* to 311*f* may be controlled so that a torque greater than the threshold value is not detected in each of the joint units 311*a* to 311*f*. Specifically, for the pressing force F by the front edge unit 313, a value that would not endanger the patient 320 is set as the purpose of motion. Consequently, a force equal to or greater than the set value is not produced in the front edge unit 313. At this point, with whole body cooperative control, the external force F is computed based on the torques $\tau_1$ to $\tau_6$ of each of the joint units 311*a* to 311*f*. Consequently, by setting the purpose of motion as above, the torques $\tau_1$ to $\tau_6$ of each of the joint units 311*a* to 311*f* are controlled so that the pressing force F by the front edge unit 313 does not become equal to or greater than the set value. Thus, in the present embodiment, a malfunction is detected when a torque value that could cause the pressing force F to become equal to or greater than the set value is detected as any of the torques $\tau_1$ to $\tau_6$, and a malfunction avoidance operation may be conducted by controlling the driving of each of the joint units 311*a* to 311*f* to prevent the generation of such a torque. By conducting such a malfunction avoidance operation, even if the front edge unit 313 contacts an organ or the like of the patient 320, the organ is not impacted with excessive force, and the medical procedure may be continued more safely.

In addition, when setting an upper limit value of the pressing force F, different values may be set for each direction in which the force acts. For example, by setting a smaller value as the upper limit value of the force acting in the operation direction of the arm unit 310, danger that may be produced with respect to the patient may be avoided more appropriately.

On the other hand, as illustrated in FIG. 10, in the present embodiment, a case in conceivable in which the arm unit 120 is moved in a state of the surgeon gripping the front edge unit 313. In this case, if it is supposed that the front edge unit 313 contacts the body of the patient 320 (such as an organ, for example), at the front edge unit 313, the reaction force $F_2$ from the body of the patient 320 and the pressing force $F_1$ by the surgeon may act in opposite directions. Thus, a situation may occur in which even though the front edge unit 313 is being pressed against the body of the patient 320 with excessive force, this state is not reflected in the torques $\tau_1$ to $\tau_6$ of each of the joint units 311*a* to 311*f*. In the present embodiment, to avoid such a situation, a strain sensor for detecting force (stress) may be provided at some part closer to the front edge than the part of the front edge unit 313 that the surgeon grips, for example. With the strain sensor, the reaction force $F_2$ from the body of the patient 320 (in other words, the pressing force $F_2$ by the front edge unit 313) may be measured directly. Alternatively, the strain sensor may be provided at the part of the front edge unit 313 gripped by the surgeon. With the strain sensor, the pressing force $F_1$ by the surgeon may be measured directly. Since the combined force of the pressing force $F_1$ and the external force $F_2$ may be computed from the torques $\tau_1$ to $\tau_6$ of each of the joint units 311*a* to 311*f*, the pressing force $F_1$ and the external force $F_2$ may be differentiated based on the combined force and a measurement value from the strain sensor. Consequently, for the pressing force $F_2$ by the front edge unit 313, by setting a value that would not endanger the patient 320 as the purpose of motion, it becomes possible to conduct a malfunction avoidance operation similarly to the case described with reference to FIG. 9.

The above thus describes, as an example of the malfunction avoidance operation, a malfunction avoidance operation based on the torques in the joint units 311*a* to 311*f* with reference to FIGS. 9 and 10. The above example describes a malfunction avoidance operation in which the pressing force on the patient 320 by the front edge unit 313 is restricted to be less than or equal to a certain value, but more generally, a malfunction avoidance operation that targets a pressing force imparted to an external object by contact with the arm unit 310 (including the front edge unit 313) may be conducted. In other words, in the present embodiment, a malfunction of the joint units 311*a* to 311*f* is detected based on the torques produced in the joint units 311*a* to 311*f* according to the pressing force imparted to an external object by contact with the arm unit 310. If such a malfunction is detected, the driving of the joint units 311*a* to 311*f* is controlled and the arm unit 310 is a driven in a state in which the pressing force is restricted to a certain range with respect to the motion of the arm unit 310, and thus a malfunction avoidance operation may be conducted. Also, the restriction of the pressing force is realized by restricting the torques of the joint units 311a to 311f. In this way, by providing a restriction (for example, an upper limit value) on the pressing force (the torques of the joint units 311a to 311f) to conduct a malfunction avoidance operation, it is possible to avoid not only collisions of the front edge unit 313 as discussed above, but also situations in which the surgeon's finger is forcibly caught between links of the arm unit 310, and situations in which the arm unit 310 itself collides with the surgeon or the patient with excessive velocity or force.

Herein, in the present embodiment, a malfunction avoidance operation may also be conducted by a method other than the method described above. For example, in the present embodiment, a malfunction avoidance operation like the following is executable.

For example, a malfunction avoidance operation may also be conducted by restricting the rotational angles of the joint units 311a to 311f to a certain range. In such a malfunction avoidance operation, a malfunction of the joint units 311a to 311f is detected based on the rotational angles of the joint units 311a to 311f, for example. If such a malfunction is detected, the driving of the joint units 311a to 311f is controlled and the arm unit 310 is driven in a state in which the rotational angles are restricted to a certain range with respect to the motion of the arm unit 310. By conducting such a malfunction avoidance operation, it becomes possible to restrict the motion of the joint units 311a to 311f so as not to rotate past a certain angle in a certain direction, thereby making it possible to conduct driving control whereby an invasion prohibition region is provided for the arm unit 120, for example.

As another example, a malfunction avoidance operation may also be conducted by restricting the rotational angular velocities of the joint units 311a to 311f to a certain range. In such a malfunction avoidance operation, a malfunction of the joint units 311a to 311f is detected based on the rotational angular velocities of the joint units 311a to 311f, for example. If such a malfunction is detected, the driving of the joint units 311a to 311f is controlled and the arm unit 310 is driven in a state in which the rotational angular velocities are restricted to a certain range with respect to the motion of the arm unit 310. By conducting such a malfunction avoidance operation, it becomes possible to restrict the motion of the joint units 311a to 311f so as not to rotate at an angular velocity equal to or greater than a certain value, and thus danger caused by the arm unit 310 colliding with the surgeon or the patient may be avoided. In addition, in a malfunction avoidance operation based on the rotational angular velocities of the joint units 311a to 311f, the rotational angular velocities may also be restricted to zero. If the rotational angular velocities are restricted to zero, the joint units 311a to 311f become able to rotate only at extremely slow velocities, thereby further minimizing danger caused by the arm unit 310 colliding with the surgeon or the patient.

The above thus describes the malfunction avoidance operation according to the present embodiment. As described above, according to the present embodiment, a malfunction avoidance operation is conducted based on a factor such as the torques, the rotational angles, or the rotational angular velocities of the joint units 311a to 311f, so that the arm unit 310 does not produce a force equal to or greater than a certain value, or move at a velocity equal to or greater than a certain value. Consequently, it becomes possible to minimize the danger caused by the arm unit 310 colliding with the patient and the surgeon.

Note that in the above description, although malfunction avoidance operations based on the torques, the rotational angles, and the rotational angular velocities of the joint units 311a to 311f are described, the present embodiment is not limited to such an example. A malfunction avoidance operation may also be conducted based on another physical quantity that may express the motion of the arm unit 310, such as the rotational angular accelerations of the joint units 311a to 311f. In addition, in the above description, as the condition imposed on the motion of the arm unit 310, a condition is provided whereby the torques, the angles, or the angular velocities of the joint units 311a to 311f become "less than or equal to" a certain value, but the present embodiment is not limited to such an example. Whether or not the value that serves as the boundary is included or not is arbitrary, and the condition may also be a condition whereby the torques, the angles, or the angular velocities of the joint units 311a to 311f become "less than" a certain value.

(5-3. Partial Function Suspension Operation)

Next, the partial function suspension operation according to the present embodiment will be described. In the partial function suspension operation, when a malfunction is detected in any of the joint units 130, the driving of the other joint units 130 other than the joint unit 130 where the malfunction was detected is controlled, and the arm unit 120 is driven in a state of lowered degrees of freedom.

At this point, in the partial function suspension operation according to the present embodiment, the motion of the joint unit 130 where the malfunction was detected is preferably locked so as not to rotate from a certain angle. Consequently, the arm unit 120 is prevented from moving unexpectedly due to the joint unit 130 where the malfunction was detected, and thus the possibility of the arm unit 120 injuring the surgeon and the patient may be decreased. The locking of the joint unit 130 where the malfunction was detected may be realized by controllably locking the rotational angle, may be realized by a mechanical brake mechanism that acts to suspend the driving of the motor, or may be realized by an electric mechanism that acts to cut off the current supplied to the motor.

Note that if the joint unit 130 is controllably locked, it is sufficient for the rotational angle for each joint unit 130 to be controlled to a certain value. For this reason, this control does not have to be conducted as what is called force control using whole body cooperative control, and may be conducted as position control by the drive control unit 111 of the joint control unit 135 provided in each joint unit 130. For example, in cases such as when a malfunction is occurring in the communication between the robot arm apparatus 10 and the control device 20 illustrated in FIG. 1, conducting whole body cooperative control is impossible, but if the driving of each joint unit 130 is controllable by each drive control unit 111, such controlled locking of the joint unit 130 by the drive control unit 111 may be executed favorably.

However, in the present embodiment, the joint unit 130 where the malfunction was detected does not necessarily need to be locked. For example, by having the drive control unit 111 of the joint unit 130 where the malfunction was detected increases a coefficient of viscosity for the relevant joint unit 130 over the other joint units 130, control may be conducted so that the motion of the joint unit 130 where the malfunction was detected is locked autonomously, but if an external force equal to or greater than a certain value is imposed, the relevant joint unit 130 rotates according to the external force, and the locked position (angle) is changed. Such control may be executed favorably when a malfunction occurs in the communication between the robot arm apparatus 10 and the control device 20, and conducting whole body cooperative control is impossible, as discussed above, for example. The joint unit 130 subjected to such control may be said to be in a quasi-locked state. Note that control of a coefficient of viscosity like the above may be realized by the drive control unit 111 adjusting the amount of current supplied to the motor of the joint unit 130, for example. By conducting such control, even if a malfunction is detected and the motion of the joint unit 130 is locked autonomously, it is still possible to change the rotational angle as needed, thereby making it possible for the surgeon to continue with a medical procedure while moving the arm unit 120 directly, for example.

As another example, if a malfunction occurs in the actuator of the joint unit 130, conducting driving control of the actuator (that is, driving control of the joint unit 130) correctly becomes difficult, and thus controllably locking the joint unit 130 with the drive control unit 111 as above becomes difficult. Consequently, in such cases, the drive control unit 111 may also suspend control of the joint unit 130 where the malfunction was detected. The joint unit 130 for which control is suspended has a larger coefficient of viscosity (larger reaction force) than the other joint units 130 and is difficult to rotate, but is still able to rotate freely in response to an external force equal to or greater than a certain value and act as one rotating part that is not being controlled, and may be considered to be in a quasi-locked state. This may be realized as a result of the motion of the joint unit 130 being mostly locked due to the frictional force of the reduction gear provided in the actuator of the joint unit 130. Even if control is suspended, the rotational angle of the relevant joint unit 130 may be detected as the state of the joint unit 130, and an arm state that also includes the rotational angle of the relevant joint unit 130 may be acquired. Consequently, by appropriately setting an internal model of the arm unit 120 that reflects the inclusion of a freely rotatable joint unit 130, it becomes possible to control the driving of the arm unit 120 with the other joint units 130.

In this way, in the partial function suspension operation according to the present embodiment, the joint unit 130 where a malfunction was detected is locked or quasi-locked, for example, and the driving of the arm unit 120 is controlled using the degrees of freedom of the joint units 130 other than the locked or quasi-locked joint unit 130. As a specific process, for example, the operation condition setting unit 242 may set a constraint condition that the joint unit 130 where the malfunction was detected is locked or quasi-locked, and by performing computations according to whole body cooperative control based on this constraint condition, the driving of the other joint units 130 may be controlled. For example, if the arm unit 120 has just enough degrees of freedom (for example, six degrees of freedom) required to perform a desired operation, by imposing a constraint condition like the above and lowering the degrees of freedom, there is a possibility that the position and the orientation of the arm unit 120 may be restricted. However, in the present embodiment, the position and the orientation of the arm unit 120 may be controlled as much as possible using the remaining degrees of freedom. Consequently, the medical procedure may be continued, and it is possible to prevent the patient from being exposed for further danger due to interrupting the medical procedure or increasing the duration of the medical procedure.

Note that if malfunctions are detected in multiple joint units 130, either the processing of locking or the process of quasi-locking the joint unit 130 discussed above may be selected appropriately according to factors such as the type of failure, for example, and executed on each of the joint units 130 where a malfunction was detected. For example, if malfunctions are detected in multiple joint units 130, depending on the type of failure, one joint unit 130 may be controllably locked according to the method discussed earlier, while another joint unit 130 may be controllably quasi-locked according to the method discussed earlier, while yet another joint unit 130 may be quasi-locked by suspending control over the actuator according to the method discussed earlier. In this way, in order to realize the partial function suspension operation, the processes executed on the joint units 130 where malfunctions were detected may be different for each of the joint units 130, and may be selected appropriately for each joint unit 130 depending on factors such as the type of failure, for example.

Herein, in the present embodiment, the arm unit 120 may also have redundant degrees of freedom. The partial function suspension operation according to the present embodiment may also be applied favorably to an arm unit 120 with redundant degrees of freedom.

The concept of redundant degrees of freedom in the arm unit 120 will be described. For example, suppose that N degrees of freedom are the degrees of freedom required for the arm unit 120 to perform a desired operation (where N is an arbitrary positive number). For example, generally, arbitrarily controlling the position and the orientation of the arm unit 120 in three-dimensional space demands in principle that the arm unit 120 has degrees of freedom equal to or greater than six degrees of freedom. At this point, if the arm unit 120 has more degrees of freedom than N degrees of freedom (for example, N+1 degrees of freedom), the arm unit 120 may be said to have redundant degrees of freedom.

For example, in an arm unit 120 having redundant degrees of freedom, even if the partial function suspension operation is conducted and the degrees of freedom are lowered, degrees of freedom equal to or greater than the desired N degrees of freedom still may be ensured by the joint units 130 other than the joint unit 130 where the malfunction was detected. In this way, in the arm unit 120 having redundant degrees of freedom, even if the partial function suspension operation is conducted, driving control of the arm unit 120 still is continued in a state in which the desired degrees of freedom are ensured, enabling safer continuance of the medical procedure.

Note that as a specific process in the case in which the partial function suspension operation is conducted in an arm unit 120 having redundant degrees of freedom, the internal model may be switched by the operation condition setting unit 242, for example. In an arm unit 120 having redundant degrees of freedom (for example, N+1 degrees of freedom), ordinarily, driving control is conducted in some cases by locking the motion of a certain joint unit 130 and thereby virtually treating the arm unit 120 as an arm unit 120 having the minimum required degrees of freedom (for example, N degrees of freedom). In this case, if the joint unit 130 where the malfunction was detected is locked in an attempt to conduct the partial function suspension operation, since the position of the locked joint unit 130 may change, the internal model may also change. Consequently, multiple internal models corresponding to cases in which each joint unit 130 is locked are prepared in advance, for example, and by selecting an appropriate internal model according to the joint unit 130 where the malfunction was detected, the partial function suspension operation may be executed.

The above thus describes the partial function suspension operation according to the present embodiment. As described above, in the partial function suspension operation according to the present embodiment, when a malfunction is detected in any joint unit 130, the driving of the other joint units 130 other than the joint unit 130 where the malfunction was detected is controlled, and thus the driving of the arm unit 120 is conducted in a state of lowered degrees of freedom. Consequently, although there is a possibility of the position and the orientation of the arm unit 120 being restricted due to the lowering of the degrees of freedom, the driving of the arm unit 120 is continued as much as possible using the remaining degrees of freedom. Consequently, the medical procedure may be continued, and the danger for the patient may be decreased.

In addition, in the present embodiment, the arm unit 120 may also have redundant degrees of freedom. If the partial function suspension operation is conducted with respect to an arm unit 120 having redundant degrees of freedom, even if the degrees of freedom are lowered, enough degrees of freedom originally required for the arm unit 120 to conduct a desired operation still may be ensured, and thus the driving of the arm unit 120 is continued more stably. Consequently, safer continuance of the medical procedure becomes possible.

(5-4. Function Suspension Operation)

Next, the function suspension operation according to the present embodiment will be described. In the function suspension operation, the functions of the arm unit 120 are suspended, but if the functions are suspended so that driving control of each joint unit 130 is not conducted at all, for example, and each joint unit 130 is left up to gravity and allowed to rotate freely, dangers such as the arm unit 120 falling down on top of the patient may be produced. Consequently, in the function suspension operation according to the present embodiment, the functions of the arm unit 120 are suspended more safely.

In the function suspension operation according to the present embodiment, the motion of all joint units 130 constituting the arm unit 120 may be locked. For example, the rotational angles of all joint units 130 constituting the arm unit 120 are locked at certain angles (for example, the angles at the instant the function suspension operation was conducted). Consequently, the position and the orientation of the arm unit 120 are locked, making it possible to prevent the arm unit 120 from moving unexpectedly and injuring the surgeon and the patient.

The locking of each joint unit 130 may be realized by controllably locking the rotational angle, may be realized by a mechanical brake mechanism that acts to suspend the driving of the motor, or may be realized by an electric mechanism that acts to cut off the current supplied to the motor. In addition, if the joint unit 130 is controllably locked similarly to the locking of the joint unit 130 described in (5-3. Partial function suspension operation) above, such control may be conducted as position control by the drive control unit 111 of the joint control unit 135 provided in each joint unit 130. For example, if a malfunction occurs in the communication unit 150 or 170 and communication between the control device 20 and the robot arm apparatus 10 is cut off, the control value computed by the control device 20 cannot be received by each joint unit 130. In such cases, control that locks the angle of each joint unit 130 with the joint control unit 135 may be conducted favorably.

Additionally, in the case of controllably locking the joint unit 130, control may be conducted in which the rotation of the joint unit 130 is locked autonomously, but if an external force equal to or greater than a certain value is imposed, for example, the joint unit 130 rotates according to the external force, and the locked position (angle) is changed. By conducting such control, even if the joint unit 130 is locked, it is still possible to change the rotational angle as needed, thereby making it possible for the surgeon to continue with a medical procedure while moving the arm unit 120 directly, for example.

At this point, the robot arm apparatus 10 additionally may be equipped with a power storage device such as a battery. By providing a power storage device, even if a malfunction occurs whereby the power source is cut off, such as an electric power outage, for example, it is still possible to perform the controlled electrical locking of the joint unit 130 as discussed above. However, depending on the performance of the power storage device, it may be difficult to execute the controlled electrical locking of the joint unit 130 over a long period of time. Consequently, from a safety perspective, when a malfunction occurs whereby the power source is cut off, the joint unit 130 more preferably is locked by a mechanical brake mechanism.

Additionally, if the power source is cut off, it may not be possible to drive the motor of each joint unit 130 so as to maintain the position and the orientation of the arm unit 120, and thus, depending on the center of gravity position of the arm unit 120 when each joint unit 130 is mechanically locked, there is a risk that the balance may not be maintained. Consequently, the robot arm apparatus 10 may also be provided with a counterbalance for supporting the arm unit 120. By adjusting the counterbalance appropriately, even if the center of gravity of the arm unit 120 is unstable, the balance may be maintained, and safer function suspension may be realized.

The above thus describes the function suspension operation according to the present embodiment. As described above, in the function suspension operation according to the present embodiment, the motion of all joint units 130 constituting the arm unit 120 is locked. Consequently, unexpected movement of the arm unit 120 at the same time as the function suspension and endangerment of the surgeon and the patient may be prevented, for example. Additionally, the locking of the joint units 130 may be executed by position control by the joint control unit 135 for each joint unit 130. In this case, it becomes possible to conduct control in which the rotation of each joint unit 130 is locked autonomously, but if an external force equal to or greater than a certain value is imposed, the joint unit 130 rotates according to the external force, and the locked position (angle) is changed. For this reason, the surgeon becomes able to continue with the medical procedure while moving the arm unit 120 directly, and patient safety is improved further.

The above thus respectively describes the malfunction detection process, the malfunction avoidance operation, the partial function suspension operation, and the function suspension operation according to the present embodiment in detail. As described above, in the present embodiment, the occurrence of a malfunction and the type of malfunction may be detected accurately for each joint unit 130. In addition, according to the type of malfunction, an operation from among the malfunction avoidance operation, the partial function suspension operation, and the function suspension operation is selected to be conducted so that the driving of the arm unit 120 is continued as much as possible while also ensuring safety. In this way, according to the present embodiment, the features demanded of a robot arm apparatus from a safety perspective as described in <1. Investigation into safety of robot arm apparatus> above (the ability to execute a malfunction avoidance operation, the ability to execute a partial function suspension operation, the ability to execute a function suspension operation safely, and the ability to accurately execute a malfunction detection process for determining which of these operations to switch to) may be satisfied. Consequently, the arm unit 120 may be driven as much as possible and the medical procedure may be continued while also ensuring the safety of both the surgeon and the patient. Additionally, even if the arm unit 120 is suspended because of a serious malfunction, the functions of the arm unit 120 may be suspended more safely.

<6. Whole Body Cooperative Control>

Hereinafter, a configuration of a control system and a control method for realizing whole body cooperative control according to the present embodiment will be described. As discussed above, by favorably applying the robot arm control system 2 and the robot arm control method described above to a robot arm apparatus for medical use, safety may be improved further. Accordingly, in the following, an embodiment of whole body cooperative control of a robot arm apparatus will be described by taking the example of a robot arm apparatus for medical use.

Note that the above description describes the features demanded of a robot arm apparatus for medical use primarily from a safety perspective. However, in a robot arm apparatus for medical use, various features are demanded from various perspectives other than safety. Consequently, the following cites several other features demanded of a robot arm apparatus for medical use, and describes how these features may also be satisfied by whole body cooperative control according to the present embodiment.

(6-1. Review of Medical Robot Arm Apparatus)

First, to further clarify the present disclosure, the background leading up to the inventors' conceiving of the following embodiments will be described.

In recent years, in the medical or industrial field, robot apparatuses have been widespread in order to perform work more accurately and more quickly. Here, position control and force control are known as control methods of the robot apparatus and each of the joint units. In position control, for example, a command value such as an angle is provided to an actuator of a joint unit, and driving of the joint unit is controlled according to the command value. Meanwhile, in force control, a target value of force applied to a task target by a whole robot apparatus is given, and driving of a joint unit (for example, torque generated by the joint unit) is controlled such that the force indicated by the target value is implemented.

Generally, most robot apparatuses are driven by position control since it is convenient to control and a system configuration is simple. However, position control is commonly called "hard control" since cannot easily deal with external force flexibly, and position control is not suitable for a robot apparatus performing a task while performing physical interaction (for example, physical interaction with a person) with various external worlds. Meanwhile, force control has a complicated system configuration, but can implement "soft control" of a power order, and thus force control is a control method suitable, particularly, for a robot apparatus performing physical interaction with a person and a control method having excellent usability.

For example, as an example of a robot apparatus applying force control, refer to JP 2010-188471A, which is a prior application by the same applicant as the present applicant of this specification. Patent Literature 1 discloses a robot apparatus that includes a movement mechanism configured with 2 wheels and an arm unit configured with a plurality of joint units, and performs control such that the wheels and the joint units are driven in a cooperative manner as a whole (performs whole body cooperative control).

Meanwhile, in recent years, in the medical field, attempts to use a balance arm (also referred to as support arm) in which various medical units (front edge units) are installed at a front edge of an arm unit when various medical procedures (for example, surgery or an examination) are performed have been made. For example, a method in which various imaging devices with imaging functions such as a microscope, an endoscope, or a camera is installed on a front edge of an arm unit of a balance arm as a front edge unit, and a practitioner (a user) performs various medical procedures while observing an image of the medical procedure part captured by the imaging device has been proposed.

However, the balance arm has to be equipped with a counter balance weight (also called a counter weight or a balancer) for maintaining balance of force when the arm unit is moved and thus a device size tends to increase. A device used in a medical procedure has to be small in size since it is necessary to secure a task space for the medical procedure, but it is difficult to meet such a demand in general balance arms being proposed. Further, in the balance arm, only some driving of the arm unit, for example, only biaxial driving for moving the front edge unit on a (two-dimensional) plane is electric driving, and manual positioning by the practitioner or a medical staff therearound is necessary for movement of the arm unit and the front edge unit. Thus, in the general balance arms, it is difficult to secure stability (for example, positioning accuracy of the front edge unit, vibration suppression, and the like) at the time of photography and secure a degree of freedom of observation by which it is possible to observe in various directions, for example, in a state in which a point of view is fixed on a certain part of a patient's body.

Particularly, when observing a surgical site with an imaging device attached to an arm unit, there is demand to be able to observe the surgical site from different distances and different angles, while keeping the viewpoint locked onto the surgical site. Such observation may be realized by causing the imaging device to perform a pivot operation, but performing a pivot operation with a balance arm requires a complex mechanical configuration as described in Patent Literature 1 above, and achieving high operability is difficult.

In light of the above circumstances, as a device to replace a balance arm, there is proposed a robot arm apparatus for medical use whose driving is controlled by position control. However, in order to more efficiently perform a medical procedure and reduce a burden on a user, high operability enabling more intuitive control of a position or posture of an arm unit and an imaging unit installed as a front edge unit by a user is necessary for driving control of a robot arm apparatus. In a robot arm apparatus in which driving is controlled by position control, it is difficult to meet such a user demand.

Accordingly, there is demand to further reduce the user burden by realizing a robot arm apparatus capable of performing driving control of the arm unit with higher stability and higher operability. In addition, since the robot arm apparatus is used for medical use, the robot arm apparatus is desired to have the following features in addition to the features required for safety purpose described in <1. Investigation into safety of robot arm apparatus>.

Figure 11:
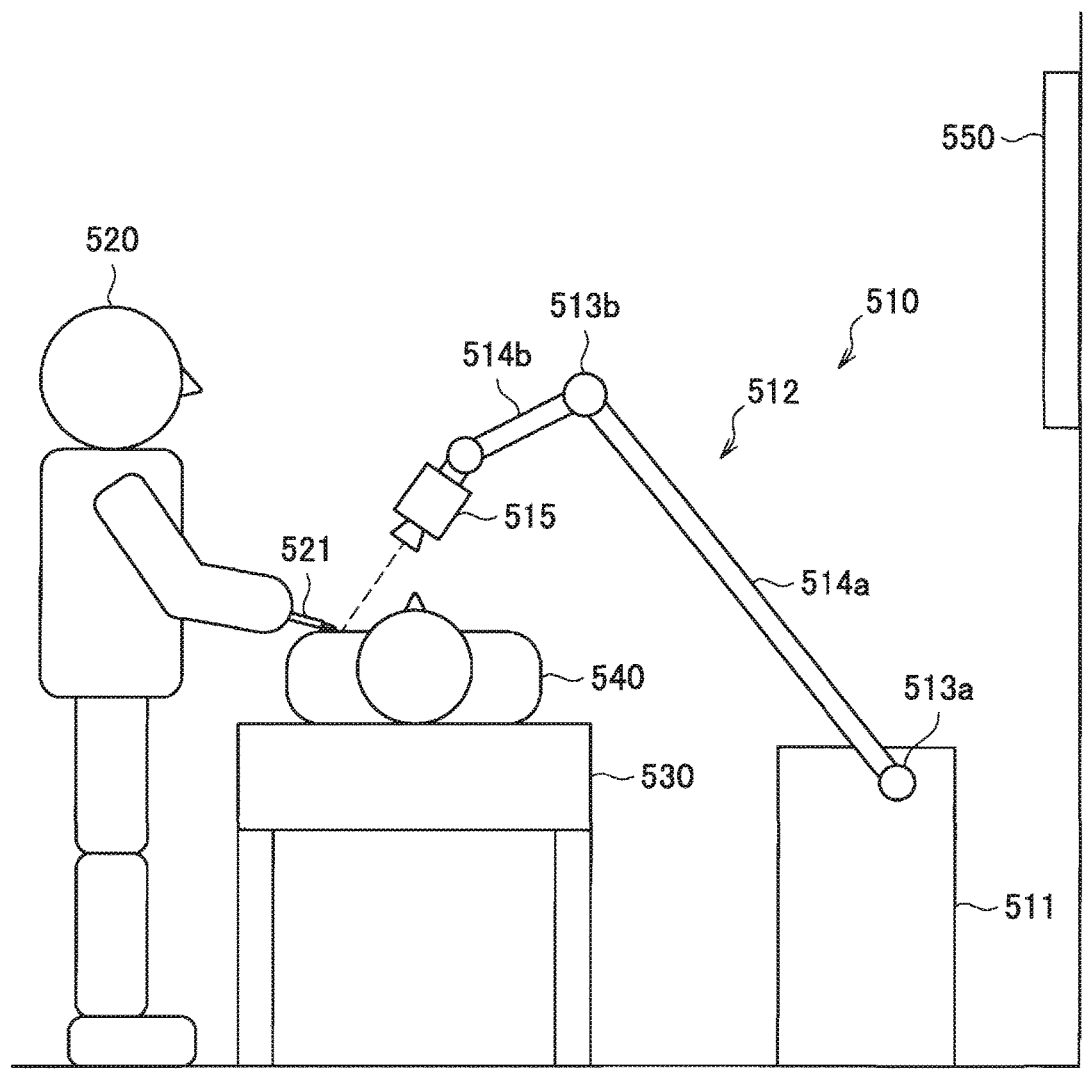
FIG. 11 is an explanatory diagram for describing an application example of using a robot arm apparatus according to an embodiment of the present disclosure for a medical purpose.

FIG. 11 will be referenced to describe an application example for the case of a robot arm apparatus according to an embodiment of the present disclosure being used for medical use, and the features required for the robot arm apparatus for medical use. FIG. 11 is an explanatory diagram for describing an application example for the case of a robot arm apparatus according to an embodiment of the present disclosure being used for medical use.

FIG. 11 schematically illustrates an exemplary medical procedure using the robot arm apparatus according to the present embodiment. Specifically, FIG. 11 illustrates an example in which a doctor serving as a practitioner (user) 520 performs surgery on a medical procedure target (patient) 540 on a medical procedure table 530, for example, using surgical instruments 521 such as a scalpel, tweezers, and forceps. In the following description, the medical procedure refers to a general concept including various kinds of medical treatments that the doctor serving as the user 520 performs on the patient of the medical procedure target 540 such as surgery or an examination. The example of FIG. 11 illustrates surgery as an example of the medical procedure, but the medical procedure using a robot arm apparatus 510 is not limited to surgery and may be various kinds of other medical procedures such as an examination using an endoscope.

The robot arm apparatus 510 according to the present embodiment is installed at the side of the medical procedure table 530. The robot arm apparatus 510 includes a base unit 511 serving as a base and an arm unit 512 extending from the base unit 511. The arm unit 512 includes a plurality of joint units 513a, 513b, 513c, a plurality of links 514a and 514b connected by the joint units 513a and 513b, and an imaging unit 515 installed at the front edge of the arm unit 512. In the example illustrated in FIG. 11, for the sake of simplification, the arm unit 512 includes the 3 joint units 513a to 513c and the 2 links 514a and 514b, but practically, for example, the number and the shape of the joint units 513a to 513c and the links 514a and 514b and a direction of the driving shaft of the joint units 513a to 513c may be appropriately set to express a desired degree of freedom in view of a degree of freedom of the position and posture of the arm unit 512 and the imaging unit 515.

The joint units 513a to 513c have a function of connecting the links 514a and 514b to be rotatable, and as the joint units 513a to 513c are rotationally driven, driving of the arm unit 512 is controlled. Here, in the following description, the position of each component of the robot arm apparatus 510 is the position (coordinates) in a space specified for driving control, and the posture of each component is a direction (angle) to an arbitrary axis in a space specified for driving control. Further, in the following description, driving (or driving control) of the arm unit 512 refers to changing (controlling a change of) the position and posture of each component of the arm unit 512 by performing driving (or driving control) of the joint units 513a to 513c and driving (or driving control) of the joint units 513a to 513c.

Various kinds of medical apparatuses are connected to the front edge of the arm unit 512 as the front edge unit. In the example illustrated in FIG. 11, the imaging unit 515 is installed at the front edge of the arm unit 512 as an exemplary front edge unit. The imaging unit 515 is a unit that acquires an image (a photographed image) of a photographing target and is, for example, a camera capable of capturing a moving image or a still image. As illustrated in FIG. 1, the posture or the position of the arm unit 512 and the imaging unit 515 is controlled by the robot arm apparatus 510 such that the imaging unit 515 installed at the front edge of the arm unit 512 photographs a state of a medical procedure part of the medical procedure target 540. The front edge unit installed at the front edge of the arm unit 512 is not limited to the imaging unit 515 and may be various kinds of medical apparatuses. For example, the medical apparatus includes various kinds of units used when the medical procedure is performed such as an endoscope, a microscope, a unit having an imaging function such as the imaging unit 515, various kinds of medical procedure instruments, and an examination apparatus. As described above, the robot arm apparatus 510 according to the present embodiment is a medical robot arm apparatus equipped with a medical apparatus. Further, a stereo camera having two imaging units (camera units) may be installed at the front edge of the arm unit 512, and may perform photography so that an imaging target is displayed as a three dimensional (3D) image. Note that the robot arm apparatus 510 provided with the imaging unit 515 or a camera unit such as the stereo camera for imaging the site of the medical procedure may also be called a video microscope robot arm apparatus.

Further, a display device 550 such as a monitor or a display is installed at a position facing the user 520. The captured image of the medical procedure part captured by the imaging unit 515 is displayed on a display screen of the display device 550. The user 520 performs various kinds of treatments while viewing the captured image of the medical procedure part displayed on the display screen of the display device 550.

As described above, in the present embodiment, in the medical field, a technique of performing surgery while photographing the medical procedure part through the robot arm apparatus 510 is proposed. Here, in various kinds of medical procedures including surgery, it is necessary to reduce fatigue or a burden on the user 520 and the patient 540 by performing the medical procedure efficiently. In order to satisfy such a demand, in the robot arm apparatus 510, for example, the following capabilities are considered desirable.

First, as a first point, the robot arm apparatus 510 should secure a task space for surgery. If the arm unit 512 or the imaging unit 515 hinders a field of vision of the practitioner or impedes motion of a hand performing a treatment while the user 520 is performing various kinds of treatments on the medical procedure target 540, the efficiency of surgery is lowered. Further, in FIG. 11, although not illustrated, in an actual surgical scene, for example, a plurality of other doctors and/or nurses performing various support tasks of handing an instrument to the user 520 or checking various kinds of vital signs of the patient 540 are commonly around the user 520 and the patient 540, and there are other devices for performing the support tasks, and thus a surgical environment is complicated. Thus, a small size is desirable in the robot arm apparatus 510.

Next, as a second point, the robot arm apparatus 510 should have high operability for moving the imaging unit 515. For example, the user 520 may desire to observe the same medical procedure part at various positions and angles while performing a treatment on the medical procedure part according to a surgical part or surgical content. In order to change an angle at which the medical procedure part is observed, it is necessary to change an angle of the imaging unit 515 with respect to the medical procedure part, but at this time, it is more desirable that only a photographing angle be changed in a state in which the photographing direction of the imaging unit 515 is fixed to the medical procedure part (that is, while photographing the same part). Thus, for example, the robot arm apparatus 510 should have operability of a high degree of freedom such as a turning movement (a pivot movement) in which the imaging unit 515 moves within a surface of a cone having the medical procedure part as an apex, and an axis of the cone is used as a pivot axis in the state in which the photographing direction of the imaging unit 515 is fixed to the medical procedure part. Since the photographing direction of the imaging unit 515 is fixed to a certain medical procedure part, the pivot movement is also called point lock movement.

Further, in order to change the position and the angle of the imaging unit 515, for example, a method in which the user 520 manually moves the arm unit 512 to move the imaging unit 515 to a desired position and at a desired angle is considered. Thus, it is desirable that there be operability enabling movement of the imaging unit 515, the pivot movement, or the like to be easily performed even with one hand.

Further, there may be a demand from the user 520 to move a photographing center of a captured image captured by the imaging unit 515 from a part on which a treatment is being performed to another part (for example, a part on which a next treatment will be performed) while performing a treatment with both hands during surgery. Thus, various driving methods of the arm unit 512 are necessary such as a method of controlling driving of the arm unit 512 by an operation input from an input unit such as a pedal as well as a method of controlling driving of the arm unit 512 by a manual motion when it is desired to change the position and posture of the imaging unit 515.

As described above as the capability of the second point, the robot arm apparatus 510 should have high operability enabling easy movement, for example, by the pivot movement or the manual motion and satisfying intuition or a desire of the user 520.

Lastly, as a third point, the robot arm apparatus 510 should have stability in the driving control of the arm unit 512. The stability in the driving control of the arm unit 512 may be stability in the position and posture of the front edge unit when the arm unit 512 is driven. The stability in the driving control of the arm unit 512 also includes smooth movement and suppression of vibration (vibration suppression) of the front edge unit when the arm unit 512 is driven. For example, when the front edge unit is the imaging unit 515 as in the example illustrated in FIG. 11, if the position or the posture of the imaging unit 515 is unstable, the captured image displayed on the display screen of the display device 550 is unstable, and the user may have a feeling of discomfort. Particularly, when the robot arm apparatus 510 is used for surgery, a use method in which a stereo camera including two imaging units (camera units) is installed as the front edge unit, and a 3D image generated based on photographed images obtained by the stereo camera is displayed can be assumed. As described above, when the 3D image is displayed, if the position or the posture of the stereo camera is unstable, the user is likely to experience 3D sickness. Further, an observation range photographed by the imaging unit 515 may be enlarged up to about φ15 mm depending on a surgical part or surgical content. When the imaging unit 515 enlarges and photographs a narrow range as described above, slight vibration of the imaging unit 515 is shown as a large shake or deviation of an imaged image. Thus, high positioning accuracy with a permissible range of about 1 mm is necessary for driving control of the arm unit 512 and the imaging unit 515. As described above, high-accuracy responsiveness and high positioning accuracy are necessary in driving control of the arm unit 512.

The inventors have reviewed existing general balance arms and robot arm apparatuses based on position control in terms of the above-mentioned 3 capabilities.

First, with regard to securing the task space for the surgery of the first point, in the general balance arm, a counter balance weight (also called a counter weight or a balancer) for maintaining balance of force when the arm unit is moved is installed inside the base unit or the like, and thus it is difficult to reduce the size of the balance arm apparatus, and it is difficult to say that the corresponding capability is fulfilled.

Further, with regard to the high operability of the second point, in the general balance arm, only some driving of the arm unit, for example, only biaxial driving for moving the imaging unit on a (two-dimensional) plane is electric driving, and manual positioning is necessary for movement of the arm unit and the imaging unit, and thus it is difficult to say that high operability can be implemented. Further, in the general robot arm apparatus based on the position control, since it is difficult to flexibly deal with external force by the position control used for driving control of the arm unit, that is, control of the position and posture of the imaging unit, the position control is commonly called "hard control" and is not suitable of implementing desired operability satisfying the user's intuition.

Further, with regard to stability in driving control of the arm unit of the third point, the joint unit of the arm unit generally has factors that are not easily modelized such as friction, inertia, and the like. In the general balance arm or the robot arm apparatus based on the position control, the factors serve as a disturbance in the driving control of the joint unit, and even when a theoretically appropriate control value (for example, a current value applied to a motor of the joint unit) is given, there are cases in which desired driving (for example, rotation at a desired angle in the motor of the joint unit) is not implemented, and it is difficult to implement high stability necessary for driving control of the arm unit.

As described above, in addition to the features required for safety purpose described in <1. Investigation into safety of robot arm apparatus>, the inventors have reviewed robot arm apparatuses being used for medical purposes and learned that there is a demand for the capabilities of the above-mentioned three points with regard to the robot arm apparatus. However, it is difficult for the general balance arm or the robot arm apparatus based on the position control to easily fulfill such capabilities. The inventors have developed a robot arm apparatus, a robot arm control system, a robot arm control method, and a program according to the embodiments described later as a result of reviewing configurations satisfying the capabilities of the three points. Hereinafter, an embodiments of the configuration developed by the inventors will be described in detail.

(5-2. Embodiment of Present Disclosure)

A robot arm control system according to an embodiment of the present disclosure will be described below. In the robot arm control system according to the present embodiment, driving of a plurality of joint units installed in the robot arm apparatus is controlled by whole body cooperative control using generalized inverse dynamics. Further, ideal joint control of implementing an ideal response to a command value by correcting influence of a disturbance is applied to driving control of the joint unit.

In the following description of the present embodiment, an external appearance of the robot arm apparatus according to the present embodiment and a schematic configuration of the robot arm apparatus will be first described in (6-2-1. External appearance of robot arm apparatus). Then, an overview of the generalized inverse dynamics and the ideal joint control used for control of the robot arm apparatus according to the present embodiment will be described in (6-2-2. Generalized inverse dynamics) and (6-2-3. Ideal joint control). Then, a configuration of a system for controlling the robot arm apparatus according to the present embodiment will be described with reference to a functional block diagram in (6-2-4. Configuration of robot arm control system). Lastly, a specific example of the whole body cooperative control using the generalized inverse dynamics in the robot arm apparatus according to the present embodiment will be described in (6-2-5. Specific example of purpose of motion).

Further, the following description will proceed with an example in which a front edge unit of an arm unit of a robot arm apparatus according to an embodiment of the present disclosure is an imaging unit, and a medical procedure part is photographed by the imaging unit during surgery as illustrated in FIG. 11 as an embodiment of the present disclosure, but the present embodiment is not limited to this example. The robot arm control system according to the present embodiment can be applied even when a robot arm apparatus including a different front edge unit is used for another purpose.

(6-2-1. External Appearance of Robot Arm Apparatus)

Figure 12:
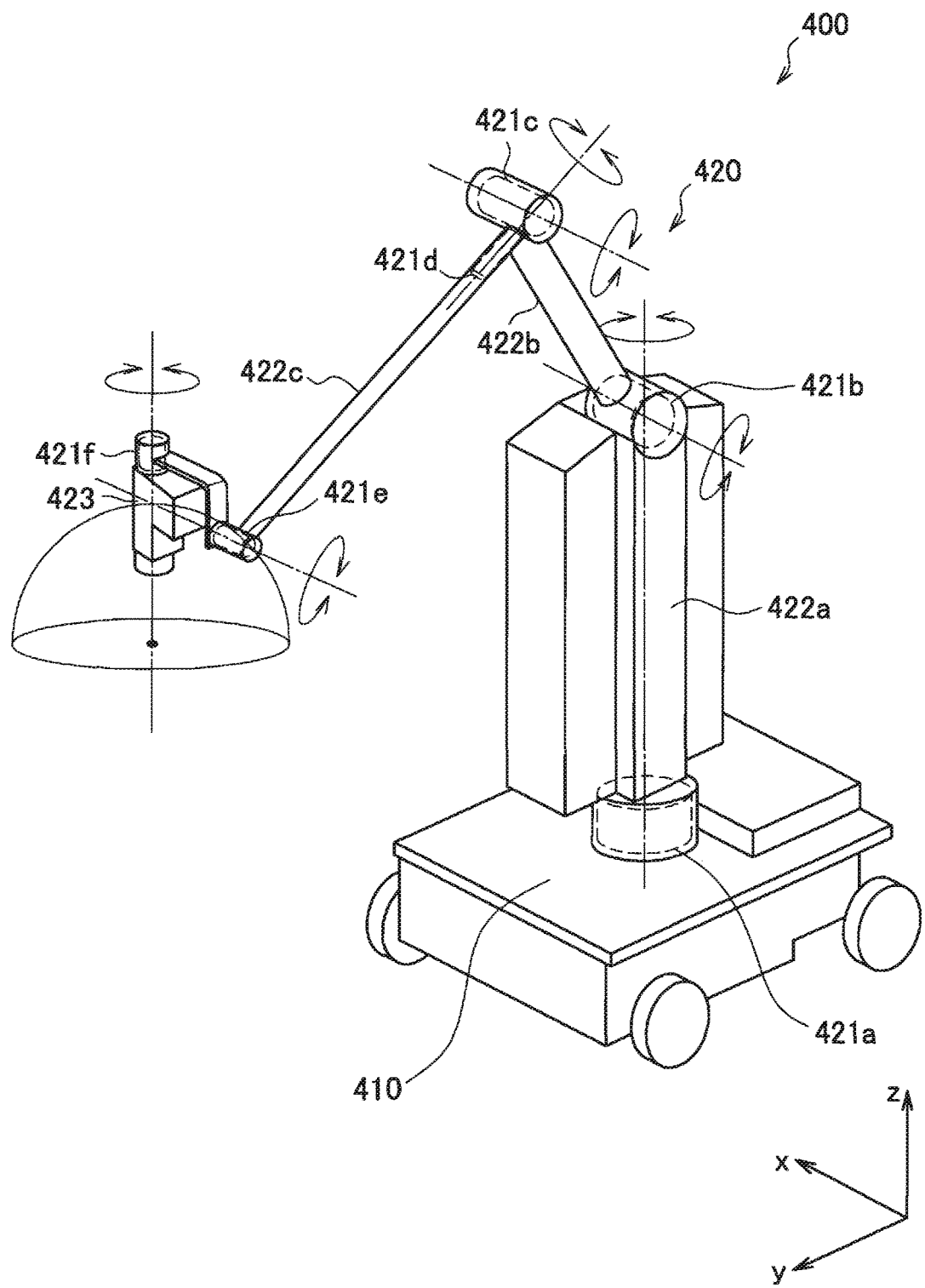
FIG. 12 is a schematic diagram illustrating an external appearance of a robot arm apparatus according to an embodiment of the present disclosure.

First, a schematic configuration of a robot arm apparatus according to an embodiment of the present disclosure will be described with reference to FIG. 12. FIG. 12 is a schematic diagram illustrating an external appearance of a robot arm apparatus according to an embodiment of the present disclosure.

Referring to FIG. 12, a robot arm apparatus 400 according to the present embodiment includes a base unit 410 and an arm unit 420. The base unit 410 serves as the base of the robot arm apparatus 400, and the arm unit 420 extends from the base unit 410. Although not illustrated in FIG. 12, a control unit that controls the robot arm apparatus 400 in an integrated manner may be installed in the base unit 410, and driving of the arm unit 420 may be controlled by the control unit. For example, the control unit is configured with various kinds of signal processing circuits such as a central processing unit (CPU) or a digital signal processor (DSP).

The arm unit 420 includes a plurality of joint units 421a to 421f, a plurality of links 422a to 422c that are connected with one another by the joint units 421a to 421f, and an imaging unit 423 installed at the front edge of the arm unit 420.

The links 422a to 422c are rod-like members, one end of the link 422a is connected with the base unit 410 through the joint unit 421a, the other end of the link 422a is connected with one end of the link 422b through the joint unit 421b, and the other end of the link 422b is connected with one end of the link 422c through the joint units 421c and 421d. Further, the imaging unit 423 is connected to the front edge of the arm unit 420, that is, the other end of the link 422c through the joint units 421e and 421f. As described above, the arm shape extending from the base unit 410 is configured such that the base unit 410 serves as a support point, and the ends of the plurality of links 422a to 422c are connected with one another through the joint units 421a to 421f.

The imaging unit 423 is a unit that acquires an image of a photographing target, and is, for example, a camera that captures a moving image, a still image. The driving of the arm unit 420 is controlled such that the position and posture of the imaging unit 423 are controlled. In the present embodiment, for example, the imaging unit 423 photographs some regions of the body of the patient serving as the medical procedure part. Here, the front edge unit installed at the front edge of the arm unit 420 is not limited to the imaging unit 423, and various kinds of medical apparatuses may be connected to the front edge of the arm unit 420 as the front edge unit. As described above, the robot arm apparatus 400 according to the present embodiment is a medical robot arm apparatus equipped with a medical apparatus.

Here, the description of the robot arm apparatus 400 will proceed with coordinate axes defined as illustrated in FIG. 12. Further, a vertical direction, a longitudinal direction, and a horizontal direction are defined according to the coordinate axes. In other words, a vertical direction with respect to the base unit 410 installed on the floor is defined as a z axis direction and a vertical direction. Further, a direction along which the arm unit 420 extends from the base unit 410 as a direction orthogonal to the z axis (that is, a direction in which the imaging unit 423 is positioned with respect to the base unit 410) is defined as a y axis direction and a longitudinal direction. Furthermore, a direction that is orthogonal to the y axis and the z axis is an x axis direction and a horizontal direction.

The joint units 421a to 421f connect the links 422a to 422c to be rotatable. Each of the joint units 421a to 421f includes a rotation mechanism that includes an actuator and is rotationally driven on a certain rotary axis according to driving of the actuator. By controlling rotary driving in each of the joint units 421a to 421f, for example, it is possible to control driving of the arm unit 420 to extend or shorten (fold) the arm unit 420. Here, driving of the joint units 421a to 421f is controlled by the whole body cooperative control which will be described in (6-2-2. Generalized inverse dynamics) and the ideal joint control which will be described in (6-2-3. Ideal joint control). Further, as described above, since the joint units 421a to 421f according to the present embodiment include the rotation mechanism, in the following description, driving control of the joint units 421a to 421f specifically means controlling a rotational angle and/or generated torque (torque generated by the joint units 421a to 421O of the joint units 421a to 421f.

The robot arm apparatus 400 according to the present embodiment includes the 6 joint units 421a to 421f, and implements 6 degrees of freedom with regard to driving of the arm unit 420. Specifically, as illustrated in FIG. 12, the joint units 421a, 421d, and 421f are installed such that the long axis directions of the links 422a to 422c connected thereto and the photographing direction of the imaging unit 473 connected thereto are set as the rotary axis direction, and the joint units 421b, 421c, and 421e are installed such that an x axis direction serving as a direction in which connection angles of the links 422a to 422c and the imaging unit 473 connected thereto are changed within a y-z plane (a plane specified by the y axis and the z axis) is set as the rotary axis direction. As described above, in the present embodiment, the joint units 421a, 421d, and 421f have a function of performing yawing, and the joint units 421b, 421c, and 421e have a function of performing pitching.

As the above-described configuration of the arm unit 420 is provided, the robot arm apparatus 400 according to the present embodiment can implement the 6 degrees of freedom on driving of the arm unit 420, and thus can freely move the imaging unit 423 within a movable range of the arm unit 420. FIG. 12 illustrates a hemisphere as an exemplary movable range of the imaging unit 423. When the central point of the hemisphere is the photographing center of the medical procedure part photographed by the imaging unit 423, the medical procedure part can be photographed at various angles by moving the imaging unit 423 on the spherical surface of the hemisphere in a state in which the photographing center of the imaging unit 423 is fixed to the central point of the hemisphere.

A configuration of the joint units 421a to 421f illustrated in FIG. 12 will be described herein in further detail with reference to FIG. 13. Further, a configuration of an actuator serving as a component mainly related to the rotary driving of the joint units 421a to 421f among the components of the joint units 421a to 421f will be described herein with reference to FIG. 13. The actuator illustrated in FIG. 13 may correspond to the actuator 180 illustrated in drawings such as FIGS. 2 and 6.

Figure 13:
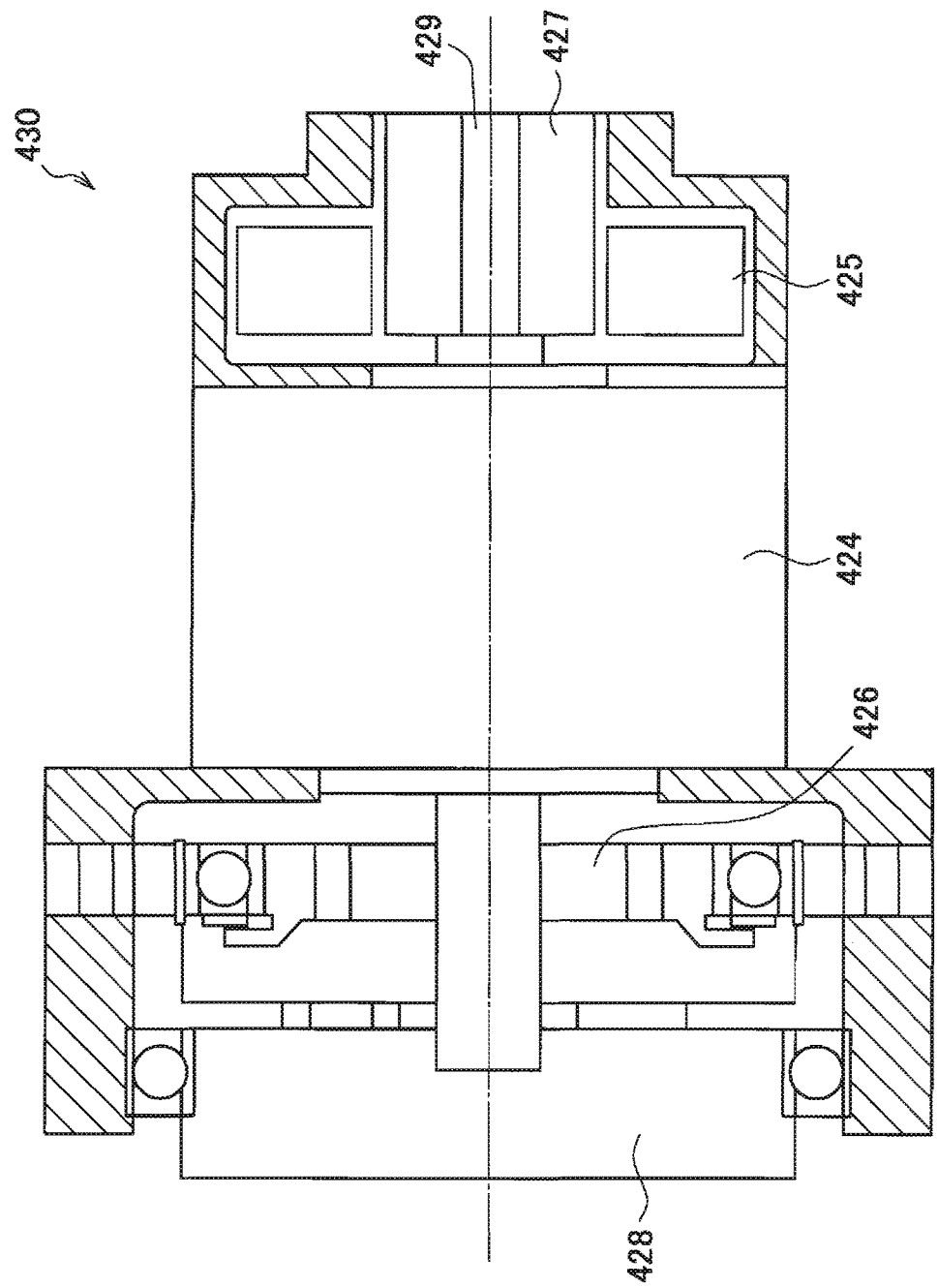
FIG. 13 is a cross-sectional diagram schematically illustrating a state in which an actuator of a joint unit according to an embodiment of the present disclosure is cut along a cross section passing through a rotary axis.

FIG. 13 is a cross-sectional diagram schematically illustrating a state in which an actuator of each of the joint units 421a to 421f according to an embodiment of the present disclosure is cut along a cross section passing through the rotary axis. FIG. 13 illustrates an actuator among the components of the joint units 421a to 421f, but the joint units 421a to 421f may have any other component. For example, the joint units 421a to 421f have various kinds of components necessary for driving of the arm unit 420 such as a control unit for controlling driving of the actuator and a support member for connecting and supporting the links 422a to 422c and the imaging unit 423 in addition to the components illustrated in FIG. 13. Further, in the above description and the following description, driving of the joint unit of the arm unit may mean driving of the actuator in the joint unit.

As described above, in the present embodiment, driving of the joint units 421a to 421f is controlled by the ideal joint control which will be described later in (6-2-3. Ideal joint control). Thus, the actuator of the joint units 421a to 421f illustrated in FIG. 13 is configured to perform driving corresponding to the ideal joint control. Specifically, the actuator of the joint units 421a to 421f is configured to be able to adjust the rotational angles and torque associated with the rotary driving in the joint units 421a to 421f. Further, the actuator of the joint units 421a to 421f is configured to be able to arbitrarily adjust a viscous drag coefficient on a rotary motion. For example, it is possible to implement a state in which rotation is easily performed (that is, the arm unit 420 is easily moved by a manual motion) by force applied from the outside or a state in which rotation is not easily performed (that is, the arm unit 420 is not easily moved by a manual motion) by force applied from the outside.

Referring to FIG. 13, an actuator 430 of the joint units 421a to 421f according to the present embodiment includes a motor 424, a motor driver 425, a reduction gear 426, an encoder 427, a torque sensor 428, and a driving shaft 429. As illustrated in FIG. 13, the encoder 427, the motor 424, the reduction gear 426, and the torque sensor 428 are connected to the driving shaft 429 in series in the described order. Note that the motor 424, the motor driver 425, the reduction gear 426, the encoder 427, and the torque sensor 428 may correspond to the motor 181, the motor driver unit 170, the reduction gear 185, the motor angle sensor 184a, and the torque sensor 183 illustrated in FIG. 6, respectively.

The motor 424 is a prime mover in the actuator 430, and causes the driving shaft 429 to rotate about its axis. For example, the motor 424 is an electric motor such as a brushless DC motor. In the present embodiment, as the motor 424 is supplied with an electric current, the rotary driving is controlled.

The motor driver 425 is a driver circuit (a driver integrated circuit (IC)) for supplying an electric current to the motor 424 and rotationally driving the motor 424, and can control the number of revolutions of the motor 424 by adjusting an amount of electric current supplied to the motor 424. Further, the motor driver 425 can adjust the viscous drag coefficient on the rotary motion of the actuator 430 by adjusting an amount of electric current supplied to the motor 424.

The reduction gear 426 is connected to the driving shaft 429, and generates rotary driving force (that is, torque) having a certain value by reducing the rotation speed of the driving shaft 429 generated by the motor 424 at a certain reduction ratio. A high-performance reduction gear of a backlashless type is used as the reduction gear 426. For example, the reduction gear 426 may be a Harmonic Drive (a registered trademark). The torque generated by the reduction gear 426 is transferred to an output member (not illustrated) (for example, a connection member of the links 422a to 422c, the imaging unit 423, or the like) at a subsequent stage through the torque sensor 428 connected to an output shaft of the reduction gear 426.

The encoder 427 is connected to the driving shaft 429, and detects the number of revolutions of the driving shaft 429. It is possible to obtain information such as the rotational angle, the rotational angular velocity, and the rotational angular acceleration of the joint units 421a to 421f based on a relation between the number of revolutions of the driving shaft 429 detected by the encoder and the reduction ratio of the reduction gear 426. Note that in the example illustrated in FIG. 13, the encoder 427 is provided on the drive shaft 429, or in other words, the rotary shaft of the motor 424, but the present embodiment is not limited to such an example. Like the example configuration illustrated in FIG. 6, an encoder for detecting the rotational angle of the output shaft additionally may be provided on the downstream side of the reduction gear 426.

The torque sensor 428 is connected to the output shaft of the reduction gear 426, and detects the torque generated by the reduction gear 426, that is, the torque output by the actuator 430. In the following description, the torque output by the actuator 430 is also referred to simply as "generated torque."

As described above, the actuator 430 can adjust the number of revolutions of the motor 424 by adjusting an amount of electric current supplied to the motor 424. Here, the reduction ratio of the reduction gear 426 may be appropriately set according to the purpose of the robot arm apparatus 400. Thus, the generated torque can be controlled by appropriately adjusting the number of revolutions of the motor 424 according to the reduction ratio of the reduction gear 426. Further, in the actuator 430, it is possible to obtain information such as the rotational angle, the rotational angular velocity, and the rotational angular acceleration of the joint units 421a to 421f based on the number of revolutions of the driving shaft 429 detected by the encoder 427, and it is possible to detect the generated torque in the joint units 421a to 421f through the torque sensor 428.

Further, the torque sensor 428 can detect external torque applied from the outside as well as the generated torque generated by the actuator 430. Thus, as the motor driver 425 adjusts an amount of electric current supplied to the motor 424 based on the external torque detected by the torque sensor 428, it is possible to adjust the viscous drag coefficient on the rotary motion and implement, for example, the state in which rotation is easily or not easily performed by force applied from the outside.

Figure 14A:
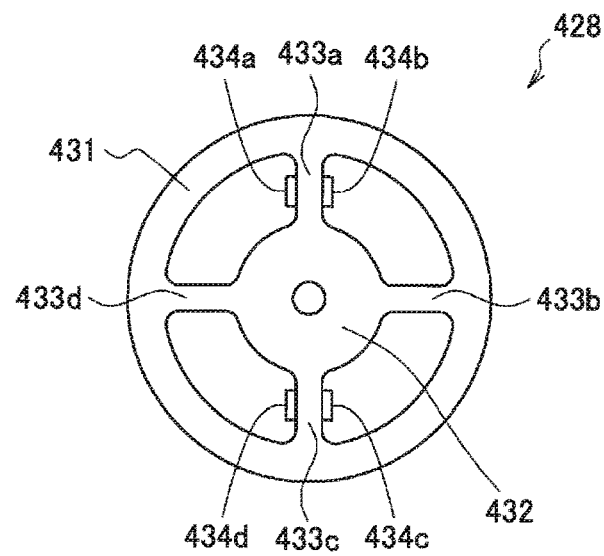
FIG. 14A is a schematic diagram schematically illustrating a state of a torque sensor illustrated in FIG. 13 viewed in an axis direction of a driving shaft.

Here, a configuration of the torque sensor 428 will be described in detail with reference to FIGS. 14A and 14B. FIG. 14A is a schematic diagram schematically illustrating a state of the torque sensor 428 illustrated in FIG. 13 viewed in the axis direction of the driving shaft 429.

Referring to FIG. 14A, the torque sensor 428 includes an outer ring section 431, an inner ring section 432, beam sections 433a to 433d, and distortion detecting elements 434a to 434d. As illustrated in FIG. 14A, the outer ring section 431 and the inner ring section 432 are concentrically arranged. In the present embodiment, the inner ring section 432 is connected to an input side, that is, the output shaft of the reduction gear 426, and the outer ring section 431 is connected to an output side, that is, an output member (not illustrated) at a subsequent stage.

The 4 beam sections 433a to 433d are arranged between the outer ring section 431 and the inner ring section 432 that are concentrically arranged, and connect the outer ring section 431 with the inner ring section 432. As illustrated in FIG. 14A, the beam sections 433a to 433d are interposed between the outer ring section 431 and the inner ring section 432 so that two neighboring sections of the beam sections 433a to 433d form an angle of 90°.

The distortion detecting elements 434a to 434d are installed at the two sections facing each other, that is, disposed at an angle of 180° among the beam sections 433a to 433d. It is possible to detect the generated torque and the external torque of the actuator 430 based on a deformation amount of the beam sections 433a to 433d detected by the distortion detecting elements 434a to 434d.

In the example illustrated in FIG. 14A, among the beam sections 433a to 433d, the distortion detecting elements 434a and 434b are installed at the beam section 433a, and the distortion detecting elements 434c and 434d are installed at the beam section 433c. Further, the distortion detecting elements 434a and 434b are installed with the beam section 433a interposed therebetween, and the distortion detecting elements 434c and 434d are installed with the beam section 433c interposed therebetween. For example, the distortion detecting elements 434a to 434d are distortion gauges attached to the surfaces of the beam sections 433a and 433c, and detect geometric deformation amounts of the beam sections 433a and 433c based on a change in electrical resistance. As illustrated in FIG. 14A, the distortion detecting elements 434a to 434d are installed at 4 positions, and the detecting elements 434a to 434d configure a so-called Wheatstone bridge. Thus, since it is possible to detect distortion using a so-called four-gauge technique, it is possible to reduce influence of interference of shafts other than a shaft in which distortion is detected, eccentricity of the driving shaft 429, a temperature drift, or the like.

As described above, the beam sections 433a to 433d serve as a distortion inducing body whose distortion is detected. The type of the distortion detecting elements 434a to 434d according to the present embodiment is not limited to a distortion gauge, and any other element may be used. For example, the distortion detecting elements 434a to 434d may be elements that detect the deformation amounts of the beam sections 433a to 433d based on a change in magnetic characteristics.

Although not illustrated in FIGS. 13 and 14A, the following configuration may be applied in order to improve the detection accuracy of the generated torque and the external torque by the torque sensor 428. For example, when portions of the beam sections 433a to 433d which are connected with the outer ring section 431 are formed at a thinner thickness than other portions, since a support moment is released, linearity of a deformation amount to be detected is improved, and influence by a radial load is reduced. Further, when both the outer ring section 431 and the inner ring section 432 are supported by a housing through a bearing, it is possible to exclude an action of other axial force and a moment from both the input shaft and the output shaft. Further, in order to reduce another axial moment acting on the outer ring section 431, a support bearing may be arranged at the other end of the actuator 430 illustrated in FIG. 13, that is, a portion at which the encoder 427 is arranged.

The configuration of the torque sensor 428 has been described above with reference to FIG. 14A. As described above, through the configuration of the torque sensor 428 illustrated in FIG. 14A, it is possible to detect the generated torque and the external torque of the actuator 430 with a high degree of accuracy.

Here, in the present embodiment, the configuration of the torque sensor 428 is not limited to the configuration illustrated in FIG. 14A and may be any other configuration. Another exemplary configuration of the torque sensor applied to the actuator 430 other than the torque sensor 428 will be described with reference to FIG. 14B.

Figure 14B:
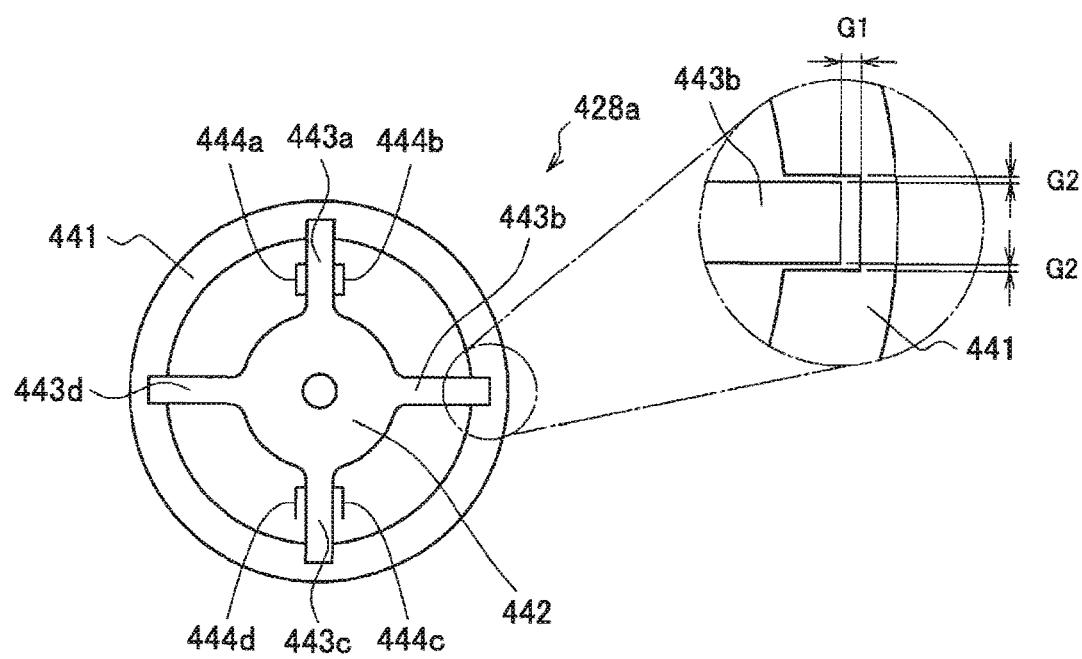
FIG. 14B is a schematic diagram illustrating another exemplary configuration of a torque sensor applied to the actuator illustrated in FIG. 13.

FIG. 14B is a schematic diagram illustrating another exemplary configuration of the torque sensor applied to the actuator 430 illustrated in FIG. 13. Referring to FIG. 14B, a torque sensor 428a according to the present modified example includes an outer ring section 441, an inner ring section 442, beam sections 443a to 443d, and distortion detecting elements 444a to 444d. FIG. 14B schematically illustrates a state of the torque sensor 428a viewed in the axis direction of the driving shaft 429, similarly to FIG. 14A.

In the torque sensor 428a, functions and configurations of the outer ring section 441, the inner ring section 442, the beam sections 443a to 443d, and the distortion detecting elements 444a to 444d are similar to the functions and the configurations of the outer ring section 431, the inner ring section 432, the beam sections 433a to 433d, and the distortion detecting elements 434a to 434d of the torque sensor 428 described above with reference to FIG. 14A. The torque sensor 428a according to the present modified example differs in a configuration of a connection portion of the beam sections 443a to 443d and the outer ring section 441. Thus, the torque sensor 428a illustrated in FIG. 14B will be described focusing on a configuration of the connection portion of the beam sections 443a to 443d and the outer ring section 441 that is the difference with the torque sensor 428 illustrated in FIG. 14A, and a description of a duplicated configuration will be omitted.

Referring to FIG. 14B, the connection portion of the beam section 443b and the outer ring section 441 is enlarged and illustrated together with a general view of the torque sensor 428a. In FIG. 14B, only the connection portion of the beam section 443b and the outer ring section 441 which is one of the four connection portions of the beam sections 443a to 443d and the outer ring section 441 is enlarged and illustrated, but the other 3 connection portions of the beam sections 443a, 443c, and 443d and the outer ring section 441 have the same configuration.

Referring to an enlarged view in FIG. 14B, in the connection portion of the beam section 443b and the outer ring section 441, an engagement concave portion is formed in the outer ring section 441, and the beam section 443b is connected with the outer ring section 441 such that the front edge of the beam section 443b is engaged with the engagement concave portion. Further, gaps G1 and G2 are formed between the beam section 443b and the outer ring section 441. The gap G indicates a gap between the beam section 443b and the outer ring section 441 in a direction in which the beam section 443b extends toward the outer ring section 441, and the gap G2 indicates a gap between the beam section 443b and the outer ring section 441 in a direction orthogonal to that direction.

As described above, in the torque sensor 428a, the beam sections 443a to 443d and the outer ring section 441 are arranged to be separated from each other with the certain gaps G1 and G2. In other words, in the torque sensor 428a, the outer ring section 441 is separated from the inner ring section 442. Thus, since the inner ring section 442 has a degree of freedom of a motion without being bound to the outer ring section 441, for example, even when vibration occurs at the time of driving of the actuator 430, a distortion by vibration can be absorbed by the air gaps G1 and G2 between the inner ring section 442 and the outer ring section 441. Thus, as the torque sensor 428a is applied as the torque sensor of the actuator 430, the generated torque and the external torque are detected with a high degree of accuracy.

For example, JP 2009-269102A and JP 2011-209099A which are patent applications previously filed by the present applicant can be referred to for the configuration of the actuator 430 corresponding to the ideal joint control illustrated in FIGS. 13, 14A, and 14B.

The schematic configuration of the robot arm apparatus 400 according to the present embodiment has been described above with reference to FIGS. 12, 13, 14A, and 14B. Next, the whole body cooperative control and the ideal joint control for controlling driving of the arm unit 420, that is, driving of the joint units 421a to 421f in the robot arm apparatus 400 according to the present embodiment, will be described.

(6-2-2. Generalized Inverse Dynamics)

Next, an overview of the generalized inverse dynamics used for the whole body cooperative control of the robot arm apparatus 400 according to the present embodiment will be described.

The generalized inverse dynamics are basic operations in whole body cooperative control of a multi-link structure of converting purposes of motion related to various dimensions in various kinds of operation spaces into torque to be generated by a plurality of joint units in view of various kinds of constraint conditions in a multi-link structure (for example, the arm unit 420 illustrated in FIG. 12 in the present embodiment) configured such that a plurality of links are connected by a plurality of joint units.

The operation space is an important concept in the force control of the robot apparatus. The operation space is a space for describing a relation between force acting on the multi-link structure and acceleration of the multi-link structure. When the driving control of the multi-link structure is performed by the force control rather than the position control, the concept of the operation space is necessary in the case in which a way of dealing with the multi-link structure and the environment is used as a constraint condition. The operation space is, for example, a space to which the multi-link structure belongs such as a joint space, a Cartesian space, or a momentum space.

The purpose of motion indicates a target value in the driving control of the multi-link structure, and, for example, a target value of a position, a speed, acceleration, force, or an impedance of the multi-link structure that is desired to be achieved through the driving control.

The constraint condition is a constraint condition related to, for example, a position, a speed, acceleration, or force of the multi-link structure that is decided by the shape or the structure of the multi-link structure, the environment around the multi-link structure, a setting performed by the user, or the like. For example, the constraint condition includes information about generated force, a priority, the presence or absence of a non-driven joint, vertical reactive force, a friction weight, a support polygon, and the like.

In the generalized dynamics, in order to achieve both stability of numeric calculation and real-time processable operation efficiency, an operation algorithm is configured with a virtual force decision process (a virtual force calculating process) serving as a first stage and an actual force conversion process (an actual force calculating process) serving as a second stage. In the virtual force calculating process serving as the first stage, virtual force serving as virtual force that is necessary for achieving each purpose of motion and acts on the operation space is decided in view of a priority of a purpose of motion and a maximum value of the virtual force. In the actual force calculating process serving as the second stage, the calculated virtual force is converted into actual force that can be implemented by a configuration of an actual multi-link structure such as joint force or external force in view of a constraint related to a non-driven joint, vertical reactive force, a friction weight, a support polygon, or the like. The virtual force calculating process and the actual force calculating process will be described below. In the following description of the virtual force calculating process, the actual force calculating process, and the ideal joint control, for easier understanding, there are cases in which an exemplary configuration of the arm unit 420 of the robot arm apparatus 400 according to the present embodiment illustrated in FIGS. 12 and 13 is described as a specific example.

(6-2-2-1. Virtual Force Calculating Process)

A vector configured with certain physical quantities in the joint units of the multi-link structure is referred to as a "generalized variable q" (also referred to as a "joint value q" or a "joint space q"). An operation space x is defined by the following Equation (1) using a time differential value of the generalized variable q and a Jacobian J:

[Math 1]
$$\dot{x} = J\dot{q} \qquad (1)$$

In the present embodiment, for example, q indicates a rotational angle in the joint units 421a to 421f of the arm unit 420. An equation of motion related to the operation space x is described by the following Equation (2):

[Math 2]
$$\ddot{x} = \Lambda^{-1} f + c \qquad (2)$$

Here, f indicates force acting on the operation space x. Further, $\Lambda^{-1}$ indicates an operation space inertia inverse matrix, c indicates operation space bias acceleration, and $\Lambda^{-1}$ and c are expressed by the following Equations (3) and (4).

[Math 3]
$$\Lambda^{-1} = JH^{-1}J^T \qquad (3)$$

$$c = JH^{-1}(\tau - b) + \dot{J}\dot{q} \qquad (4)$$

H indicates a joint space inertia matrix, τ indicates joint force (for example, generated torque in the joint units 421a to 421f) corresponding to the joint value q, and b is a term indicating gravity, Coriolis force, or centrifugal force.

In the generalized inverse dynamics, the purpose of motion of the position and the speed related to the operation space x is known to be expressed as acceleration of the operation space x. At this time, in order to implement the operation space acceleration serving as the target value given as the purpose of motion from Equation (1), virtual force $f_v$ that has to act on the operation space x is obtained by solving a sort of linear complementary problem (LCP) expressed by the following Equation (5).

[Math 4]

$$w + \ddot{x} = \Lambda^{-1} f_v + c \qquad (5)$$

$$\text{s.t.} \begin{cases} ((w_i < 0) \cap (f_{v_i} = U_i)) \cup \\ ((w_i > 0) \cap (f_{v_i} = L_i)) \cup \\ ((w_i = 0) \cap (L_i < f_{v_i} < U_i)) \end{cases}$$

Here, $L_i$ and $U_i$ are set to a negative lower limit value (including $-\infty$) of an i-th component of $f_v$ and a positive upper limit value (including $+\infty$) of the i-th component of $f_v$. The LCP can be solved, for example, using an iterative technique, a pivot technique, a method using robust acceleration control, or the like.

Further, the operation space inertia inverse matrix $\Lambda^{-1}$ and the bias acceleration c are large in a calculation cost when they are calculated as in Equations (3) and (4) serving as definitional equations. Thus, a method of performing the calculation process of the operation space inertia inverse matrix $\Lambda^{-1}$ at a high speed by applying a quasidynamics calculation (FWD) of calculating generalized acceleration (joint acceleration) from generalized force (the joint force $\tau$) of the multi-link structure has been proposed. Specifically, the operation space inertia inverse matrix $\Lambda^{-1}$ and the bias acceleration c can be obtained based on information related to force acting on the multi-link structure (for example, the arm unit 420 and the joint units 421*a* to 421*f*) such as the joint space q, the joint force $\tau$, or the gravity g using the forward dynamics calculation FWD. As described above, the operation space inertia inverse matrix $\Lambda^{-1}$ can be calculated with a calculation amount of O(N) on the number N of joint units by applying the forward dynamics calculation FWD related to the operation space.

Here, as a setting example of the purpose of motion, a condition for achieving the target value (indicated by adding a bar above a second order differential of x) of the operation space acceleration by the virtual force $f_{vi}$ of an absolute value $F_i$ or less can be expressed by the following Equation (6):

[Math 5]

$$L_i = -F_i,$$

$$U_i = F_i,$$

$$\ddot{x}_i = \bar{\ddot{x}}_i \qquad (6)$$

As described above, the purpose of motion related to the position and the speed of the operation space x can be represented as the target value of the operation space acceleration and is specifically expressed by the following Equation (7) (the target value of the position and the speed of the operation space x are indicated by adding a bar above x and a first order differential of x).

[Math 6]

$$\bar{\ddot{x}}_i = K_p(\bar{x} - x_i) + K_v(\bar{\dot{x}}_i - \dot{x}_i) \qquad (7)$$

It is also possible to set the purpose of motion related to the operation space (momentum, Cartesian relative coordinates, an interlocked joint, and the like) represented by a linear sum of other operation spaces using an approach of a decomposition operation space. Further, it is necessary to give priorities to competing purposes of motion. The LCP is solved for each priority or in ascending order of priorities, and it is possible to cause virtual force obtained from a previous LCP to act as known external force of a subsequent LCP.

(6-2-2-2. Actual Force Calculating Process)

In the actual force calculating process serving as the second stage of the generalized inverse dynamics, a process of replacing the virtual force $f_v$ obtained in (6-2-1. Virtual force decision process) with actual joint force and external force is performed. A condition of implementing generalized force $\tau_v = J_v^T f_v$ based on virtual force through generated torque $\tau_a$ generated by the joint unit and external force $f_e$ is expressed by the following Equation (8).

[Math 7]

$$\begin{bmatrix} J_{vu}^T \\ J_{va}^T \end{bmatrix} (f_v - \Delta f_v) = \begin{bmatrix} J_{eu}^T \\ J_{ea}^T \end{bmatrix} f_e + \begin{bmatrix} 0 \\ \tau_a \end{bmatrix} \qquad (8)$$

Here, a subscript a indicates a set of driven joint units (a driven joint set), and a subscript u indicates a set of non-driven joint units (a non-driven joint set). In other words, the upper portions in Equation (8) represent balance of force of a space (a non-driven joint space) by the non-driven joint unit, and the lower portions represent balance of force of a space (a driven joint space) by the driven joint unit. $J_{vu}$ and $J_{va}$ indicate a non-driven joint component and a driven joint component of a Jacobian related to the operation space on which the virtual force $f_v$ acts, respectively. $J_{eu}$ and $J_{ea}$ indicate a non-driven joint component and a driven joint component of a Jacobian related to the operation space on which the external force $f_e$ acts. $\Delta f_v$ indicates a component of the virtual force $f_v$ that is hardly implemented by actual force.

The upper portions in Equation (8) are undefined, and, for example, $f_e$ and $\Delta f_v$ can be obtained by solving a quadratic programming problem (QP) expressed by the following Equation (9).

[Math 8]

$$\min \frac{1}{2} \varepsilon^T Q_1 \varepsilon + \frac{1}{2} \xi^T Q_2 \xi \qquad (9)$$

$$\text{s.t. } U\xi \geq v$$

Here, $\varepsilon$ is a difference between sides of the upper portions in Equation (8), and indicates an equation error. $\xi$ is a connection vector of $f_e$ and $\Delta f_v$, and indicates a variable vector. $Q_1$ and $Q_2$ are positive definite symmetric matrices indicating weights at the time of minimization. Further, an inequality constraint of Equation (9) is used to express a constraint condition related to external force such as vertical reactive force, a friction cone, a maximum value of external force, and a support polygon. For example, an inequality constraint related to a rectangular support polygon is expressed by the following Equation (10).

[Math 9]

$$|F_x| \leq \mu_t F_z,$$

$$|F_y| \leq \mu_t F_z,$$

$$F_z \geq 0,$$

$$|M_x| \le d_y F_z,$$

$$|M_y| \le d_x F_z,$$

$$|M_z| \le \mu_r F_z \quad (10)$$

Here, z indicates a normal direction of a contact surface, and x and y indicate two orthogonal tangential directions that are vertical to z. $(F_x, F_y, F_z)$ and $(M_x, M_y, M_z)$ are external force and external force moment acting on a contact point. $\mu_t$ and $\mu_r$ indicate friction coefficients related to translation and rotation. $(d_x, d_y)$ indicates a size of a support polygon.

The solutions $f_e$ and $\Delta f_v$ of a minimum norm or a minimum error are obtained from Equations (9) and (10). It is possible to obtain the joint force $\tau_a$ necessary for implementing the purpose of motion by substituting $f_e$ and $\Delta f_v$ obtained from Equation (9) into the lower portion of Equation (8).

In the case of a system in which the basis is fixed, and there is no non-driven joint, all virtual force can be replaced only with joint force, and $f_e=0$ and $\Delta f_v=0$ can be set in Equation (8). In this case, the following Equation (11) can be obtained for the joint force $\tau_a$ from the lower portions in Equation (8).

[Math 10]

$$\tau_a = J_{va}^T f_v \quad (11)$$

The whole body cooperative control using the generalized inverse dynamics according to the present embodiment has been described above. As described above, as the virtual force calculating process and the actual force calculating process are sequentially performed, it is possible to obtain the joint force $\tau_a$ for achieving a desired purpose of motion. In other words, conversely, as the calculated joint force $\tau_a$ is reflected in a theoretical model in motion of the joint units 421a to 421f, the joint units 421a to 421f are driven to achieve a desired purpose of motion.

Further, for example, JP 2009-95959A and JP 2010-188471A which are patent applications previously filed by the present applicant can be referred to for the whole body cooperative control using the generalized inverse dynamics described above, particularly, for the details of a process of deriving the virtual force $f_v$, a method of solving the LCP and obtaining the virtual force $f_v$, the resolution to the QP problem, and the like.

(6-2-3. Ideal Joint Control)

Next, the ideal joint control according to the present embodiment will be described. Motion of each of the joint units 421a to 421f is modelized by an equation of motion of a second order delay system of the following Equation (12):

[Math 11]

$$I_a \ddot{q} = \tau_a + \tau_e - v_a \dot{q} \quad (12)$$

Here, $I_a$ indicates an inertia moment (inertia) in a joint unit, $\tau_a$ indicates generated torque of the joint units 421a to 421f, $\tau_e$ indicates external torque acting on each of the joint units 421a to 421f, and $v_a$ indicates a viscous drag coefficient in each of the joint units 421a to 421f. Equation (12) can also be regarded as a theoretical model representing motion of the actuator 430 in the joint units 421a to 421f.

As described above in (6-2-2. Generalized inverse dynamics), through the calculation using the generalized inverse dynamics, it is possible to calculate $\tau_a$ serving as actual force that each of the joint units 421a to 421f has to use to implement the purpose of motion using the purpose of motion and the constraint condition. Thus, ideally, a response according to the theoretical model expressed by Equation (12) is implemented, that is, a desired purpose of motion is achieved by applying each calculated $\tau_a$ to Equation (12).

However, practically, there are cases in which an error (a modelization error) between motion of the joint units 421a to 421f and the theoretical model expressed by Equation (12) occurs due to influence of various disturbances. The modelization error is classified into an error caused by a mass property such as a weight, a center of gravity, or a tensor of inertia of the multi-link structure and an error caused by friction, inertia, or the like in the joint units 421a to 421f. Of these, the modelization error of the former caused by the mass property can be relatively easily reduced at the time of construction of the theoretical model by applying high-accuracy computer aided design (CAD) data or an identification method.

Meanwhile, the modelization error of the latter caused by friction, inertia, or the like in the joint units 421a to 421f occurs due to a phenomenon that it is difficult to modelize, for example, friction or the like in the reduction gear 426 of the joint units 421a to 421f, and an unignorable modelization error may remain at the time of construction of the theoretical model. Further, there is likely to be an error between a value of an inertia $I_a$ or a viscous drag coefficient $v_a$ in Equation (12) and an actual value in the joint units 421a to 421f. The error that is hardly modelized may act as a disturbance in the driving control of the joint units 421a to 421f. Thus, due to influence of such a disturbance, practically, there are cases in which motion of the joint units 421a to 421f does not respond as in the theoretical model expressed by Equation (12). Thus, there are cases in which it is difficult to achieve the purpose of motion of the control target even when the actual force $\tau_a$ serving as the joint force calculated by the generalized inverse dynamics is applied. In the present embodiment, an active control system is added to each of the joint units 421a to 421f, and thus the response of the joint units 421a to 421f is considered to be corrected such that an ideal response according to the theoretical model expressed by Equation (12) is performed. Specifically, in the present embodiment, torque control of a friction compensation type using the torque sensors 428 and 428a of the joint units 421a to 421f is performed, and in addition, it is possible to perform an ideal response according to an ideal value even on the inertia $I_a$ and the viscous drag coefficient $v_a$ for the requested generated torque $\tau_a$ and the requested external torque $\tau_e$.

In the present embodiment, controlling driving of the joint unit such that the joint units 421a to 421f of the robot arm apparatus 400 perform the ideal response expressed by Equation (12) is referred to as the ideal joint control as described above. Here, in the following description, an actuator whose driving is controlled by the ideal joint control is also referred to as a "virtualized actuator (VA)" since the ideal response is performed. The ideal joint control according to the present embodiment will be described below with reference to FIG. 15.

Figure 15:
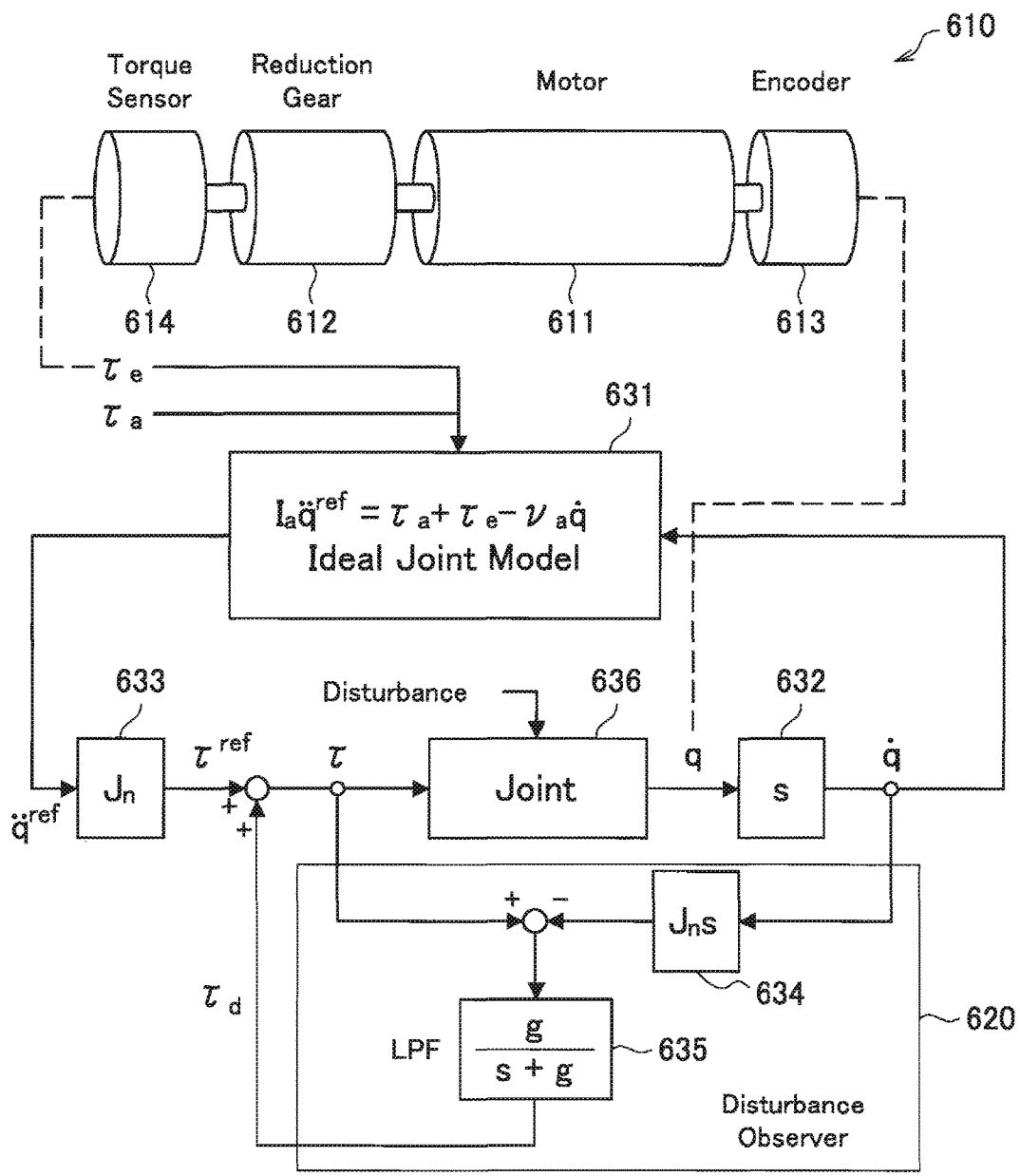
FIG. 15 is an explanatory diagram for describing ideal joint control according to an embodiment of the present disclosure.

FIG. 15 is an explanatory diagram for describing the ideal joint control according to an embodiment of the present disclosure. FIG. 15 schematically illustrates a conceptual computing unit that performs various kinds of operations according to the ideal joint control using blocks.

Referring to FIG. 15, an actuator 610 schematically illustrates a mechanism of the actuator 430 illustrated in FIG. 13, and a motor 611, a reduction gear 612, an encoder 613, and a torque sensor 614 correspond to the motor 424, the reduction gear 426, the encoder 427, and the torque sensor 428 (or the torque sensor 428a illustrated in FIG. 714B) which are illustrated in FIG. 13.

Here, when the actuator 610 performs the response according to the theoretical model expressed by Equation (12), it means that the rotational angular acceleration at the left side is achieved when the right side of Equation (12) is given. Further, as expressed in Equation (12), the theoretical model includes an external torque term $\tau_e$ acting on the actuator 610. In the present embodiment, in order to perform the ideal joint control, the external torque $\tau_c$ is measured by the torque sensor 614. Further, a disturbance observer 620 is applied to calculate a disturbance estimation value $\tau_d$ serving as an estimation value of torque caused by a disturbance based on a rotational angle q of the actuator 610 measured by the encoder 613.

A block 631 represents a computing unit that performs an operation according to the ideal joint model of the joint units 421a to 421f expressed by Equation (12). The block 631 can receive the generated torque $\tau_a$, the external torque $\tau_e$, and the rotational angular velocity (the first order differential of the rotational angle q) and output the rotational angular acceleration target value (a second order differential of a rotational angle target value $q^{ref}$) shown at the left side of Equation (12).

In the present embodiment, the generated torque $\tau_a$ calculated by the method described in (6-2-2. Generalized inverse dynamics) and the external torque $\tau_e$ measured by the torque sensor 614 are input to the block 631. Meanwhile, the rotational angle q measured by the encoder 613 is input to a block 632 indicating a computing unit that performs differential operation, and thus the rotational angular velocity (the first order differential of the rotational angle q) is calculated. In addition to the generated torque $\tau_a$ and the external torque $\tau_e$, the rotational angular velocity calculated by the block 632 is input to the block 631, and thus the rotational angular acceleration target value is calculated by the block 631. The calculated rotational angular acceleration target value is input to a block 633.

The block 633 indicates a computing unit that calculates torque to be generated in the actuator 610 based on the rotational angular acceleration of the actuator 610. In the present embodiment, specifically, the block 633 can obtain a torque target value $\tau^{ref}$ by multiplying a nominal inertia $J_n$ of the actuator 610 to the rotational angular acceleration target value. In the ideal response, a desired purpose of motion is achieved by causing the actuator 610 to generate the torque target value $\tau^{ref}$, but there are cases in which an actual response is influenced by a disturbance or the like as described above. Thus, in the present embodiment, the disturbance estimation value $\tau_d$ is calculated by the disturbance observer 620, and the torque target value $\tau^{ref}$ is corrected using the disturbance estimation value $\tau_d$.

A configuration of the disturbance observer 620 will be described. As illustrated in FIG. 15, the disturbance observer 620 calculates the disturbance estimation value $\tau_d$ based on a torque command value $\tau$ and the rotational angular velocity calculated from the rotational angle q measured by the encoder 613. Here, the torque command value $\tau$ is a torque value to be finally generated by the actuator 610 after influence of the disturbance is corrected. For example, when no disturbance estimation value $\tau_d$ is calculated, the torque command value $\tau$ is used as the torque target value $\tau^{ref}$.

The disturbance observer 620 is configured with a block 634 and a block 635. The block 634 is a computing unit that calculates torque to be generated by the actuator 610 based on the rotational angular velocity of the actuator 610. In the present embodiment, specifically, the rotational angular velocity calculated by the block 632 based on the rotational angle q measured by the encoder 613 is input to the block 634. The block 634 can obtain the rotational angular acceleration by performing an operation expressed by a transfer function $J_n s$, that is, by differentiating the rotational angular velocity, and calculate an estimation value (a torque estimation value) of torque actually acting on the actuator 610 by multiplying the calculated rotational angular acceleration by the nominal inertia $J_n$.

In the disturbance observer 620, a difference between the torque estimation value and the torque command value $\tau$ is obtained, and thus the disturbance estimation value $\tau_d$ serving as a value of torque by a disturbance is estimated. Specifically, the disturbance estimation value $\tau_d$ may be a difference between the torque command value $\tau$ in the previous control and the torque estimation value in the current control. Since the torque estimation value calculated by the block 634 is based on an actual measurement value, and the torque command value $\tau$ calculated by the block 633 is based on the ideal theoretical model of the joint units 421a to 421f indicated by the block 631, it is possible to estimate influence of a disturbance that is not considered in the theoretical model by obtaining the difference of the two values.

The disturbance observer 620 is further provided with a low pass filter (LPF) indicated by the block 635 in order to prevent a divergence of a system. The block 635 performs an operation represented by a transfer function $g/(s+g)$, outputs only a low frequency component in response to an input value, and stabilizes a system. In the present embodiment, a difference value between the torque estimation value calculated by the block 634 and the torque command value $\tau^{ref}$ is input to the block 635, and the low frequency component is calculated as the disturbance estimation value $\tau_d$.

In the present embodiment, feedforward control of adding the disturbance estimation value $\tau_d$ calculated by the disturbance observer 620 to the torque target value $\tau^{ref}$ is performed, and thus the torque command value $\tau$ serving as a torque value to be finally generated by the actuator 610 is calculated. Then, the actuator 610 is driven based on the torque command value $\tau$. Specifically, the torque command value $\tau$ is converted into a corresponding electric current value (an electric current command value), the electric current command value is applied to the motor 611, so that the actuator 610 is driven.

By employing the configuration described above with reference to FIG. 15, in the driving control of the joint units 421a to 421f according to the present embodiment, even when there is a disturbance component such as friction, it is possible for the response of the actuator 610 to follow the target value. Further, it is possible to perform the ideal response according to the inertia $I_a$ and the viscous drag coefficient $v_a$ assumed by the theoretical model in the driving control of the joint units 421a to 421f.

For example, JP 2009-269102A that is a patent application previously filed by the present applicant can be referred to for the details of the above-described ideal joint control.

The ideal joint control according to the present embodiment has been described above with reference to FIG. 15 together with the generalized inverse dynamics used in the present embodiment. As described above, in the present embodiment, the whole body cooperative control of calculating driving parameters (for example, the generated torque values of the joint units 421a to 421f) of the joint units 421a to 421f for achieving the purpose of motion of the arm unit 420 is performed in view of the constraint condition using the generalized inverse dynamics. Further, as described above with reference to FIG. 15, in the present embodiment, as correction in which influence of a disturbance is considered is performed on the generated torque value calculated by the whole body cooperative control using the generalized inverse dynamics, the ideal joint control of implementing the ideal response based on the theoretical model in the driving control of the joint units 421*a* to 421*f* is performed. Thus, in the present embodiment, it is possible to perform high-accuracy driving control for achieving the purpose of motion for driving of the arm unit 420.

(6-2-4. Configuration of Robot Arm Control System)

Next, a configuration of the robot arm control system according to the present embodiment in which the whole body cooperative control and the ideal joint control described in (6-2-2. Generalized inverse dynamics) and (6-2-3. Ideal joint control) are applied to the driving control of the robot arm apparatus will be described.

Figure 16:
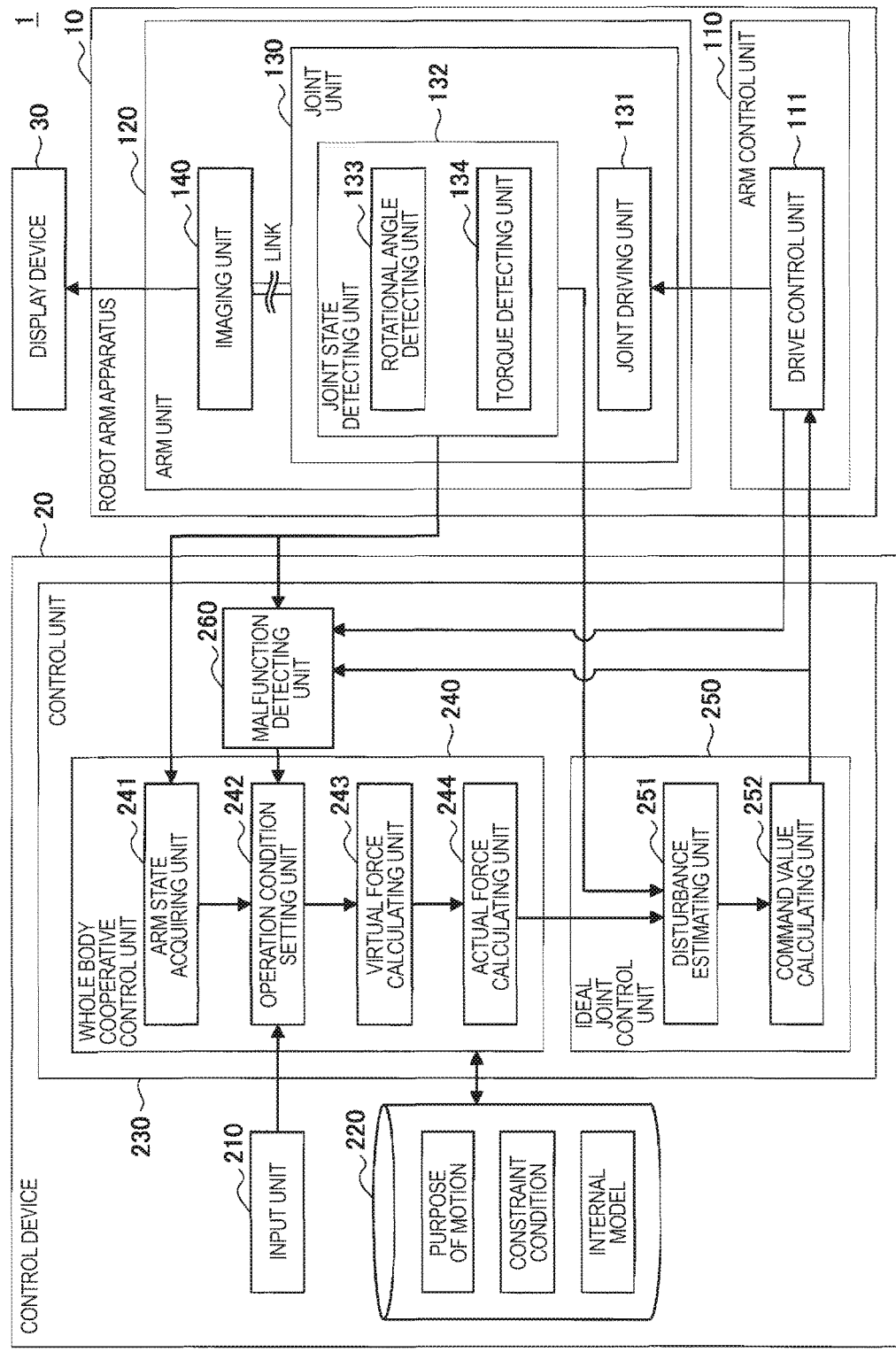
FIG. 16 is a functional block diagram illustrating an exemplary configuration of a robot arm control system according to an embodiment of the present disclosure.

An exemplary configuration of the robot arm control system according to an embodiment of the present disclosure will be described with reference to FIG. 16. FIG. 16 is a functional block diagram illustrating an exemplary configuration of the robot arm control system according to an embodiment of the present disclosure. In the robot arm control system illustrated in FIG. 16, components related to driving control of the arm unit of the robot arm apparatus are mainly illustrated.

Referring to FIG. 16, a robot arm control system 1 according to an embodiment of the present disclosure includes a robot arm apparatus 10, a control device 20, and a display device 30. In the present embodiment, various kinds of operations in the whole body cooperative control described in (6-2-2. Generalized inverse dynamics) and the ideal joint control described in (6-2-3. Ideal joint control) through the control device 20 are performed, and driving of the arm unit of the robot arm apparatus 10 is controlled based on the operation result. Further, the arm unit of the robot arm apparatus 10 is provided with an imaging unit 140 which will be described later, and an image captured by the imaging unit 140 is displayed on a display screen of the display device 30. Next, configurations of the robot arm apparatus 10, the control device 20, and the display device 30 will be described in detail. Note that the robot arm control system 1 illustrated in FIG. 16 corresponds to the robot arm control system 2 described with reference to FIG. 1, and the robot arm control system 1 illustrated in FIG. 16 is a more detailed diagram in which a structural element relating to drive control of the robot arm apparatus 10 that is omitted in FIG. 1 is illustrated in detail with respect to the robot arm control system 2.

The robot arm apparatus 10 includes an arm unit having a multi-link structure configured with a plurality of joint units and a plurality of links, and drives the arm unit in the movable range to control the position and posture of the front edge unit installed at the front edge of the arm unit. The robot arm apparatus 10 corresponds to the robot arm apparatus 400 illustrated in FIG. 12.

Referring to FIG. 16, the robot arm apparatus 10 includes an arm control unit 110 and an arm unit 120. The arm unit 120 includes a joint unit 130 and the imaging unit 140.

The arm control unit 110 controls the robot arm apparatus 10 in an integrated manner, and controls driving of the arm unit 120. The arm control unit 110 corresponds to the control unit (not illustrated in FIG. 12) described above with reference to FIG. 12. Specifically, the arm control unit 110 includes a drive control unit 111, and controls driving of the arm unit 120, and driving of the arm unit 120 is controlled by controlling driving of the joint unit 130 according to control of the drive control unit 111. More specifically, the drive control unit 111 controls the number of revolutions of the motor in the actuator of the joint unit 130 and the rotational angle and the generated torque of the joint unit 130 by controlling an amount of electric current supplied to the motor. Here, as described above, driving control of the arm unit 120 by the drive control unit 111 is performed based on the operation result in the control device 20. Thus, an amount of electric current that is controlled by the drive control unit 111 and supplied to the motor in the actuator of the joint unit 130 is an amount of electric current decided based on the operation result in the control device 20. However, in the present embodiment, as illustrated in FIG. 1, the joint control unit 135 may also be provided in each joint unit 130, and the driving of joint unit 130 may be controlled by the joint control unit 135.

The arm unit 120 has a multi-link structure configured with a plurality of joint units and a plurality of links, and driving of the arm unit 120 is controlled according to control of the arm control unit 110. The arm unit 120 corresponds to the arm unit 420 illustrated in FIG. 12. The arm unit 120 includes the joint unit 130 and the imaging unit 140. Further, since the plurality of joint units of the arm unit 120 have the same function and configuration, a configuration of one joint unit 130 representing the plurality of joint units is illustrated in FIG. 16.

The joint unit 130 connects links to be rotatable in the arm unit 120, and the rotary driving of the joint unit 130 is controlled according to control of the arm control unit 110 such that the arm unit 120 is driven. The joint unit 130 corresponds to the joint units 421*a* to 421*f* illustrated in FIG. 12. Further, the joint unit 130 includes an actuator, and the actuator has a configuration similar to, for example, the configuration illustrated in FIGS. 13, 14A, and 14B.

The joint unit 130 includes a joint driving unit 131 and a joint state detecting unit 132.

The joint driving unit 131 is a driving mechanism in the actuator of the joint unit 130, and as the joint driving unit 131 is driven, the joint unit 130 is rotationally driven. The drive control unit 111 controls driving of the joint driving unit 131. For example, the joint driving unit 131 is a component corresponding to the motor 424 and the motor driver 425 illustrated in FIG. 13, and driving the joint driving unit 131 corresponds to the motor driver 425 driving the motor 424 with an amount of electric current according to a command given from the drive control unit 111.

The joint state detecting unit 132 detects the state of the joint unit 130. Here, the state of the joint unit 130 may mean a motion state of the joint unit 130. For example, the state of the joint unit 130 includes information such as the rotational angle, the rotational angular velocity, the rotational angular acceleration, and the generated torque of the joint unit 130. In the present embodiment, the joint state detecting unit 132 includes a rotational angle detecting unit 133 that detects the rotational angle of the joint unit 130 and a torque detecting unit 134 that detects the generated torque and the external torque of the joint unit 130. The rotational angle detecting unit 133 and the torque detecting unit 134 correspond to the encoder 427 of the actuator 430 illustrated in FIG. 13 and the torque sensors 428 and 428*a* illustrated in FIGS. 14A and 14B. The joint state detecting unit 132 transmits the detected state of the joint unit 130 to the control device 20.

Note that, FIG. 16 illustrates the rotational angle detecting unit 133 and the torque detecting unit 134 that are functions of acquiring information mainly indicating motion of the arm unit 120 as an example of a function of the joint state detecting unit 132 in order to describe control quantity operating process in the whole body cooperative control. In the present embodiment, the joint state detecting unit 132 may include respective sensors provided in the actuator 180 illustrated in FIG. 6. For example, the rotational angle detecting unit 133 may include the motor angle sensor 184a and the output shaft angle sensor 184b illustrated in FIG. 6. The torque detecting unit 134 may include the torque sensor 183 illustrated in FIG. 6. The joint state detecting unit 132 may further include, for example, a function of detecting another physical quantity corresponding to each sensor of the actuator 180, such as a function of detecting current provided to the motor, or a function of detecting a temperature around the motor.

The imaging unit 140 is an example of the front edge unit (corresponding to the front edge unit 145 illustrated in FIG. 1) installed at the front edge of the arm unit 120, and acquires an image of a photographing target. The imaging unit 140 corresponds to the imaging unit 423 illustrated in FIG. 12. Specifically, the imaging unit 140 is, for example, a camera capable of photographing a photographing target in a moving image format or a still image format. More specifically, the imaging unit 140 includes a plurality of light receiving elements arranged two dimensionally, and can perform photoelectric conversion in the light receiving elements and acquire an image signal indicating an image of a photographing target. The imaging unit 140 transmits the acquired image signal to the display device 30.

Further, similarly to the robot arm apparatus 400 of FIG. 12 in which the imaging unit 423 is installed at the front edge of the arm unit 420, in the robot arm apparatus 10, the imaging unit 140 is actually installed at the front edge of the arm unit 120. In FIG. 16, the form in which the imaging unit 140 is installed at the front edge of the last link through the plurality of joint units 130 and a plurality of links is represented by schematically illustrating the link between the joint unit 130 and the imaging unit 140.

Note that the front edge unit provided on the front edge of the arm unit 120 is not limited to being the imaging unit 140. In the present embodiment, various kinds of medical apparatuses may be connected to the front edge of the arm unit 120 as the front edge unit. As the medical apparatus, for example, there are various kinds of units used when the medical procedure is performed such as various kinds of medical procedure instruments including a scalpel or forceps or one unit of various kinds of examination apparatuses including a probe of an ultrasonic examination apparatus. Further, in the present embodiment, the imaging unit 140 illustrated in FIG. 16 or a unit having an imaging function such as an endoscope or a microscope may also be included as a medical apparatus. As described above, the robot arm apparatus 10 according to the present embodiment may be a medical robot arm apparatus including a medical apparatus. Similarly, the robot arm control system 1 according to the present embodiment may be a medical robot arm control system. Note that the robot arm apparatus 10 illustrated in FIG. 16 may also be said to be a video microscope robot arm apparatus equipped with a unit having an imaging function as the front edge unit. Further, a stereo camera including two imaging units (camera units) may be installed at the front edge of the arm unit 120, and photography may be performed so that an imaging target is displayed as a 3D image.

The function and configuration of the robot arm apparatus 10 have been described above. Next, a function and configuration of the control device 20 will be described. Referring to FIG. 16, the control device 20 includes an input unit 210, a storage unit 220, and a control unit 230.

The control unit 230 controls the control device 20 in an integrated manner, and performs various kinds of operations for controlling driving of the arm unit 120 in the robot arm apparatus 10. Specifically, in order to control driving of the arm unit 120 of the robot arm apparatus 10, the control unit 230 performs various kinds of operations in the whole body cooperative control and the ideal joint control. The function and configuration of the control unit 230 will be described below in detail, but the whole body cooperative control and the ideal joint control have already been described in (6-2-2. Generalized inverse dynamics) and (6-2-3. Ideal joint control), and thus a description thereof will be omitted here.

The control unit 230 includes a whole body cooperative control unit 240, an ideal joint control unit 250, and a malfunction detecting unit 260.

The whole body cooperative control unit 240 performs various kinds of operations related to the whole body cooperative control using the generalized inverse dynamics. In the present embodiment, the whole body cooperative control unit 240 acquires a state (an arm state) of the arm unit 120 based on the state of the joint unit 130 detected by the joint state detecting unit 132. Further, the whole body cooperative control unit 240 calculates a control value for the whole body cooperative control of the arm unit 120 in the operation space based on the arm state and the purpose of motion and the constraint condition of the arm unit 120 using the generalized inverse dynamics. For example, the operation space refers to a space for describing a relation between force acting on the arm unit 120 and acceleration generated in the arm unit 120.

The whole body cooperative control unit 240 includes an arm state acquiring unit 241, an operation condition setting unit 242, a virtual force calculating unit 243, and an actual force calculating unit 244. Herein, in FIG. 1 discussed earlier, the operation condition setting unit 242 is illustrated as a function not included in the whole body cooperative control unit 240 for the sake of convenience, but these units have similar functions.

The arm state acquiring unit 241 acquires the state (the arm state) of the arm unit 120 based on the state of the joint unit 130 detected by the joint state detecting unit 132. Here, the arm state may mean the motion state of the arm unit 120. For example, the arm state includes information such as a position, a speed, acceleration, or force of the arm unit 120. As described above, the joint state detecting unit 132 acquires information such as the rotational angle, the rotational angular velocity, the rotational angular acceleration, or the generated torque of each of the joint units 130 as the state of the joint unit 130. Further, as will be described later, the storage unit 220 stores various kinds of information that is processed by the control device 20, and in the present embodiment, the storage unit 220 may store various kinds of information (arm information) related to the arm unit 120, for example, the number of joint units 130 and the number of links configuring the arm unit 120, a connection state of the link and the joint unit 130, and the length of the link. The arm state acquiring unit 241 can acquire the corresponding information from the storage unit 220. Thus, the arm state acquiring unit 241 can acquire information such as the positions (coordinates) of the plurality of joint units 130, a plurality of links, and the imaging unit 140 on the space (that is, the shape of the arm unit 120 or the position and posture of the imaging unit 140) or force acting on each of the joint units 130, the link, and the imaging unit 140 based on the state of the joint unit 130 and the arm information. The arm state acquiring unit 241 transmits the acquired arm information to the operation condition setting unit 242.

The operation condition setting unit 242 sets an operation condition in an operation related to the whole body cooperative control using the generalized inverse dynamics. Here, the operation condition may be the purpose of motion and the constraint condition. The purpose of motion may be various kinds of information related to a motion of the arm unit 120. Specifically, the purpose of motion may be a target value of the position and posture (coordinates), a speed, acceleration, and force of the imaging unit 140 or a target value of the position (coordinates), a speed, acceleration, and force of the plurality of joint units 130 and a plurality of links of the arm unit 120. The constraint condition may be various kinds of information for constricting the motion of the arm unit 120. Specifically, the constraint condition may be coordinates of a region into which none of the components of the arm unit should move, values of a speed and acceleration at which the arm unit should not move, a value of force that should not be generated, or the like. Further, a constraint range of various kinds of physical quantities in the constraint condition may be set from ones that are difficult for the arm unit 120 to implement structurally or may be appropriately set by the user. Further, the operation condition setting unit 242 includes a physical model (For example, one in which the number of links configuring the arm unit 120, the length of the link, the connection state of the link through the joint unit 130, the movable range of the joint unit 130, and the like are modelized. This corresponds to an internal model.) for the structure of the arm unit 120, and may set the motion condition and the constraint condition by generating a control model in which a desired motion condition and a desired constraint condition are reflected in the physical model.

In the present embodiment, it is possible to appropriately set the purpose of motion and the constraint condition and cause the arm unit 120 to perform a desired movement. For example, it is possible to set the target value of the position of the imaging unit 140 as the purpose of motion and move the imaging unit 140 to the target position, and it is also possible to set a movement constraint according to the constraint condition, for example, to prevent the arm unit 120 from invading a certain region in a space and then drive the arm unit 120.

As a specific example of the purpose of motion, for example, the purpose of motion may be a pivot movement serving as a turning movement in which the imaging unit 140 moves within a plane of a cone having a medical procedure part as an apex, and an axis of the cone is used as a pivot axis in a state in which the photographing direction of the imaging unit 140 is fixed to the medical procedure part. For example, by setting a constraint condition that the orientation of the imaging unit 140 is locked to a certain point in space (in other words, a certain point in space is positioned on the optical axis of the imaging unit 140), a pivot operation in which the imaging unit 140 moves over the surface of a cone whose apex is the certain point may be realized. In the pivot movement, the turning movement may be performed in a state in which a distance between the imaging unit 140 and a point corresponding to the apex of the cone is maintained constant. As the pivot movement is performed, it is possible to observe an observation part at an equal distance and at different angles, and thus it is possible to improve a convenience of the user performing surgery.

Another specific example, the purpose of motion may be content controlling the generated torque in each of the joint units 130. Specifically, the purpose of motion may be a power assist movement of controlling the state of the joint unit 130 such that gravity acting on the arm unit 120 is negated and controlling the state of the joint unit 130 such that movement of the arm unit 120 is supported in a direction of force given from the outside. More specifically, in the power assist movement, driving of each of the joint units 130 is controlled such that each of the joint units 130 generates the generated torque for negating external torque by gravity in each of the joint units 130 of the arm unit 120, and thus the position and posture of the arm unit 120 are held in a certain state. When external torque is further applied from the outside (for example, from the user) in this state, driving of each of the joint units 130 is controlled such that each of the joint units 1 generates the generated torque in the same direction as the applied external torque. As the power assist movement is performed, when the user manually moves the arm unit 120, the user can move the arm unit 120 by small force, and thus a feeling of moving the arm unit 120 in a non-gravity state can be given to the user. Further, it is possible to combine the pivot movement with the power assist movement.

Here, in the present embodiment, the purpose of motion may mean a movement (motion) of the arm unit 120 implemented in the whole body cooperative control or may mean an instantaneous purpose of motion (that is, the target value in the purpose of motion) in the corresponding movement. For example, in the case of the pivot movement, performing the pivot movement by the imaging unit 140 is the purpose of motion, but, for example, a value of the position or the speed of the imaging unit 140 in the cone plane in the pivot movement is set as an instantaneous purpose of motion (the target value in the purpose of motion) while the pivot movement is being performed. Further, for example, in the case of the power assist movement, performing the power assist movement for supporting movement of the arm unit 120 in the direction of force applied from the outside is the purpose of motion, but a value of the generated torque in the same direction as the external torque applied to each of the joint units 130 is set as an instantaneous purpose of motion (the target value in the purpose of motion) while the power assist movement is being performed. In the present embodiment, the purpose of motion is a concept including both the instantaneous purpose of motion (for example, the target value of the position, the speed, or force of each component of the arm unit 120 during a certain period of time) and movement of each component of the arm unit 120 implemented over time as a result of continuously achieving the instantaneous purpose of motion. In each step in an operation for the whole body cooperative control in the whole body cooperative control unit 240, the instantaneous purpose of motion is set each time, and the operation is repeatedly performed, so that a desired purpose of motion is finally achieved.

Further, in the present embodiment, when the purpose of motion is set, the viscous drag coefficient in the rotary motion of each of the joint units 130 may be appropriately set as well. As described above, the joint unit 130 according to the present embodiment is configured to be able to appropriately adjust the viscous drag coefficient in the rotary motion of the actuator 430. Thus, as the viscous drag coefficient in the rotary motion of each of the joint units 130 is also set at the time of setting of the purpose of motion, for example, it is possible to implement the state in which rotation is easily or not easily performed by force applied from the outside. For example, in the case of the power assist movement, as the viscous drag coefficient in the joint unit 130 is set to be small, the user can move the arm unit 120 by small force, and the user can have a non-gravity feeling. As described above, the viscous drag coefficient in the rotary motion of each of the joint units 130 may be appropriately set according to content of the purpose of motion.

The specific examples of the purpose of motion will be described again in detail in (6-2-5. Specific example of purpose of motion).

Here, in the present embodiment, as will be described later, the storage unit 220 may store a parameter related to the operation condition such as the purpose of motion or the constraint condition used in an operation related to the whole body cooperative control. The operation condition setting unit 242 can set the constraint condition stored in the storage unit 220 as the constraint condition used in the operation of the whole body cooperative control.

Further, in the present embodiment, the operation condition setting unit 242 can set the purpose of motion by a plurality of methods. For example, the operation condition setting unit 242 may set the purpose of motion based on the arm state transmitted from the arm state acquiring unit 241. As described above, the arm state includes information of the position of the arm unit 120 and information of force acting on the arm unit 120. Thus, for example, when the user manually moves the arm unit 120, information related to how the user moves the arm unit 120 is also acquired as the arm state through the arm state acquiring unit 241. Thus, the operation condition setting unit 242 can set, for example, the position to which the user has moved the arm unit 120, a speed at which the user has moved the arm unit 120, or force by which the user has moved the arm unit 120 as the instantaneous purpose of motion based on the acquired arm state. As the purpose of motion is set as described above, control is performed such that driving of the arm unit 120 follows and supports movement of the arm unit 120 by the user.

Further, for example, the operation condition setting unit 242 may set the purpose of motion based on an instruction input from the input unit 210 by the user. As will be described later, the input unit 210 is an input interface through which the user inputs, for example, information or a command related to driving control of the robot arm apparatus 10 to the control device 20, and in the present embodiment, the purpose of motion may be set based on an operation input from the input unit 210 by the user. Specifically, the input unit 210 includes an operation unit operated by the user such as a lever or a pedal, and, for example, the operation condition setting unit 242 may set the position or the speed of each component of the arm unit 120 as the instantaneous purpose of motion according to an operation of the lever, the pedal, or the like.

Further, for example, the operation condition setting unit 242 may set the purpose of motion stored in the storage unit 220 as the purpose of motion used in the operation of the whole body cooperative control. For example, in the case of the purpose of motion for causing the imaging unit 140 to stop at a certain point in the space, coordinates of the certain point can be set as the purpose of motion in advance. Further, for example, in the case of the purpose of motion for causing the imaging unit 140 to move along a certain trajectory in the space, coordinates of points indicating the certain trajectory can be set as the purpose of motion in advance. As described above, when the purpose of motion can be set in advance, the purpose of motion may be stored in the storage unit 220 in advance. Further, for example, in the case of the pivot movement, the purpose of motion is limited to setting a position, a speed, or the like in the plane of the cone as the target value, and in the case of the power assist movement, the purpose of motion is limited to setting force as the target value. As described above, when the purpose of motion such as the pivot movement or the power assist movement is set in advance, for example, information related to a range or a type of the target value that can be set as the instantaneous purpose of motion in the purpose of motion may be stored in the storage unit 220. The operation condition setting unit 242 can include and set various kinds of information related to the purpose of motion as the purpose of motion.

Further, the user may appropriately set the method of setting the purpose of motion through the operation condition setting unit 242, for example, according to the purpose of the robot arm apparatus 10. Further, the operation condition setting unit 242 may set the purpose of motion and the constraint condition by appropriately combining the above methods. Furthermore, a priority of the purpose of motion may be set to the constraint condition stored in the storage unit 220, and when there are a plurality of different purposes of motion, the operation condition setting unit 242 may set the purpose of motion according to the priority of the constraint condition. The operation condition setting unit 242 transmits the arm state, the set purpose of motion and the constraint condition to the virtual force calculating unit 243.

The virtual force calculating unit 243 calculates virtual force in the operation related to the whole body cooperative control using the generalized inverse dynamics. For example, a virtual force calculation process performed by the virtual force calculating unit 243 may be a series of processes described above in (6-2-2-1. Virtual force calculating process). The virtual force calculating unit 243 transmits the calculated virtual force $f_v$ to the actual force calculating unit 244.

The actual force calculating unit 244 calculates actual force in the operation related to the whole body cooperative control using the generalized inverse dynamics. For example, an actual force calculation process performed by the actual force calculating unit 244 may be a series of processes described above in (6-2-2-2. Actual force calculating process). The actual force calculating unit 244 transmits the calculated actual force (the generated torque) $\tau_a$ to the ideal joint control unit 250. Further, in the present embodiment, the generated torque $\tau_a$ calculated by the actual force calculating unit 244 is also referred to as a "control value" or a "control torque value" to mean a control value of the joint unit 130 in the whole body cooperative control.

The ideal joint control unit 250 performs various kinds of operations related to the ideal joint control for implementing the ideal response based on the theoretical model. In the present embodiment, the ideal joint control unit 250 corrects influence of a disturbance on the generated torque $\tau_a$ calculated by the actual force calculating unit 244, and calculates the torque command value $\tau$ for implementing the ideal response of the arm unit 120. The operation process performed by the ideal joint control unit 250 corresponds to a series of processes described above in (6-2-3. Ideal joint control).

The ideal joint control unit 250 includes a disturbance estimating unit 251 and a command value calculating unit 252.

The disturbance estimating unit 251 calculates the disturbance estimation value $\tau_d$ based on the torque command value $\tau$ and the rotational angular velocity calculated from the rotational angle q detected by the rotational angle detecting unit 133. Here, the torque command value $\tau$ refers to the command value indicating the generated torque of the arm unit 120 that is finally transmitted to the robot arm apparatus 10. As described above, the disturbance estimating unit 251 has a function corresponding to the disturbance observer 620 illustrated in FIG. 15.

The command value calculating unit 252 calculates the torque command value $\tau$ serving as the command value indicating torque that is generated by the arm unit 120 and finally transmitted to the robot arm apparatus 10 using the disturbance estimation value $\tau_d$ calculated by the disturbance estimating unit 251. Specifically, the command value calculating unit 252 calculates the torque command value $\tau$ by adding the disturbance estimation value $\tau_d$ calculated by the disturbance estimating unit 251 to $\tau^{ref}$ calculated from the ideal model of the joint unit 130 expressed by Equation (12). For example, when the disturbance estimation value $\tau_d$ is not calculated, the torque command value $\tau$ is used as the torque target value $\tau^{ref}$. As described above, the function of the command value calculating unit 252 corresponds to a function other than that of the disturbance observer 620 illustrated in FIG. 15.

As described above, in the ideal joint control unit 250, a series of processes described above with reference to FIG. 15 is performed such that information is repeatedly exchanged between the disturbance estimating unit 251 and the command value calculating unit 252. The ideal joint control unit 250 transmits the calculated torque command value $\tau$ to the drive control unit 111 of the robot arm apparatus 10. The drive control unit 111 performs control of supplying an amount of electric current corresponding to the transmitted torque command value $\tau$ to the motor in the actuator of the joint unit 130, controls the number of revolutions of the motor, and controls the rotational angle and the generated torque of the joint unit 130.

In the robot arm control system 1 according to the present embodiment, since driving control of the arm unit 120 in the robot arm apparatus 10 is continuously performed while a task using the arm unit 120 is being performed, the above-described process is repeatedly performed in the robot arm apparatus 10 and the control device 20. In other words, the joint state detecting unit 132 of the robot arm apparatus 10 detects the state of the joint unit 130, and transmits the detected state of the joint unit 130 to the control device 20. In the control device 20, various kinds of operations related to the whole body cooperative control and the ideal joint control for controlling driving of the arm unit 120 are performed based on the state of the joint unit 130, the purpose of motion, and the constraint condition, and the torque command value $\tau$ serving as the operation result is transmitted to the robot arm apparatus 10. In the robot arm apparatus 10, driving of the arm unit 120 is controlled based on the torque command value $\tau$, and the state of the joint unit 130 during or after driving is detected by the joint state detecting unit 132 again.

The malfunction detecting unit 260 detects a malfunction occurring in the joint unit 130, based on various information for detecting a malfunction of the joint unit 130. Herein, since the functions of the malfunction detecting unit 260 are described in detail in the above <2. Functional configuration of robot arm control system>, detailed description will be reduced or omitted at this point. Information about the malfunction detected by the malfunction detecting unit 260 is provided to the operation condition setting unit 242 or stored in the storage unit 220, for example. Based on the information about the malfunction, the operation condition setting unit 242 determines an operation to be performed by the arm unit 120 (malfunction avoidance operation, partial function suspension operation, or function suspension operation) according to the type of malfunction, and sets an operation condition (for example, a purpose of motion, a constraint condition, and an internal model) corresponding to the determined operation. By having the virtual force calculating unit 243 and the actual force calculating unit 244 perform various computational processes based on the operation condition set in this way, a control value is computed so as to realize the selected malfunction avoidance operation, partial function suspension operation, or function suspension operation pivot operation.

The description of the other components of the control device 20 will now continue.

The input unit 210 is an input interface through which the user inputs, for example, information or a command related to driving control of the robot arm apparatus 10 to the control device 20. In the present embodiment, based on an operation input from the input unit 210 by the user, driving of the arm unit 120 of the robot arm apparatus 10 may be controlled, and the position and posture of the imaging unit 140 may be controlled. Specifically, as described above, as the user inputs instruction information related to an instruction of arm driving input from the input unit 210 to the operation condition setting unit 242, the operation condition setting unit 242 may set the purpose of motion in the whole body cooperative control based on the instruction information. As described above, the whole body cooperative control is performed using the purpose of motion based on the instruction information input by the user, and thus driving of the arm unit 120 according to the user's operation input is implemented.

Specifically, the input unit 210 includes an operation unit operated by the user such as a mouse, a keyboard, a touch panel, a button, a switch, a lever, and a pedal, for example. For example, when the input unit 210 includes a pedal, the user can control driving of the arm unit 120 by operating the pedal by foot. Thus, even when the user performs a treatment on the patient's medical procedure part using both hands, it is possible to adjust the position and posture of the imaging unit 140, that is, the photographing position or the photographing angle of the medical procedure part through an operation of the pedal by foot.

The storage unit 220 stores various kinds of pieces of information that are processed by the control device 20. In the present embodiment, the storage unit 220 can store various kinds of parameters used in the operation related to the whole body cooperative control and the ideal joint control performed by the control unit 230. For example, the storage unit 220 may store the purpose of motion, the constraint condition, and the internal model used in the operation related to the whole body cooperative control performed by the whole body cooperative control unit 240. The purpose of motion stored in the storage unit 220 may be a purpose of motion that can be set in advance so that the imaging unit 140 can stop at a certain point in the space as described above, for example. Further, the constraint condition may be set by the user in advance according to the geometric configuration of the arm unit 120, the purpose of the robot arm apparatus 10, or the like and then stored in the storage unit 220. Furthermore, the storage unit 220 may store various kinds of information related to the arm unit 120 used when the arm state acquiring unit 241 acquires the arm state. Moreover, the storage unit 220 may store, for example, the operation result in the operation related to the whole body cooperative control and the ideal joint control performed by the control unit 230 and numerical values calculated in the operation process. As described above, the storage unit 220 may store all parameters related to various kinds of processes performed by the control unit 230, and the control unit 230 can perform various kinds of processes while transmitting or receiving information to or from the storage unit 220.

The function and configuration of the control device 20 have been described above. The control device 20 according to the present embodiment may be configured, for example, with various kinds of information processing devices (arithmetic processing devices) such as a personal computer (PC) or a server. Next, a function and configuration of the display device 30 will be described.

The display device 30 displays various kinds of information on the display screen in various formats such as text or an image, and visually notifies the user of the information. In the present embodiment, the display device 30 displays an image captured by the imaging unit 140 of the robot arm apparatus 10 through the display screen. Specifically, the display device 30 includes a function or component such as an image signal processing unit (not illustrated) that performs various kinds of image processing on the image signal acquired by the imaging unit 140 or a display control unit (not illustrated) that performs control such that an image based on the processed image signal is displayed on the display screen. Further, the display device 30 may have various kinds of functions and components that are equipped in a general display device in addition to the above function or component. The display device 30 corresponds to the display device 550 illustrated in FIG. 11.

The functions and configurations of the robot arm apparatus 10, the control device 20, and the display device 30 according to the present embodiment have been described above with reference to FIG. 16. Each of the above components may be configured using a versatile member or circuit, and may be configured by hardware specialized for the function of each component. Further, all the functions of the components may be performed by a CPU or the like. Thus, a configuration to be used may be appropriately changed according to a technology level when the present embodiment is carried out.

As described above, according to the present embodiment, the arm unit 120 having the multi-link structure in the robot arm apparatus 10 has at least 6 or more degrees of freedom, and driving of each of the plurality of joint units 130 configuring the arm unit 120 is controlled by the drive control unit 111. Further, the medical apparatus is installed at the front edge of the arm unit 120. As driving of each joint unit 130 is controlled as described above, driving control of the arm unit 120 having a high degree of freedom is implemented, and the robot arm apparatus 10 for medical use having high operability for a user is implemented.

More specifically, according to the present embodiment, in the robot arm apparatus 10, the state of the joint unit 130 is detected by the joint state detecting unit 132. Further, in the control device 20, based on the state of the joint unit 130, the purpose of motion, and the constraint condition, various kinds of operations related to the whole body cooperative control using the generalized inverse dynamics for controlling driving of the arm unit 120 are performed, and torque command value τ serving as the operation result are calculated. Furthermore, in the robot arm apparatus 10, driving of the arm unit 120 is controlled based on the torque command value τ. As described above, in the present embodiment, driving of the arm unit 120 is controlled by the whole body cooperative control using the generalized inverse dynamics. Thus, driving control of the arm unit 120 according to the force control is implemented, and the robot arm apparatus having the high operability for the user is implemented. Further, in the present embodiment, in the whole body cooperative control, for example, control for implementing various kinds of purposes of motion for improving user convenience such as the pivot movement and the power assist movement can be performed. Furthermore, in the present embodiment, for example, various driving units for moving the arm unit 120 manually or through an operation input from a pedal are implemented, and thus user convenience is further improved.

Further, in the present embodiment, the whole body cooperative control and the ideal joint control are applied to driving control of the arm unit 120. In the ideal joint control, a disturbance component such as friction or inertia in the joint unit 130 is estimated, and feedforward control is performed using the estimated disturbance component. Thus, even when there is a disturbance component such as friction, the ideal response can be implemented on driving of the joint unit 130. Thus, small influence of vibration or the like, high-accuracy responsiveness, and high positioning accuracy or stability are implemented in driving control of the arm unit 120.

Further, in the present embodiment, each of the plurality of joint units 130 configuring the arm unit 120 has a configuration suitable for the ideal joint control illustrated in FIG. 13, for example, and the rotational angle, the generated torque and the viscous drag coefficient of each of the joint units 130 can be controlled according to an electric current value. As described above, driving of each of the joint units 130 is controlled according to an electric current value, and driving of each of the joint units 130 is controlled according to the whole body cooperative control while detecting the entire state of the arm unit 120, and thus the counter balance is unnecessary, and the small robot arm apparatus 10 is implemented.

(6-2-5. Specific Example of Purpose of Motion)

Next, a specific example of the purpose of motion according to the present embodiment will be described. As described above in (6-2-4. Configuration of the robot arm control system), in the present embodiment, various kinds of purposes of motion are implemented by the whole body cooperative control. Here, as a specific example of the purpose of motion according to the present embodiment, the power assist movement and the pivot movement will be described. In the following description of the specific example of the purpose of motion, components of the robot arm control system according to the present embodiment are indicated using reference numerals in the functional block diagram illustrated in FIG. 16.

The power assist movement is a movement of controlling the state of the joint unit 130 such that gravity acting on the arm unit 120 is negated and controlling the state of the joint unit 130 such that movement of the arm unit 120 in a direction of force applied from the outside is supported. Specifically, when the user manually moves the arm unit 120, the power assist movement is a movement of controlling driving of the arm unit 120 such that force applied by the user is supported. More specifically, in order to implement the power assist movement, first, external torque is detected by the torque detecting unit 134 in a state in which no force other than gravity acts on the arm unit 120, and the instantaneous purpose of motion is set so that the generated torque for negating the detected external torque is generated by each of the joint units 130. At this stage, the position and posture of the arm unit 120 are held in a certain state. When external torque is further applied from the outside (for example, from the user) in this state, additionally applied external torque is detected by the torque detecting unit 134, and the instantaneous purpose of motion is further set such that each of the joint units 130 generates generated torque in the same direction as the detected additional external torque. As driving of each of the joint units 130 is controlled according to the instantaneous purpose of motion, the power assist movement is implemented. Through the power assist movement, the user can move the arm unit by small force, and thus the user can have a feeling of moving the arm unit 120 in a non-gravity state, and the operability of the arm unit 120 by the user is improved.

The pivot movement is a turning movement in which the front edge unit installed at the front edge of the arm unit 120 moves on a plane of a cone having a certain point in the space as an apex in a state in which a direction of the front edge unit is fixed on the certain point, and an axis of the cone is used as a pivot axis. Specifically, when the front edge unit is the imaging unit 140, the pivot movement is a turning movement in which the imaging unit 140 installed at the front edge of the arm unit 120 moves on a plane of a cone having a certain point in a space as an apex in a state in which the photographing direction of the imaging unit 140 is fixed on the certain point, and an axis of the cone is used as a pivot axis. As a point corresponding to the apex of the cone in the pivot movement, for example, the medical procedure part is selected. Further, in the pivot movement, the turning movement may be performed in a state in which a distance between the front edge unit or the imaging unit 140 and the point corresponding to the apex of the cone is maintained constant. Further, since the direction of the front edge unit or the photographing direction of the imaging unit 140 is fixed on a certain point (for example, the medical procedure part) in the space, the pivot movement is also referred to as a "point lock movement."

Figure 17:
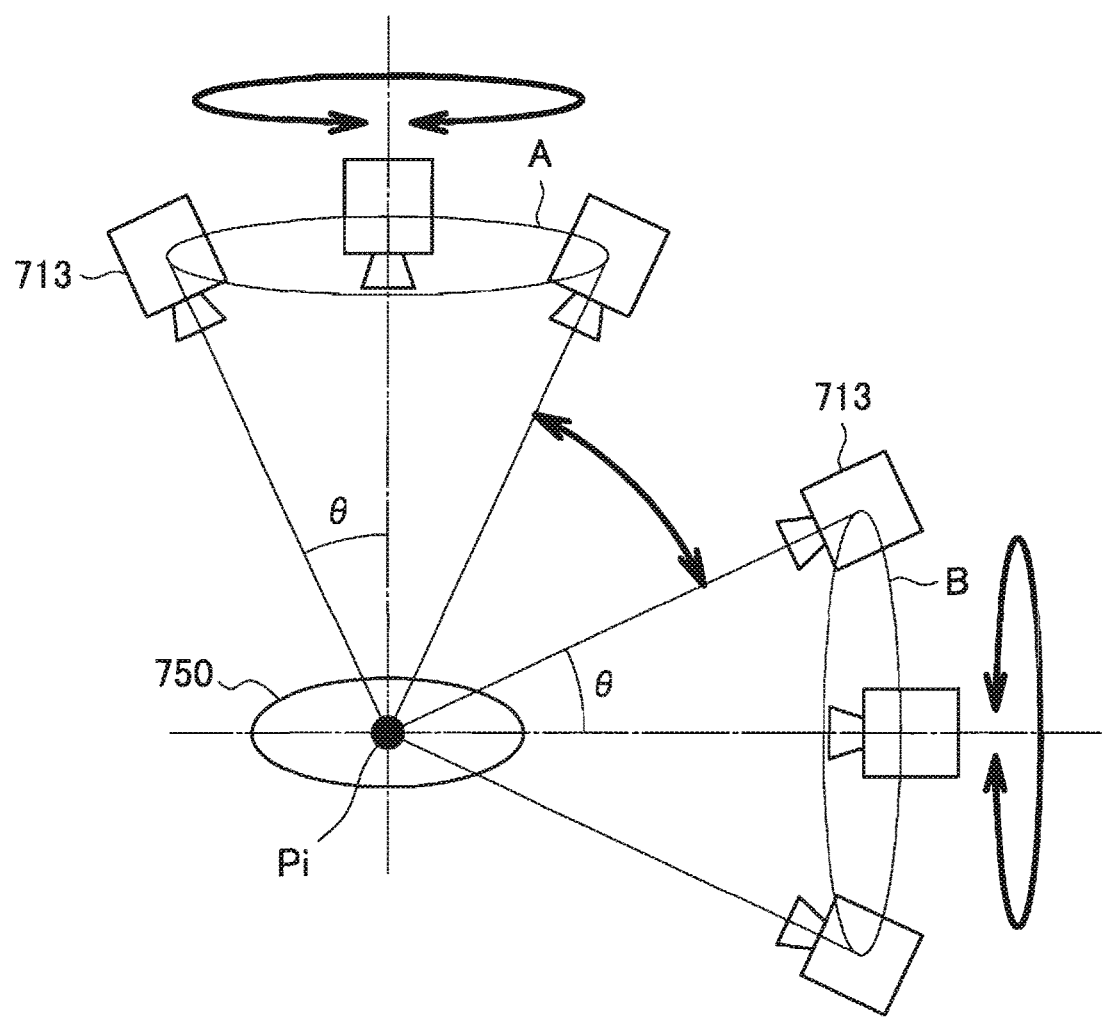
FIG. 17 is an explanatory diagram for describing a pivot movement that is a specific example of an arm movement according to an embodiment of the present disclosure.
Figure 18:
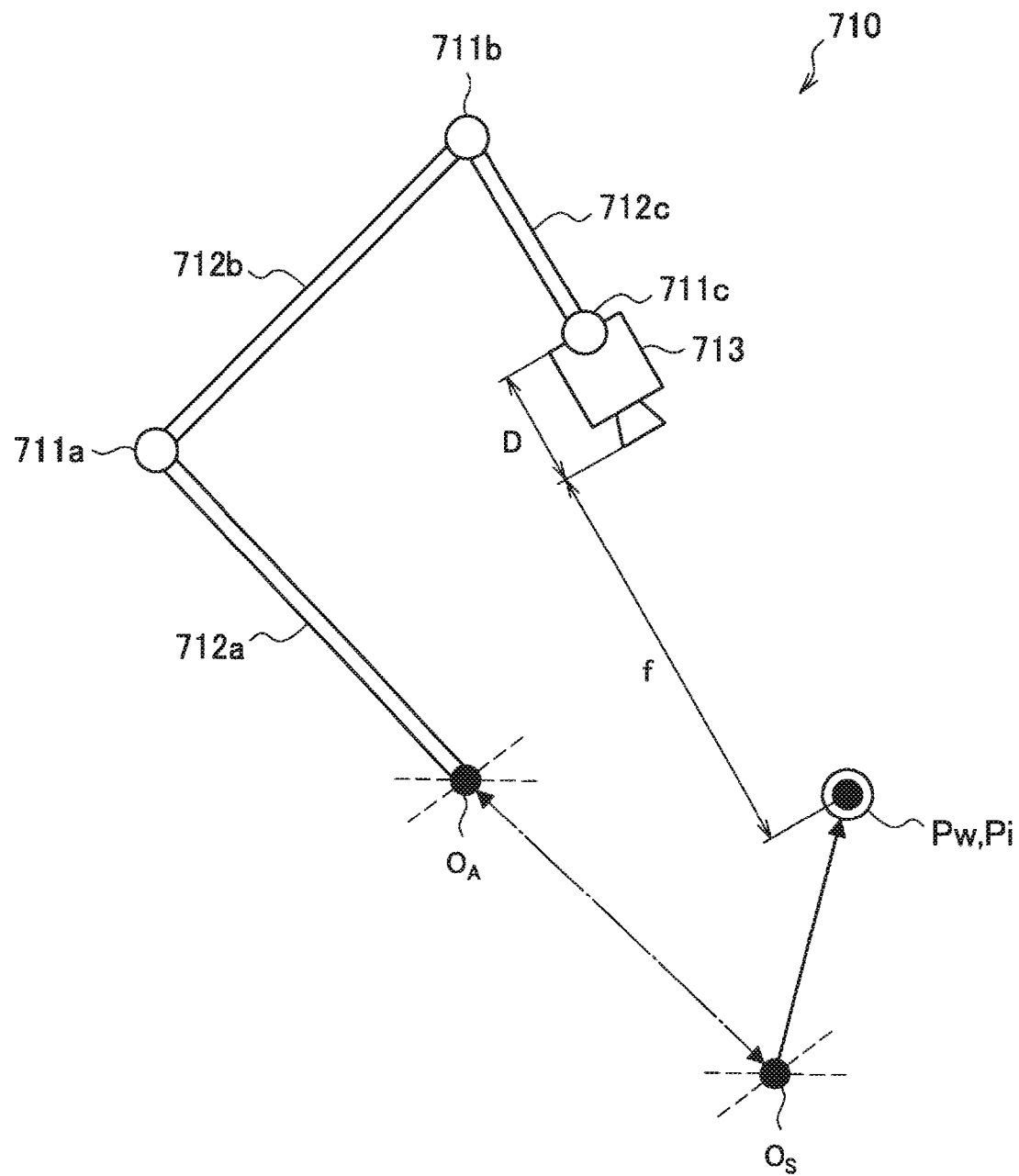
FIG. 18 is an explanatory diagram for describing a purpose of motion and a constraint condition for implementing the pivot movement illustrated in FIG. 17.

The pivot movement will be described in further detail with reference to FIGS. 17 and 18. FIG. 17 is an explanatory diagram for describing the pivot movement that is a specific example of the arm movement according to an embodiment of the present disclosure. FIG. 18 is an explanatory diagram for describing the purpose of motion and the constraint condition for implementing the pivot movement illustrated in FIG. 17.

Referring to FIG. 17, a medical procedure part on a patient 750 is set as an apex in the pivot movement. The apex is referred to as a "pivot point $P_i$." In FIG. 17, for the sake of convenience, in the robot arm apparatus 10 according to the present embodiment, an imaging unit 713 serving as a unit corresponding to the imaging unit 140 of FIG. 16 is illustrated. As illustrated in FIG. 17, in the pivot movement, the purpose of motion and the constraint condition may be set so that the imaging unit 713 can move on a circumference of a bottom of a cone A, that is, the imaging unit 713 moves within a plane of the cone A in a state in which a distance between the imaging unit 713 and the pivot point $P_i$ is maintained constant. Further, the shape of the cone A, that is, an angle θ of an apex of the cone A or a distance between the pivot point $P_i$ and the imaging unit 713, may be appropriately set by the user. For example, the distance between the pivot point $P_i$ and the imaging unit 713 is adjusted to a focal distance of an optical system in the imaging unit 713. As the pivot movement is applied, the medical procedure part can be observed at an equal distance at different angles, and thus convenience for the user who performs surgery can be improved.

Further, in the pivot movement, it is possible to move the position of the cone in which the imaging unit 713 is movable in a state in which the pivot point $P_i$ is fixed as in the cones A and B. In the example illustrated in FIG. 17, the pivot axis of the cone A is substantially perpendicular to the medical procedure part, and the pivot axis of the cone B is substantially parallel to the medical procedure part. As described above, for example, the purpose of motion and the constraint condition may be set so that the cone for performing the pivot movement can be rotated by about 90° in a state in which the pivot point $P_i$ is fixed such as the cones A and B. As the pivot movement is applied, it is possible to observe the medical procedure part from more directions, and thus the convenience for the user can be further improved.

The example illustrated in FIG. 17 illustrates an example in which the purpose of motion and the constraint condition are set so that the imaging unit 713 can move on the circumference of the bottom of the cone A, but the pivot movement according to the present embodiment is not limited to this example. For example, the purpose of motion and the constraint condition may be set so that the distance between the pivot point $P_i$ and the imaging unit 713 can be freely changed in a state in which the position of the pivot point $P_i$ and the angles θ of the apexes of the cones A and B are fixed. As the pivot movement is applied, it is possible to change the distance between the imaging unit 713 and the medical procedure part in a state in which the angle is fixed, and thus it is possible to observe the medical procedure part according to the user's desire, for example, to enlarge or reduce the medical procedure part and then observe the enlarged or reduced medical procedure part by appropriately adjusting the focal distance (focus) of the imaging unit 713.

Next, the purpose of motion and the constraint condition for implementing the pivot movement illustrated in FIG. 17 will be described in detail with reference to FIG. 18. Referring to FIG. 18, an example in which an arm unit 710 including the imaging unit 713 performs the pivot movement using the pivot point $P_i$ as a base point. In FIG. 18, the pivot movement in which the distance between the imaging unit 713 and the pivot point $P_i$ is maintained constant will be described as an example. The arm unit 710 includes a plurality of joint units 711a, 711b, and 711c and a plurality of links 712a, 712b, and 712c, and driving of the arm unit 710 is controlled according to the whole body cooperative control and the ideal joint control according to the present embodiment. For example, the arm unit 710 and the components thereof have the same configurations as the arm unit 420 and the components according to the present embodiment illustrated in FIG. 12.

Here, an arm coordinate system in which an origin $O_A$ serving as a supporting point of the arm unit 710 is used as a zero point and a space coordinate system in which an origin $O_S$ in a space is used as a zero point are considered. The motion of the arm unit 710 is managed by the arm coordinate system. Further, the arm coordinate system and the space coordinate system are defined such that they can be converted into each other.

An imaging center viewed from the space coordinate system is indicated by $P_w$. Further, in the arm coordinate system, a position away from the joint unit 711c connecting the imaging unit 713 with the link 712c by a length D of the imaging unit 713 and a focal distance f of the imaging unit 713 is referred to as a pivot point $P_i$.

In this state, the purpose of motion and the constraint condition are set so that the arm unit 710 is driven in a state in which the pivot point $P_i$ matches the imaging center $P_w$. In other words, the constraint of fixing the pivot point $P_i$ in the arm coordinate system is fixed to the imaging center $P_w$ in the space coordinate system is set in the arm coordinate system. Further, coordinates at which the imaging unit 713 is positioned on the plane of the cone having the pivot point $P_i$ (that is, the imaging center $P_w$) as an apex or the position of the imaging unit 713 at which the imaging unit 713 faces the pivot point $P_i$ is set as the purpose of motion. As the whole body cooperative control is performed under the constraint condition and the purpose of motion, even when the position and posture of the imaging unit 713 are changed by the movement of the arm unit 710, the direction of the imaging unit 713 consistently faces the imaging center $P_w$ (that is, the pivot point $P_i$), and the distance between the imaging unit 713 and the imaging center $P_w$ is maintained to have the focal distance f. Thus, the pivot movement in the state in which the distance between the imaging unit 713 and the imaging center $P_w$ is maintained constant is implemented. When the pivot movement is performed while changing the distance between the imaging unit 713 and the imaging center $P_w$ (or the pivot point $P_i$), it is desirable to change the setting method of the pivot point $P_i$. Specifically, for example, in the arm coordinate system, it is desirable to set the position away from the joint unit 711c by the length D of the imaging unit 713 and an arbitrary distance as the pivot point $P_i$ and use the arbitrary distance a variable parameter.

Further, a combination of the pivot movement and the power assist movement may be used. When a combination of the pivot movement and the power assist movement is used, for example, when the user manually moves the imaging unit 140, the user can move the imaging unit 140 with small power due to a feeling of moving the imaging unit 140 in the non-gravity state, and the moving position of the imaging unit 140 is limited to within the plane of the cone. Thus, the movement operability of the imaging unit 140 is improved at the time of the pivot movement.

The power assist movement and the pivot movement have been described above as the specific example of the purpose of motion according to the present embodiment. The purpose of motion according to the present embodiment is not limited to this example. In the present embodiment, for example, the following purpose of motion can also be implemented.

For example, coordinates of the imaging unit 140 may be set as the purpose of motion so that the position of the imaging unit 140 is fixed at a certain position. In this case, for example, when force is applied from the outside to the components other than the imaging unit 140 of the arm unit 120, it is possible to set the purpose of motion and the constraint condition so that the joint unit 130 and the link are also fixed at a certain position and not moved, and it is possible to set the purpose of motion and the constraint condition so that the joint unit 130 and the link are moved according to the applied external force, but the position of the imaging unit 140 is fixed. In the latter case, for example, when the arm unit 120 interferes with a task and is desired to be moved, control of a high degree of freedom of moving the positions and postures of the other components of the arm unit 120 in the state in which an image captured by the imaging unit 140 is fixed is implemented.

Further, the purpose of motion and the constraint condition may be set so that a movement of stopping driving of the arm unit 120 immediately is implemented, for example, when the arm unit 120 detects contact with a person or a thing while being driven. By performing such a movement, it is possible to reduce a risk of the arm unit 120 colliding with a person or object. Further, when the arm unit 120 comes into contact with a person or object, for example, the joint state detecting unit 132 may detect the contact according to a change in the external torque applied to the joint unit 130.

Further, for example, the purpose of motion may be set so that the imaging unit 140 moves along a certain trajectory in the space. Specifically, coordinates of points indicating the certain trajectory may be set as the purpose of motion. By setting the purpose of motion as described above, the movable range of the imaging unit 140 is limited to the trajectory. Further, by setting the speed of the imaging unit 140, times at which the imaging unit 140 passes through the points, or the like as the purpose of motion together with the coordinates of the points indicating the trajectory, automated driving by which the imaging unit 140 automatically moves along a certain trajectory at a certain timing can also be performed. The driving control according to such a motion setting is effective, for example, when the robot arm apparatus 10 repeatedly performs a certain task automatically.

Further, for example, the purpose of motion and the constraint condition may be set so that a movement of preventing the arm unit 120 from invading a certain region in the space is implemented. As described above with reference to FIG. 11, in the present embodiment, the user performs surgery while viewing the display screen. Thus, if the arm unit 120 is positioned in a region between the user and the display screen, the user's field of vision is blocked, and thus the surgery efficiency is likely to be lowered. Thus, for example, by setting the region between the user and the display screen as an invasion prohibition region of the arm unit 120, the surgery efficiency can be improved.

Here, when the invasion prohibition region is set to the arm unit 120 as described above, it is preferable that the degrees of freedom of the arm unit 120 be more than the 6 degrees of freedom. This is because degrees of freedom after the 6 degrees of freedom can be used as redundant degrees of freedom, and thus it is possible to secure driving of the 6 degrees of freedom while dealing with the invasion prohibition region or the like. A configuration of a robot arm apparatus including an arm unit having more degrees of freedom than the 6 degrees of freedom will be described in detail with reference to FIG. 19.

Figure 19:
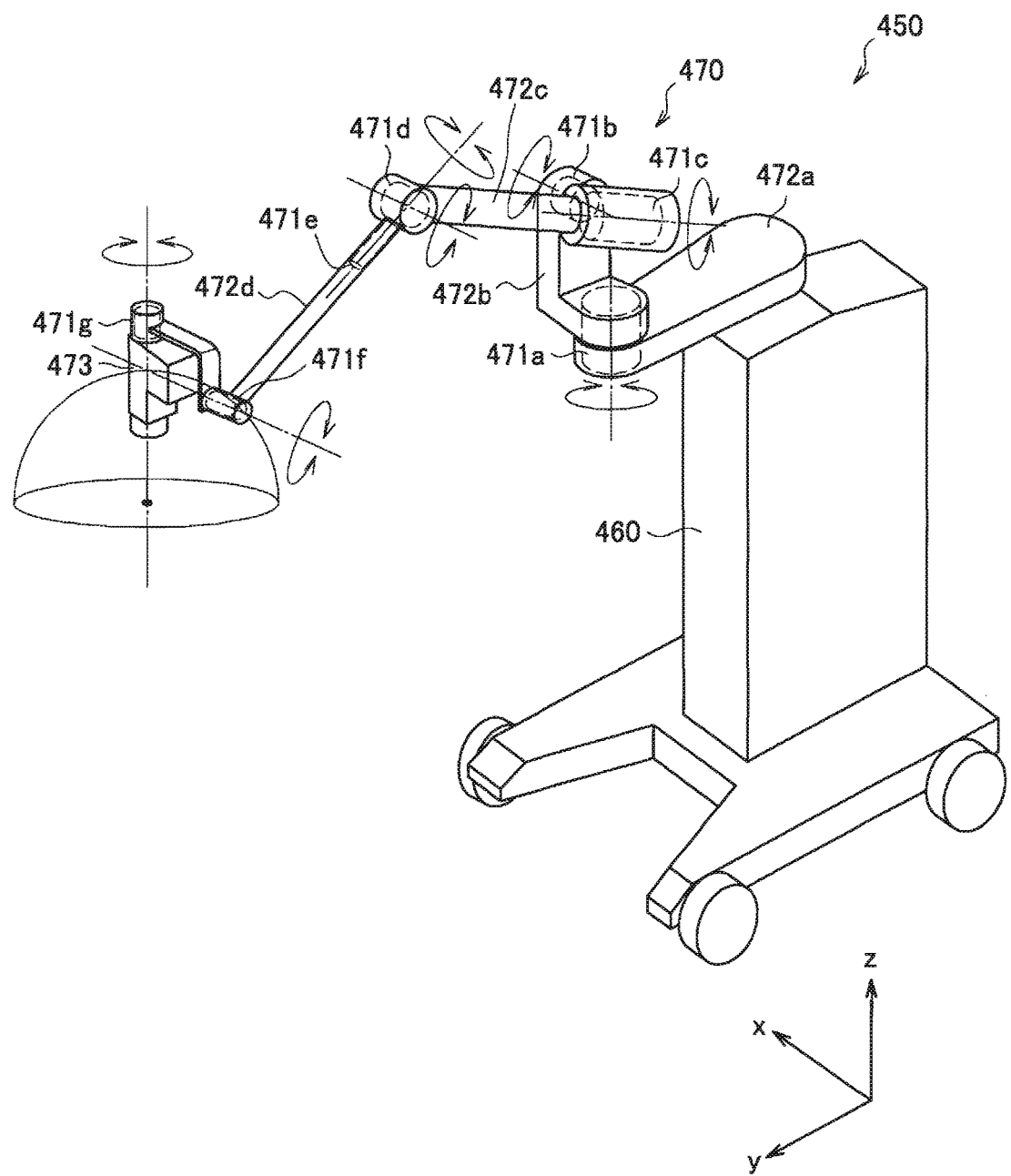
FIG. 19 is a schematic diagram illustrating an external appearance of a modified example having a redundant degree of freedom in a robot arm apparatus according to an embodiment of the present disclosure.

FIG. 19 is a schematic diagram illustrating an external appearance of a modified example having a redundant degree of freedom in a robot arm apparatus according to an embodiment of the present disclosure. The same coordinate axes as the directions defined in FIG. 12 are illustrated in FIG. 19.

Referring to FIG. 19, a robot arm apparatus 450 according to the present modified example includes a base unit 460 and an arm unit 470. Further, the arm unit 470 includes a plurality of joint units 471a to 471g, a plurality of links 472a to 472d connecting the joint units 471a to 471g with one another, and an imaging unit 473 installed at the front edge of the arm unit 470. Here, the robot arm apparatus 450 illustrated in FIG. 19 corresponds to a configuration in which the degrees of freedom of the arm unit 470 are increased by one compared to the robot arm apparatus 400 described above with reference to FIG. 12. Thus, the functions and configurations of the base unit 460, each of the joint units 471a to 471g and the links 472a to 472d, and the imaging unit 473 are similar to the functions and configurations of the base unit 410, each of the joint units 421a to 421f and the links 422a to 422c, and the imaging unit 423 of the robot arm apparatus 400 described above with reference to FIG. 12, and thus a detailed description thereof is omitted. The following description will proceed focusing on a configuration of the arm unit 470 serving as a difference with the robot arm apparatus 400.

The robot arm apparatus 450 according to the present embodiment includes the 7 joint units 471a to 471g, and 7 degrees of freedom are implemented with regard to driving of the arm unit 470. Specifically, one end of the link 472a is connected with the base unit 460, and the other end of the link 472a is connected with one end of the link 472b through the joint unit 421a. Further, the other end of the link 422b is connected with one end of the link 472c through the joint units 471b and 471c. Furthermore, the other end of the link 472c is connected with one end of the link 472d through the joint units 471d and 471e, and the other end of 472d is connected with the imaging unit 473 through the joint units 471f and 471g. As described above, the arm unit 470 extending from the base unit 460 is configured such that the base unit 460 serves as a support point, and the ends of the plurality of links 472a to 472d are connected with one another through the joint units 471a to 471g.

Further, as illustrated in FIG. 19, the joint units 471a, 471c, 471e, and 471g are installed such that the long axis direction of the links 472b to 472d connected thereto and the photographing direction of the imaging unit 473 connected thereto are set as the rotary axis direction, and the joint units 471b, 471d, and 471f are installed such that the x axis direction serving as a direction in which connection angles of the links 472c and 472d and the imaging unit 473 connected thereto are changed within the y-z plane is set as the rotary axis direction. As described above, in the present modified example, the joint units 471a, 471c, 471e, and 471g have a function of performing yawing, and the joint units 471b, 471d, and 471f have a function of performing pitching.

As the arm unit 470 has the above configuration, in the robot arm apparatus 450 according to the present embodiment, the 7 degrees of freedom are implemented with regard to driving of the arm unit 470, and thus it is possible to freely move the imaging unit 473 within the space in the movable range of the arm unit 470, and the redundant degree of freedom is provided. In FIG. 19, similarly to FIG. 12, a hemisphere is illustrated as an example of the movable range of the imaging unit 473. When the central point of the hemisphere is the photographing center of the medical procedure part photographed by the imaging unit 473, the medical procedure part can be photographed at various angles by moving the imaging unit 473 on the spherical surface of the hemisphere in a state in which the photographing center of the imaging unit 473 is fixed to the central point of the hemisphere. Since the robot arm apparatus 450 according to the present embodiment has one redundant degree of freedom, it is possible to limit the movement of the imaging unit 473 to the hemisphere and the trajectory of the arm unit 470, and it is also possible to easily deal with the constraint condition such as the invasion prohibition region. By setting the invasion prohibition region, for example, it is possible to control driving of the arm unit 470 so that the arm unit 470 is not positioned between the monitor on which the image captured by the imaging unit 473 is displayed and the practitioner or the staff, and it is possible to prevent the monitor from being blocked from the view of the practitioner and the staff. Further, as the invasion prohibition region is set, it is possible to control driving of the arm unit 470 so that the arm unit 470 moves while avoiding interference (contact) with the practitioner and the staff or any other device therearound.

(6-3. Processing Procedure of Robot Arm Control Method)

Figure 20:
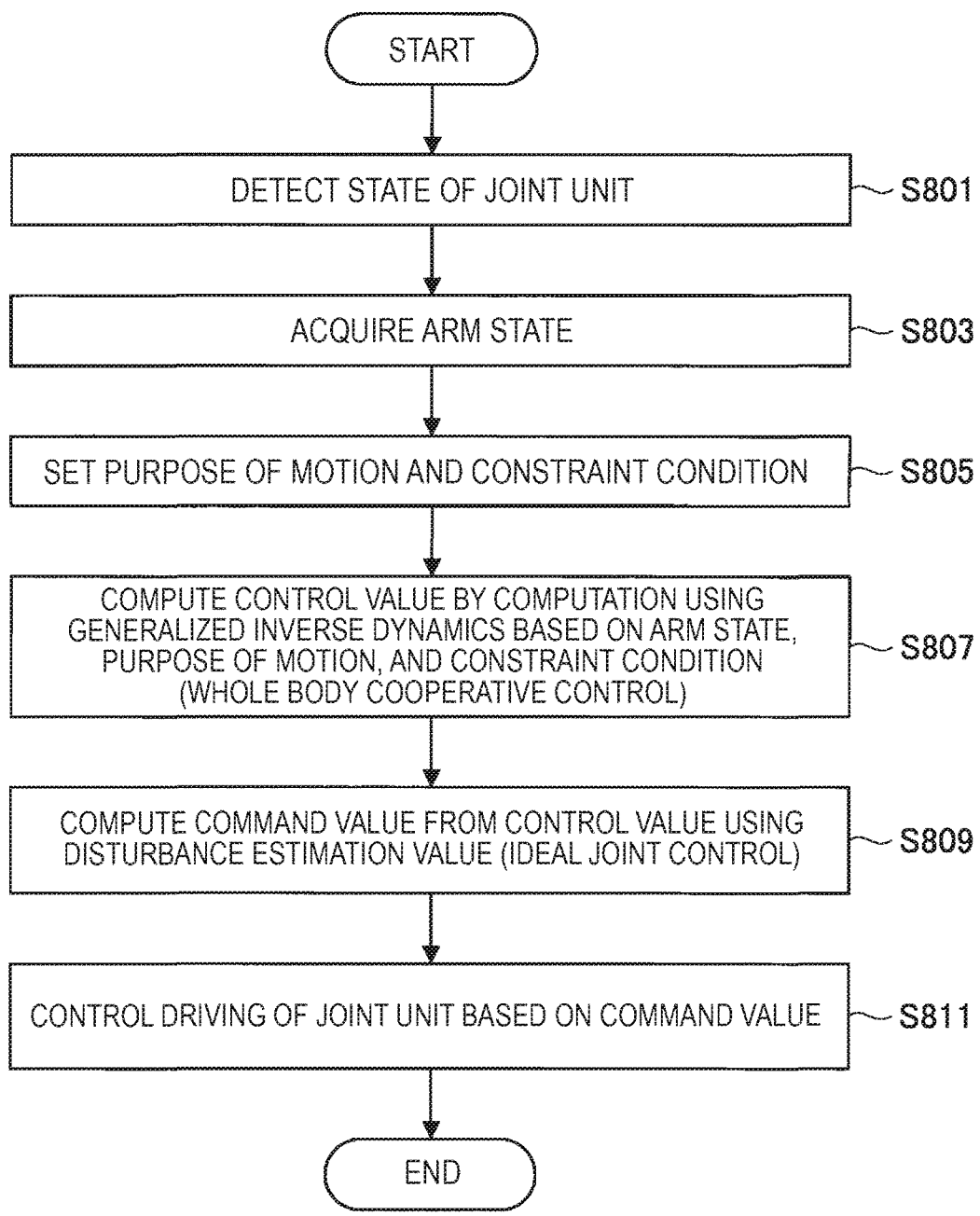
FIG. 20 is a flowchart illustrating a processing procedure of a robot arm control method according to an embodiment of the present disclosure.

Next, a processing procedure of a robot arm control method according to an embodiment of the present disclosure will be described with reference to FIG. 20. FIG. 20 is a flowchart illustrating a processing procedure of a robot arm control method according to an embodiment of the present disclosure. The following description will proceed with an example in which the robot arm control method according to the present embodiment is implemented through the configuration of the robot arm control system 1 illustrated in FIG. 16. Thus, the robot arm control method according to the present embodiment may be a medical robot arm control method. Further, in the following description of the processing procedure of the robot arm control method according to the present embodiment, the functions of the respective components of the robot arm control system 1 illustrated in FIG. 16 have already been described above in (6-2-4. Configuration of the robot arm control system), and thus a detailed description thereof is omitted.

Referring to FIG. 20, in the robot arm control method according to the present embodiment, first, in step S801, the joint state detecting unit 132 detects the state of the joint unit 130. Here, the state of the joint unit 130 refers to, for example, the rotational angle, the generated torque and/or the external torque in the joint unit 130.

Then, in step S803, the arm state acquiring unit 241 acquires the arm state based on the state of the joint unit 130 detected in step S801. The arm state refers to a motion state of the arm unit 120, and may be, for example, a position, a speed, or acceleration of each component of the arm unit 120, or force acting on each component of the arm unit 120.

Then, in step S805, the operation condition setting unit 242 sets the purpose of motion and the constraint condition used for the operation in the whole body cooperative control based on the arm state acquired in step S803. Further, the operation condition setting unit 242 may not set the purpose of motion based on the arm state, may set the purpose of motion based on the instruction information on driving of the arm unit 120 which is input, for example, from the input unit 210 by the user, and may use the purpose of motion previously stored in the storage unit 220. Furthermore, the purpose of motion may be set by appropriately combining the above methods. Moreover, the operation condition setting unit 242 may use the constraint condition previously stored in the storage unit 220.

Then, in step S807, the operation for the whole body cooperative control using the generalized inverse dynamics is performed based on the arm state, the purpose of motion, and the constraint condition, and a control value $\tau_a$ is calculated. The process performed in step S807 may be a series of processes in the virtual force calculating unit 243 and the actual force calculating unit 244 illustrated in FIG. 16, that is, a series of processes described above in (6-2-2. Generalized inverse dynamics).

Then, in step S809, the disturbance estimation value $\tau_d$ is calculated, the operation for the ideal joint control is performed using the disturbance estimation value $\tau_d$, and the command value $\tau$ is calculated based on the control value $\tau_a$. The process performed in step S809 may be a series of processes in the ideal joint control unit 250 illustrated in FIG. 16, that is, a series of processes described above in (6-2-3. Ideal joint control).

Lastly, in step S811, the drive control unit 111 controls driving of the joint unit 130 based on the command value $\tau$.

The processing procedure of the robot arm control method according to the present embodiment has been described above with reference to FIG. 20. In the present embodiment, the process of step S801 to step S811 illustrated in FIG. 20 is repeatedly performed while the task using the arm unit 120 is being performed. Thus, in the present embodiment, driving control of the arm unit 120 is continuously performed while the task using the arm unit 120 is being performed.

(6-4. Summary of Robot Arm Apparatus According to Whole Body Cooperative)

As described above, in the present embodiment, the following effects can be obtained.

As described above, according to the present embodiment, the arm unit 120 having the multi-link structure in the robot arm apparatus 10 has at least 6 or more degrees of freedom, and driving of each of the plurality of joint units 130 configuring the arm unit 120 is controlled by the drive control unit 111. Further, the medical apparatus is installed at the front edge of the arm unit 120. As driving of each joint unit 130 is controlled as described above, driving control of the arm unit 120 having a high degree of freedom is implemented, and the robot arm apparatus 10 for medical use having high operability for a user is implemented.

More specifically, according to the present embodiment, in the robot arm apparatus 10, the state of the joint unit 130 is detected by the joint state detecting unit 132. Further, in the control device 20, based on the state of the joint unit 130, the purpose of motion, and the constraint condition, various kinds of operations related to the whole body cooperative control using the generalized inverse dynamics for controlling driving of the arm unit 120 are performed, and torque command value τ serving as the operation result are calculated. Furthermore, in the robot arm apparatus 10, driving of the arm unit 120 is controlled based on the torque command value τ. As described above, in the present embodiment, driving of the arm unit 120 is controlled by the whole body cooperative control using the generalized inverse dynamics. Thus, driving control of the arm unit 120 according to the force control is implemented, and the robot arm apparatus having the high operability for the user is implemented. Further, in the present embodiment, in the whole body cooperative control, for example, control for implementing various kinds of purposes of motion for improving user convenience such as the pivot movement and the power assist movement can be performed. Furthermore, in the present embodiment, for example, various driving units for moving the arm unit 120 manually or through an operation input from a pedal are implemented, and thus user convenience is further improved.

Further, in the present embodiment, the whole body cooperative control and the ideal joint control are applied to driving control of the arm unit 120. In the ideal joint control, a disturbance component such as friction or inertia in the joint unit 130 is estimated, and feedforward control is performed using the estimated disturbance component. Thus, even when there is a disturbance component such as friction, the ideal response can be implemented on driving of the joint unit 130. Thus, small influence of vibration or the like, high-accuracy responsiveness, and high positioning accuracy or stability are implemented in driving control of the arm unit 120.

Further, in the present embodiment, each of the plurality of joint units 130 configuring the arm unit 120 has a configuration suitable for the ideal joint control illustrated in FIG. 13, for example, and the rotational angle, the generated torque and the viscous drag coefficient of each of the joint units 130 can be controlled according to an electric current value. As described above, driving of each of the joint units 130 is controlled according to an electric current value, and driving of each of the joint units 130 is controlled according to the whole body cooperative control while detecting the entire state of the arm unit 120, and thus the counter balance is unnecessary, and the small robot arm apparatus 10 is implemented.

As described above, according to the present embodiment, it is possible to fulfill all capabilities necessary for the robot arm apparatus described above in (6-1. Review of medical robot arm apparatus). Thus, it is possible to perform various kinds of medical procedures more efficiently using the robot arm apparatus according to the present embodiment and further reduce the fatigue or the burden of the user or the patient.

Further, in the present embodiment, as the arm unit 120 of the robot arm apparatus 10 is driven by the force control, even when the arm unit 120 interferes with or comes into contact with the practitioner, the staff, or the like during driving, the arm unit 120 does not generate larger force than necessary, and the arm unit 120 safely stops. Furthermore, when the interference is resolved, the arm unit 120 is moved up to a desired position according to the set purpose of motion, and the medical procedure is continued. As described above, in the present embodiment, as the force control is used for driving control of the robot arm apparatus 10, higher safety is secured even when the arm unit 120 interferes with something nearby while being driven.

For example, the above embodiment has shown an example in which a front edge unit of an arm unit of a robot arm apparatus is an imaging unit, and a medical procedure part is photographed by the imaging unit during surgery as illustrated in FIG. 11, but the present embodiment is not limited to this example. The robot arm control system 1 according to the present embodiment can be applied even when a robot arm apparatus including a different front edge unit is used for another purpose. For example, the front edge unit may be an endoscope or a laparoscope, and may be any other examination device such as an ultrasonic examination apparatus or a gastrocamera.

For example, for a medical procedure using a gastrocamera, the gastrocamera is inserted into the patient's body, and various procedures are performed using separately inserted surgical tools, such as forceps and an electrosurgical instrument, while observing a picture captured by the gastrocamera. With such a medical procedure method, if the practitioner were able to operate the tools for the procedure directly while operating the gastrocamera with the robot arm, for example, it would be possible for a single person to perform the medical procedure, enabling more efficient medical procedures. However, with typical existing balance arms, from the perspective of operability, it is difficult for a single person to operate the surgical tools by hand and operate the gastrocamera with the robot arm simultaneously. Thus, existing methods require multiple staff members, and it is typical to have one practitioner operate the gastrocamera with the robot arm while another practitioner performs the procedure using surgical tools. However, with a robot arm apparatus according to the present embodiment, high operability by whole body cooperative control is realized, as discussed above. In addition, by ideal joint control, high-precision response and high stability with fewer effects such as vibration are realized. Consequently, according to the present embodiment, it becomes possible for a single practitioner to easily operate a gastrocamera for observation with the robot arm apparatus and also operate surgical tools by hand.

Further, the robot arm apparatus according to the present embodiment may be used for purposes other than medical uses. In the robot arm apparatus according to the present embodiment, since the high-accuracy responsiveness and the high stability are implemented through the ideal joint control, for example, it is also possible to deal with a task such as processing or assembly of industrial components that has to be performed with a high degree of accuracy.

Further, the above embodiment has been described in connection with the example in which the joint unit of the robot arm apparatus includes a rotation mechanism, and rotary driving of the rotation mechanism is controlled such that driving of the arm unit is controlled, but the present embodiment is not limited to this example. For example, in the robot arm apparatus according to the present embodiment, the link configuring the arm unit may have a mechanism that expands or contracts in an extension direction of the link (such as a hydraulic driving mechanism or a mechanism that drives a ball screw, for example), and the length of the link may be variable. When the length of the link is variable, for example, driving of the arm unit is controlled such that a desired purpose of motion is achieved by the whole body cooperative control in which expansion and contraction of the link is considered in addition to rotation in the joint unit.

Further, the above embodiment has been described in connection with the example in which the degrees of freedom of the arm unit in the robot arm apparatus are the 6 or more degrees of freedom, but the present embodiment is not limited to this example. Further, the description has proceeded with the example in which each of the plurality of joint units configuring the arm unit includes the actuator that supports the ideal joint control, but the present embodiment is not limited to this example. In the present embodiment, various purposes of motion can be set according to the purpose of the robot arm apparatus. Thus, as long as the set purpose of motion can be achieved, the arm unit may have fewer than 6 degrees of freedom, and some of the plurality of joint units configuring the arm unit may be joint units having a general joint mechanism. As described above, in the present embodiment, the arm unit may be configured to be able to achieve the purpose of motion or may be appropriately configured according to the purpose of the robot arm apparatus.

<7. Hardware Configuration>

Figure 21:
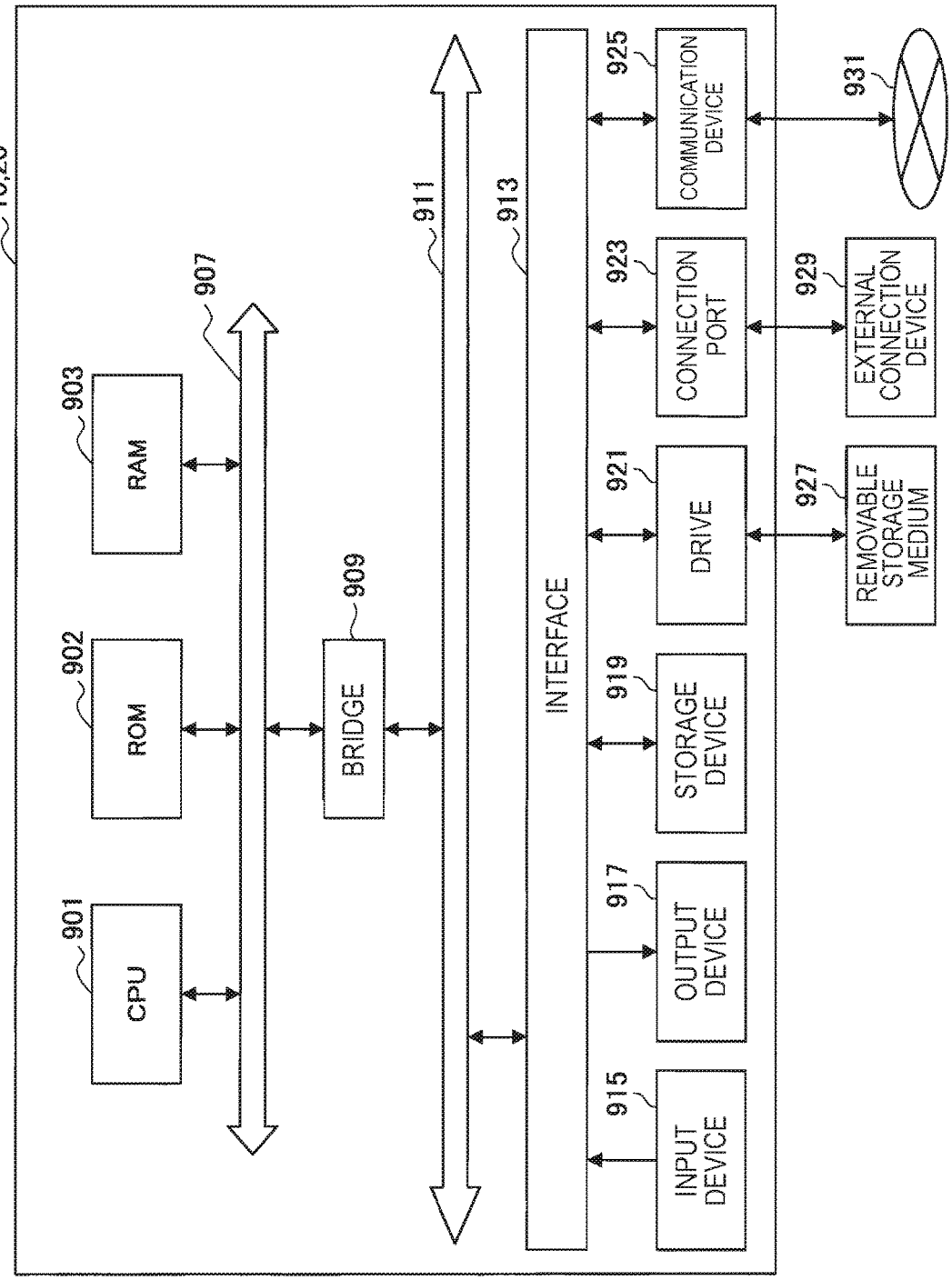
FIG. 21 is a functional block diagram illustrating an exemplary configuration of a hardware configuration of a robot arm apparatus and a control device according to an embodiment of the present disclosure.

Next, a hardware configuration of the robot arm apparatus 10 and the control device 20 according to the present embodiment illustrated in FIGS. 1 and 16 will be described in detail with reference to FIG. 21. FIG. 21 is a functional block diagram illustrating an exemplary configuration of a hardware configuration of the robot arm apparatus 10 and the control device 20 according to an embodiment of the present disclosure.

The robot arm apparatus 10 and the control device 20 mainly include a CPU 901, a ROM 903, and a RAM 905. The robot arm apparatus 10 and the control device 20 further include a host bus 907, a bridge 909, an external bus 911, an interface 913, an input device 915, an output device 917, a storage device 919, a drive 921, a connection port 923, and a communication device 925.

The CPU 901 functions as an arithmetic processing device and a control device, and controls all or some operations of the robot arm apparatus 10 and the control device 20 according to various kinds of programs recorded in the ROM 903, the RAM 905, the storage device 919, or a removable storage medium 927. The ROM 903 stores a program, an operation parameter, or the like used by the CPU 901. The RAM 905 primarily stores a program used by the CPU 901, a parameter that appropriately changes in execution of a program, or the like. The above-mentioned components are connected with one another by the host bus 907 configured with an internal bus such as a CPU bus. The CPU 901 corresponds to, for example, the joint control unit 135, the arm control unit 110 and the control unit 230 illustrated in FIG. 16 in the present embodiment.

The host bus 907 is connected to the external bus 911 such as a peripheral component interconnect/interface (PCI) bus through the bridge 909. Further, the input device 915, the output device 917, the storage device 919, the drive 921, the connection port 923, and the communication device 925 are connected to the external bus 911 via the interface 913.

The input device 915 is an operating unit used by the user such as a mouse, a keyboard, a touch panel, a button, a switch, a lever, or a pedal. For example, the input device 915 may be a remote control unit (a so-called remote controller) using infrared light or any other radio waves, and may be an external connection device 929 such as a mobile telephone or a PDA corresponding to an operation of the robot arm apparatus 10 and the control device 20. Further, for example, the input device 915 is configured with an input control circuit that generates an input signal based on information input by the user using the operating unit, and outputs the input signal to the CPU 901. The user of the robot arm apparatus 10 and the control device 20 can input various kinds of data to the robot arm apparatus 10 and the control device 20 or instruct the robot arm apparatus 10 and the control device 20 to perform a processing operation by operating the input device 915. For example, the input device 915 corresponds to the input unit 210 illustrated in FIG. 16 in the present embodiment. Further, in the present embodiment, the purpose of motion in driving of the arm unit 120 may be set by an operation input through the input device 915 by the user, and the whole body cooperative control may be performed according to the purpose of motion.

The output device 917 is configured with a device capable of visually or acoustically notifying the user of the acquired information. As such a device, there are a display device such as a CRT display device, a liquid crystal display device, a plasma display device, an EL display device or a lamp, an audio output device such as a speaker or a headphone, a printer device, and the like. For example, the output device 917 outputs a result obtained by various kinds of processes performed by the robot arm apparatus 10 and the control device 20. Specifically, the display device displays a result obtained by various kinds of processes performed by the robot arm apparatus 10 and the control device 20 in the form of text or an image. Meanwhile, the audio output device converts an audio signal including reproduced audio data, acoustic data, or the like into an analogue signal, and outputs the analogue signal. In the present embodiment, various kinds of information related to driving control of the arm unit 120 may be output from the output device 917 in all forms. For example, in driving control of the arm unit 120, the trajectory of movement of each component of the arm unit 120 may be displayed on the display screen of the output device 917 in the form of a graph. Further, for example, the display device 30 illustrated in FIG. 16 may be a device including the function and configuration of the output device 917 serving as the display device and a component such as a control unit for controlling driving of the display device.

The storage device 919 is a data storage device configured as an exemplary storage unit of the robot arm apparatus 10 and the control device 20. For example, the storage device 919 is configured with a magnetic storage unit device such as a hard disk drive (HDD), a semiconductor storage device, an optical storage device, a magneto optical storage device, or the like. The storage device 919 stores a program executed by the CPU 901, various kinds of data, and the like. For example, the storage device 919 corresponds to the storage unit 220 illustrated in FIGS. 1 and 16 in the present embodiment. Further, in the present embodiment, the storage device 919 may store the operation condition (the purpose of motion and the constraint condition) in the operation related to the whole body cooperative control using the generalized inverse dynamics, and the robot arm apparatus 10 and the control device 20 may perform the operation related to the whole body cooperative control using the operation condition stored in the storage device 919.

The drive 921 is a recording medium reader/writer, and is equipped in or attached to the robot arm apparatus 10 and the control device 20. The drive 921 reads information stored in the removable storage medium 927 mounted thereon such as a magnetic disk, an optical disc, a magneto optical disc, or a semiconductor memory, and outputs the read information to the RAM 905. Further, the drive 921 can write a record in the removable storage medium 927 mounted thereon such as a magnetic disk, an optical disk, a magneto optical disk, or a semiconductor memory. For example, the removable storage medium 927 is a DVD medium, an HD-DVD medium, a Blu-ray (a registered trademark) medium, or the like. Further, the removable storage medium 927 may be a Compact Flash (CF) (a registered trademark), a flash memory, a Secure Digital (SD) memory card, or the like. Furthermore, for example, the removable storage medium 927 may be an integrated circuit (IC) card equipped with a non-contact type IC chip, an electronic device, or the like. In the present embodiment, various kinds of information related to driving control of the arm unit 120 is read from various kinds of removable storage media 927 or written in various kinds of removable storage media 927 through the drive 921.

The connection port 923 is a port for connecting a device directly with the robot arm apparatus 10 and the control device 20. As an example of the connection port 923, there are a Universal Serial Bus (USB) port, an IEEE1394 port, a Small Computer System Interface (SCSI) port, and the like. As another example of the connection port 923, there are an RS-232C port, an optical audio terminal, a High-Definition Multimedia Interface (HDMI) (a registered trademark), and the like. As the external connection device 929 is connected to the connection port 923, the robot arm apparatus 10 and the control device 20 acquire various kinds of data directly from the external connection device 929 or provide various kinds of data to the external connection device 929. In the present embodiment, various kinds of information related to driving control of the arm unit 120 may be read from various kinds of external connection devices 929 or written in various kinds of external connection devices 929 through the connection port 923.

For example, the communication device 925 is a communication interface configured with a communication device used for a connection with a communication network (network) 931. For example, the communication device 925 is a communication card for a wired or wireless local area network (LAN), Bluetooth (a registered trademark), or wireless USB (WUSB). Further, the communication device 925 may be an optical communication router, an asymmetric digital subscriber line (ADSL) router, various kinds of communication modems, or the like. For example, the communication device 925 can transmit or receive a signal to or from the Internet or another communication device, for example, according to a certain protocol such as TCP/IP. The communication device 925 corresponds to the communication units 150 and 270 illustrated in FIG. 2 in the present embodiment, for example. Further, the communication network 931 connected to the communication device 925 is configured with a network connected in a wired or wireless manner, and may be, for example, the Internet, a domestic LAN, infrared ray communication, radio wave communication, satellite communication, or the like. In the present embodiment, various information for detecting a malfunction and various information related to driving control of the arm unit 120 may be transmitted and received between each joint unit 130 of the robot arm apparatus 10 and the arm unit 120 via the communication device 925. Additionally, various information related to driving control of the arm unit 120 may be transmitted and received bidirectionally by the communication device 925 with other external equipment via the communication network 931.

The hardware configuration capable of implementing the functions of the robot arm apparatus 10 and the control device 20 according to an embodiment of the present disclosure has been described above. Each of the above components may be configured using a versatile member, and may be configured by hardware specialized for the function of each component. Thus, the hardware configuration to be used may be appropriately changed according to a technology level when the present embodiment is carried out. Further, although not illustrated in FIG. 21, the robot arm apparatus 10 obviously includes various kinds of components corresponding to the arm unit 120 illustrated in FIGS. 1 and 16.

Further, it is possible to create a computer program for implementing the functions of the robot arm apparatus 10 according to the present embodiment, the control device 20, and the display device 30 and install the computer program in a personal computer or the like. Furthermore, it is possible to provide a computer readable recording medium storing the computer program as well. Examples of the recording medium include a magnetic disk, an optical disc, a magneto optical disc, and a flash memory. Further, for example, the computer program may be delivered via a network without using the recording medium.

<8. Supplement>

The preferred embodiments of the present disclosure have been described above with reference to the accompanying drawings, whilst the present disclosure is not limited to the above examples, of course. A person skilled in the art may find various alterations and modifications within the scope of the appended claims, and it should be understood that they will naturally come under the technical scope of the present disclosure.

In addition, the effects described in the present specification are merely illustrative and demonstrative, and not limitative. In other words, the technology according to the present disclosure can exhibit other effects that are evident to those skilled in the art along with or instead of the effects based on the present specification.

Additionally, the present technology may also be configured as below.

(1)

A robot arm apparatus including:

an arm unit made up of a plurality of links joined to each other by one or a plurality of a joint unit; and a driving control unit that drives the arm unit by controlling driving of the joint unit, wherein if a malfunction is detected in at least one of the joint unit, the driving control unit controls the driving of the joint unit in a state in which a certain restriction is imposed on motion of the arm unit, and drives the arm unit to avoid the malfunction.

(2)

The robot arm apparatus according to (1), wherein the malfunction of the joint unit is detected based on a torque generated in the joint unit in response to a pressing force imparted to an external object due to contact by the arm unit, and the driving control unit controls the driving of the joint unit and drives the arm unit in a state in which the pressing force is restricted to a certain range with respect to the motion of the arm unit.

(3)

The robot arm apparatus according to (2), wherein the pressing force is a force imparted to the external object by a front edge unit provided on a front edge of the arm unit.

(4)

The robot arm apparatus according to (3), further including:

a sensor that detects a force acting on the front edge unit, wherein the malfunction of the joint unit is detected based on a torque generated in the joint unit in response to the force acting on the front edge unit, and the force detected by the sensor.

(5)

The robot arm apparatus according to (1), wherein the malfunction of the joint unit is detected based on a rotational angle of the joint unit, and the driving control unit controls the driving of the joint unit and drives the arm unit in a state in which the rotational angle of the joint unit is restricted to a certain range with respect to the motion of the arm unit.

(6)

The robot arm apparatus according to (1), wherein the malfunction of the joint unit is detected based on a rotational angular velocity of the joint unit, and the driving control unit controls the driving of the joint unit and drives the arm unit in a state in which the rotational angular velocity of the joint unit is restricted to a certain range with respect to the motion of the arm unit.

(7)

The robot arm apparatus according to any one of (1) to (6), wherein the joint unit includes a joint state detecting unit that detects a state of the joint, and the malfunction of the joint unit is determined based on the state of the joint unit detected by the joint state detecting unit.

(8)

The robot arm apparatus according to (7), wherein the state of the joint unit includes at least one of a rotational angle of a motor, a rotational angle of an output shaft, a torque of the output shaft, a current supplied to the motor, and an ambient temperature of the motor in an actuator provided for driving the joint unit.

(9)

The robot arm apparatus according to any one of (1) to (8), wherein the driving control unit, according to a type of the malfunction detected in the joint unit, controls the driving of the joint unit in a manner that one operation is executed from among a malfunction avoidance operation that controls the driving of the joint unit in a state in which a certain restriction is imposed on motion of the arm unit, and drives the arm unit to avoid the malfunction, a partial function suspension operation that controls the driving of the one or plurality of the joint unit other than the joint unit where the malfunction has been detected, and drives the arm unit in a state of lowered degrees of freedom of the arm unit, and a function suspension operation in which the motion of all of the one or plurality of the joint unit constituting the arm unit is locked.

(10)

The robot arm apparatus according to any one of (1) to (9), wherein the driving control unit controls driving of the joint unit based on a state of the arm unit acquired based on a plurality of detected states of the joint unit.

(11)

The robot arm apparatus according to (10), wherein the driving control unit controls the driving of the joint unit based on the state of the arm unit and a control value for cooperative control of the arm unit, the control value being based on a purpose of motion and a constraint condition of the arm unit.

(12)

The robot arm apparatus according to (11), wherein the control value is computed based on a virtual force which is an imaginary force acting to achieve the purpose of motion in an operation space describing a relationship between a force acting on the arm unit and an acceleration produced in the arm unit, and also based on an actual force computed by converting the virtual force into a real force for driving the joint unit based on the constraint condition.

(13)

The robot arm apparatus according to (11), wherein the driving control unit controls driving of the joint unit based on a command value computed by correcting influence of a disturbance on the control value.

(14)

The robot arm apparatus according to (13), wherein the command value is computed by correcting the control value using a disturbance estimation value expressing influence of a disturbance on driving of the joint unit estimated based on a detected state of the joint unit.

(15)

The robot arm apparatus according to any one of (11) to (14), wherein the driving control unit controls the driving of the joint unit to produce a force compensating for gravity acting on the arm unit, and also a force that supports movement of the arm unit in a direction of a force additionally imparted from outside.

(16)

The robot arm apparatus according to any one of (11) to (14), wherein the driving control unit controls the driving of the joint unit in a manner that a front edge unit provided on a front edge of the arm unit performs a pivot operation of moving over a surface of a cone for which a certain point in real space serves as an apex of the cone.

(17)

The robot arm apparatus according to (16), wherein in the pivot operation, a distance between the front edge unit and the certain point is kept constant.

(18)

The robot arm apparatus according to any one of (1) to (17), wherein the robot arm apparatus is a robot arm apparatus for medical use, in which at least one medical tool is provided on the arm unit.

(19)

A robot arm control method including:

detecting, in an arm unit made up of a plurality of links joined to each other by one or a plurality of a joint unit, a malfunction in at least one of the joint unit; and controlling driving of the joint unit in a state in which a certain restriction is imposed on motion of the arm unit, and driving the arm unit to avoid the malfunction.

(20)

A program causing a processor of a computer to realize:

a function of detecting, in an arm unit made up of a plurality of links joined to each other by one or a plurality of a joint unit, a malfunction in at least one of the joint unit; and a function of controlling driving of the joint unit in a state in which a certain restriction is imposed on motion of the arm unit, and driving the arm unit to avoid the malfunction.

REFERENCE SIGNS LIST 1, 2 robot arm control system
10 robot arm apparatus
20 control device
30 display device
110 arm control unit
111 drive control unit
120 arm unit
130 joint unit
131 joint driving unit
132 rotational angle detecting unit
133 torque detecting unit
135 joint control unit
140 imaging unit
145 front edge unit
180 actuator
210 input unit
220 storage unit
230 control unit
240 whole body cooperative control unit
241 arm state acquiring unit
242 operation condition setting unit
243 virtual force calculating unit
244 actual force calculating unit
250 ideal joint control unit
251 disturbance estimating unit
252 command value calculating unit
260 malfunction detecting unit

The invention claimed is:

1. A medical support arm apparatus comprising:
an arm including a plurality of links joined to each other by at least one joint, the arm including a front edge supporting a medical tool used in a surgical procedure;
a driving controller configured to drive the arm by controlling driving of the at least one joint; and
at least one sensor configured to detect a state of the at least one joint indicated by at least one parameter, the at least one sensor detecting the state of the at least one joint during the surgical procedure,
wherein
a malfunction of the at least one joint is determined based on the state of the at least one joint detected by the at least one sensor and a comparison of the at least one parameter with a given threshold or a given state,
the at least one parameter is at least one of a rotational angle of a motor, a rotational angle of an output shaft, a torque of the output shaft, a current supplied to the motor, and an ambient temperature of the motor in an actuator provided for driving the joint, and
when the malfunction is detected in the joint, the driving controller controls the arm continuously such that the at least one joint with the malfunction is locked or quasi-locked, and joints other than the at least one joint with the malfunction are used to continue the surgical procedure.

2. The medical support arm apparatus according to claim 1, wherein
the malfunction of the joint is detected based on a torque generated in the joint in response to a pressing force imparted to an external object due to contact by the arm, and
the driving controller controls the driving of the joint and drives the arm in a state in which the pressing force is restricted to a certain range with respect to the motion of the arm.

3. The medical support arm apparatus according to claim 2, wherein
the pressing force is a force imparted to the external object by the front edge provided on the arm.

4. The medical support arm apparatus according to claim 3, wherein the sensor detects a force acting on the front edge, and
the malfunction of the joint is detected based on a torque generated in the joint in response to the force acting on the front edge, and the force detected by the sensor.

5. The medical support arm apparatus according to claim 1, wherein
the malfunction of the joint is detected based on a rotational angle of the joint, and
the driving controller controls the driving of the joint and drives the arm in a state in which the rotational angle of the joint is restricted to a certain range with respect to the motion of the arm.

6. The medical support arm apparatus according to claim 1, wherein
the malfunction of the joint is detected based on a rotational angular velocity of the joint, and
the driving controller controls the driving of the joint and drives the arm in a state in which the rotational angular velocity of the joint is restricted to a certain range with respect to the motion of the arm.

7. The medical support arm apparatus according to claim 1, wherein
the driving controller, according to a type of the malfunction detected in the joint, controls the driving of the joint in a manner that one operation is executed from among
a malfunction correction operation that controls the driving of the joint in a state in which a certain restriction is imposed on motion of the arm, and drives the arm to correct the malfunction,
a partial function suspension operation that controls the driving of another joint other than the joint where the malfunction has been detected, and drives the arm in a state of lowered degrees of freedom of the arm, and
a function suspension operation in which the motion of all of the joints constituting the arm is locked.

8. The medical support arm apparatus according to claim 1, wherein the driving controller controls driving of the joint based on a state of the arm acquired based on a plurality of detected states of the joint.

9. The medical support arm apparatus according to claim 8, wherein
the driving controller controls the driving of the joint based on the state of the arm and a control value for cooperative control of the arm, the control value being based on a purpose of motion and a constraint condition of the arm.

10. The medical support arm apparatus according to claim 9, wherein
the control value is computed based on a virtual force which is an imaginary force acting to achieve the purpose of motion in an operation space describing a relationship between a force acting on the arm and an acceleration produced in the arm, and also based on an actual force computed by converting the virtual force into a real force for driving the joint based on the constraint condition.

11. The medical support arm apparatus according to claim 9, wherein
the driving controller controls driving of the joint based on a command value computed by correcting influence of a disturbance on the control value.

12. The medical support arm apparatus according to claim 11, wherein
the command value is computed by correcting the control value using a disturbance estimation value expressing influence of a disturbance on driving of the joint estimated based on a detected state of the joint.

13. The medical support arm apparatus according to claim 9, wherein
the driving controller controls the driving of the joint to produce a force compensating for gravity acting on the arm, and also a force that supports movement of the arm in a direction of a force additionally imparted from outside.

14. The medical support arm apparatus according to claim 9, wherein
the driving control controls the driving of the joint in a manner that a front edge portion provided on a front edge of the arm performs a pivot operation of moving over a surface of a cone for which a certain point in real space serves as an apex of the cone.

15. The medical support arm apparatus according to claim 14, wherein
in the pivot operation, a distance between the front edge portion and the certain point is kept constant.

16. The medical support arm apparatus according to claim 1, wherein
the medical support arm apparatus is a support arm apparatus, in which at least one medical tool is provided on the arm.

17. A medical support arm control method comprising:
detecting, in an arm made up of a plurality of links joined to each other by at least one joint, the arm including a front edge supporting a medical tool used in a surgical procedure;
detecting a malfunction in the at least one joint by comparing a parameter of the at least one joint with a given threshold or a given state; and
controlling driving of the arm continuously such that the at least one joint with the malfunction is locked or quasi-locked, and joints other than the at least one joint with the malfunction are used to continue the surgical procedure,
wherein the parameter is at least one of a rotational angle of a motor, a rotational angle of an output shaft, a torque of the output shaft, a current supplied to the motor, and an ambient temperature of the motor in an actuator provided for driving the joint.

18. A non-transitory computer readable medium including a program causing a processor of a computer to execute:
detecting, in an arm made up of a plurality of links joined to each other by at least one joint, the arm including a front edge supporting a medical tool used in a surgical procedure;
detecting a malfunction of the at least joint by comparing a parameter of the at least joint with a given threshold or a given state; and
controlling driving of the arm continuously such that the at least one joint with the malfunction is locked or quasi-locked, and joints other than the at least one joint with the malfunction are used to continue the surgical procedure,
wherein the parameter is at least one of a rotational angle of a motor, a rotational angle of an output shaft, a torque of the output shaft, a current supplied to the motor, and an ambient temperature of the motor in an actuator provided for driving the joint.

* * * * *